(12) United States Patent
Kirby et al.

(10) Patent No.: US 10,524,728 B2
(45) Date of Patent: Jan. 7, 2020

(54) ACTIVITY MONITORING DEVICE WITH ASSESSMENT OF EXERCISE INTENSITY

(71) Applicant: NIKE, Inc., Beaverton, OR (US)

(72) Inventors: Brett S. Kirby, Portland, OR (US); Bradley W. Wilkins, Beaverton, OR (US); David Clark, Beaverton, OR (US); Eric Bradley, Beaverton, OR (US); Elizabeth Besemer, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 670 days.

(21) Appl. No.: 15/167,241

(22) Filed: May 27, 2016

(65) Prior Publication Data
US 2016/0345891 A1 Dec. 1, 2016

Related U.S. Application Data

(60) Provisional application No. 62/168,079, filed on May 29, 2015, provisional application No. 62/168,095, (Continued)

(51) Int. Cl.
*A61B 5/00* (2006.01)
*A61B 5/145* (2006.01)
(Continued)

(52) U.S. Cl.
CPC ............ *A61B 5/486* (2013.01); *A43B 3/0005* (2013.01); *A43B 7/141* (2013.01); *A43B 13/125* (2013.01);
(Continued)

(58) Field of Classification Search
CPC ...... A61B 5/486; A61B 5/4866; A61B 5/1123; A61B 5/224; A61B 5/14542; A61B 5/222;
(Continued)

(56) References Cited

U.S. PATENT DOCUMENTS 5,018,726 A 5/1991 Yorioka
5,067,710 A 11/1991 Watterson et al.
(Continued)

FOREIGN PATENT DOCUMENTS

CA 2022847 A1 2/1991
CA 2355849 A1 7/2000
(Continued)

OTHER PUBLICATIONS

Jean-Pierre Roy & Darren Stefanyshyn, Shoe Midsole Longitudinal Bending Stiffness and Running Economy, Joint Energy, and EMG, 2006, Applied Sciences, vol. 38, pp. 562-569, https://pdfs.semanticscholar.org/919b/28e08dbe2e65e03c20510e296ac85422ffe2.pdf (Year: 2006).*

(Continued)

*Primary Examiner* — Eric F Winakur
*Assistant Examiner* — Abid A Mustansir
(74) *Attorney, Agent, or Firm* — Banner & Witcoff, Ltd.

(57) ABSTRACT

Aspects relate to a portable device that may be used to identify a critical intensity and an anaerobic work capacity of an individual. The device may utilize muscle oxygen sensor data, speed data, or power data. The device may utilize data from multiple exercise sessions, or may utilize data from a single exercise session. The device may additionally estimate a critical intensity from a previous race time input from a user.

6 Claims, 43 Drawing Sheets

Related U.S. Application Data filed on May 29, 2015, provisional application No. 62/168,059, filed on May 29, 2015, provisional application No. 62/168,066, filed on May 29, 2015, provisional application No. 62/168,110, filed on May 29, 2015.

(51) Int. Cl.
- *A61B 5/22* (2006.01)
- *A63B 71/06* (2006.01)
- *A43B 3/00* (2006.01)
- *A61B 5/11* (2006.01)
- *G06Q 50/00* (2012.01)
- *A43B 13/12* (2006.01)
- *A43B 13/18* (2006.01)
- *A43B 7/14* (2006.01)
- *G16H 20/30* (2018.01)
- *G06Q 10/10* (2012.01)

(52) U.S. Cl.
CPC .......... *A43B 13/181* (2013.01); *A61B 5/0015* (2013.01); *A61B 5/1123* (2013.01); *A61B 5/14542* (2013.01); *A61B 5/222* (2013.01); *A61B 5/224* (2013.01); *A61B 5/4866* (2013.01); *A61B 5/6807* (2013.01); *A63B 71/06* (2013.01); *G06Q 10/10* (2013.01); *G06Q 50/01* (2013.01); *G16H 20/30* (2018.01); *A61B 2503/10* (2013.01)

(58) Field of Classification Search
CPC . A61B 5/6807; A61B 5/0015; A61B 2503/10; G06Q 10/10; G06Q 50/01; A43B 3/0005; G06F 19/3481; A63B 71/06
See application file for complete search history.

(56) References Cited

U.S. PATENT DOCUMENTS

| | | | |
|---|---|---|---|
| 5,167,230 A * | 12/1992 | Chance | A61B 5/0002 356/41 |
| 5,361,775 A | 11/1994 | Remes et al. | |
| 5,724,265 A | 3/1998 | Hutchings | |
| 5,752,521 A | 5/1998 | Dardik | |
| 6,006,129 A | 12/1999 | Watson | |
| 6,143,784 A | 11/2000 | Greenhaff et al. | |
| 6,185,451 B1 | 2/2001 | Richardson et al. | |
| 6,411,841 B2 | 6/2002 | Heikkila | |
| 6,450,967 B1 | 9/2002 | Wu | |
| 6,454,679 B1 | 9/2002 | Radow | |
| 7,764,990 B2 | 7/2010 | Martikka et al. | |
| 7,786,856 B2 | 8/2010 | O'Brien | |
| 8,996,088 B2 | 3/2015 | Dacso et al. | |
| 9,144,709 B2 | 9/2015 | Reich et al. | |
| 9,272,186 B2 | 3/2016 | Reich et al. | |
| 9,642,415 B2 | 5/2017 | Pease et al. | |
| 9,693,727 B1 | 7/2017 | Saalasti et al. | |
| 2002/0116147 A1 | 8/2002 | Vock et al. | |
| 2003/0149615 A1 | 8/2003 | Orban | |
| 2005/0101845 A1 | 5/2005 | Nihtila | |
| 2006/0032315 A1 | 2/2006 | Saalastic et al. | |
| 2006/0063980 A1 | 3/2006 | Hwang et al. | |
| 2006/0063995 A1 | 3/2006 | Yodh et al. | |
| 2006/0079800 A1 | 4/2006 | Martikka et al. | |
| 2007/0219059 A1 | 9/2007 | Schwartz et al. | |
| 2008/0015424 A1 * | 1/2008 | Bernreuter | A61B 5/14551 600/323 |
| 2008/0249736 A1 | 10/2008 | Prstojevich | |
| 2008/0275348 A1 | 11/2008 | Catt et al. | |
| 2009/0011907 A1 | 1/2009 | Radow et al. | |
| 2009/0024013 A1 * | 1/2009 | Soller | A61B 5/14551 600/324 |
| 2009/0137910 A1 | 5/2009 | Pyle et al. | |
| 2010/0096691 A1 | 4/2010 | Shin et al. | |
| 2010/0292549 A1 | 11/2010 | Shuler | |
| 2010/0317943 A1 | 12/2010 | Kuhn et al. | |
| 2010/0317946 A1 | 12/2010 | Kuhn et al. | |
| 2011/0021319 A1 | 1/2011 | Nissila et al. | |
| 2011/0106201 A1 | 5/2011 | Bhunia | |
| 2011/0205535 A1 | 8/2011 | Soller et al. | |
| 2012/0015778 A1 | 1/2012 | Lee et al. | |
| 2012/0041713 A1 | 2/2012 | Bonnet | |
| 2012/0239173 A1 | 9/2012 | Laikari et al. | |
| 2013/0041617 A1 * | 2/2013 | Pease | A43B 3/0005 702/139 |
| 2013/0053990 A1 | 2/2013 | Ackland | |
| 2013/0096403 A1 | 4/2013 | Dacso et al. | |
| 2013/0173174 A1 | 7/2013 | Baxi | |
| 2013/0178958 A1 | 7/2013 | Kulach et al. | |
| 2013/0190903 A1 | 7/2013 | Balakrishnan et al. | |
| 2013/0209978 A1 | 8/2013 | Chen et al. | |
| 2013/0217979 A1 | 8/2013 | Blackadar et al. | |
| 2014/0074407 A1 | 3/2014 | Hernandez-Silveira et al. | |
| 2014/0141937 A1 | 5/2014 | Kim et al. | |
| 2014/0223421 A1 | 8/2014 | Carter et al. | |
| 2014/0278229 A1 | 9/2014 | Hong et al. | |
| 2014/0288386 A1 | 9/2014 | Zand et al. | |
| 2014/0372064 A1 | 12/2014 | Darley et al. | |
| 2015/0005672 A1 | 1/2015 | Gangwish et al. | |
| 2015/0025816 A1 | 1/2015 | Ross | |
| 2015/0031970 A1 | 1/2015 | Lain | |
| 2015/0051721 A1 | 2/2015 | Cheng | |

FOREIGN PATENT DOCUMENTS

| | | |
|---|---|---|
| CA | 2900102 A1 | 8/2014 |
| EP | 2470066 A1 | 7/2012 |
| EP | 2578154 A1 | 4/2013 |
| EP | 2732758 A1 | 5/2014 |
| JP | 2001104288 A | 4/2001 |
| KR | 20110022548 A | 3/2011 |
| WO | 9101685 A1 | 2/1991 |
| WO | 2004071279 A2 | 8/2004 |
| WO | 2007002323 A2 | 1/2007 |
| WO | 2007048989 A1 | 5/2007 |
| WO | 2009118645 A1 | 10/2009 |
| WO | 2011053481 A1 | 5/2011 |
| WO | 2013056154 A1 | 4/2013 |
| WO | 2013070864 A2 | 5/2013 |
| WO | 2014121374 A1 | 8/2014 |
| WO | 2014201371 A1 | 12/2014 |
| WO | 2015057701 A1 | 4/2015 |
| WO | 2015063520 A1 | 5/2015 |

OTHER PUBLICATIONS

Sep. 16, 2016—(WO) ISR & WO—App. No. PCT/US16/034586.
Sep. 16, 2016—(WO) ISR & WO—App. No. PCT/US16/034659.
Sep. 16, 2016—(WO) ISR & WO—App. No. PCT/US16/034759.
Sep. 16, 2016—(WO) ISR & WO—App. No. PCT/US16/034650.
Sep. 16, 2016—(WO) ISR & WO—App. No. PCT/US16/034604.
Sep. 16, 2016—(WO) ISR & WO—App. No. PCT/US16/034556.
Jan. 7, 2019 (EP) Supp. ESR—App. No. 16804103.6.
Jul. 15, 2016—(WO) ISR & WO—App. No. PCT/US16/027771.
Alvarez, et al., Multisensor Approach to Walking Distance Estimation with Foot Inertial Sensing, Aug. 23-26, 2007, IEEE, 29th Annual International Conference, 5719-5721.
Di Prampero, et al., The critical velocity in swimming, Sep. 28, 2007, European Journal Applied Physiology, 102, p. 165-171.
Llyod, The Energetics of Running: An Analysis of World Records, Jan. 1966, Advancement of Science, p. 515-530.
Housh, Terry J., et al., "The effect of mathematical modeling on critical velocity." European Journal of Applied Physiology 84.5 (2001); pp. 469-475.
Vanhatalo, Anni, et al., "Application of Critial Power in Sport." Internation Journal of Sports Physiology and Pertormance 6.1 (2011); 128-136.
Feb. 1, 2019—(EP) ESR—App. No. 16804118.4.

(56) References Cited

OTHER PUBLICATIONS

Mar. 6, 2019—(EP) ESR—App. No. 16804145.7.
Feb. 22, 2019—(EP) ESR—App. No. 16804106.9.

* cited by examiner

ACTIVITY MONITORING DEVICE WITH ASSESSMENT OF EXERCISE INTENSITY

CROSS-REFERENCE TO RELATED APPLICATIONS

This application claims priority to U.S. Provisional Patent Application No. 62/168,059, filed on May 29, 2015, U.S. Provisional Patent Application No. 62/168,066, filed May 29, 2015, U.S. Provisional Patent Application No. 62/168,079, filed May 29, 2015, U.S. Provisional Patent Application No. 62/168,095, filed May 29, 2015, and U.S. Provisional Patent Application No. 62/168,110, filed May 29, 2015, which are expressly incorporated herein by reference in their entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Devices for tracking a user's activity may offer motivation in this regard, providing feedback on past activity, and encouragement to continue with an exercise routine in order to meet various exercise goals.

However, certain exercise metrics for athletes are assessed in formal lab-based settings, and using cumbersome equipment to monitor an individual while he/she exercises at a fixed location (e.g. on a treadmill or stationary bike). As such, these exercise metrics may not be readily available to the general population. Therefore, improved systems and methods to address at least one or more of these shortcomings in the art are desired.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

BRIEF DESCRIPTION OF THE DRAWINGS

FIG. 31A shows an average Quad muscle oxygenation slope; FIG. 31B shows the an average forearm muscle oxygenation slope; and FIG. 31C shows average muscle oxygenation slopes from a plurality of different locations, including calf, trapezius, and latissimus dorsi, in addition to plotting both quad and forearm slops;

FIG. 35B provides similar data specific to largely non-active; and FIG. 35C utilizes shows the alteration of equipment on the time to exhaustion estimate from MO2 signal in accordance with certain embodiments;

As shown in FIG. 38B, the instantaneous D' remaining is converted into units of time for easy display and athlete understanding.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
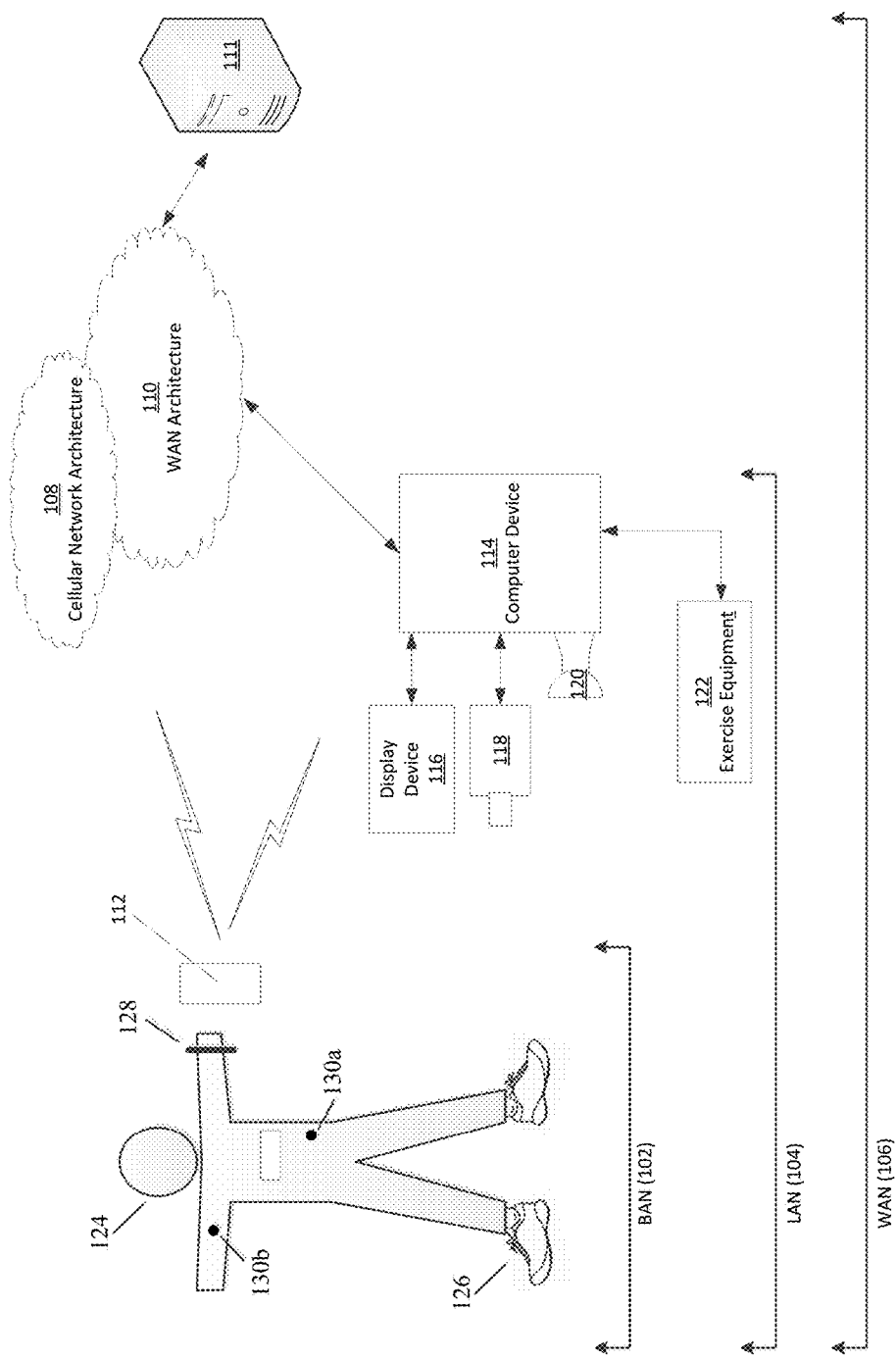
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
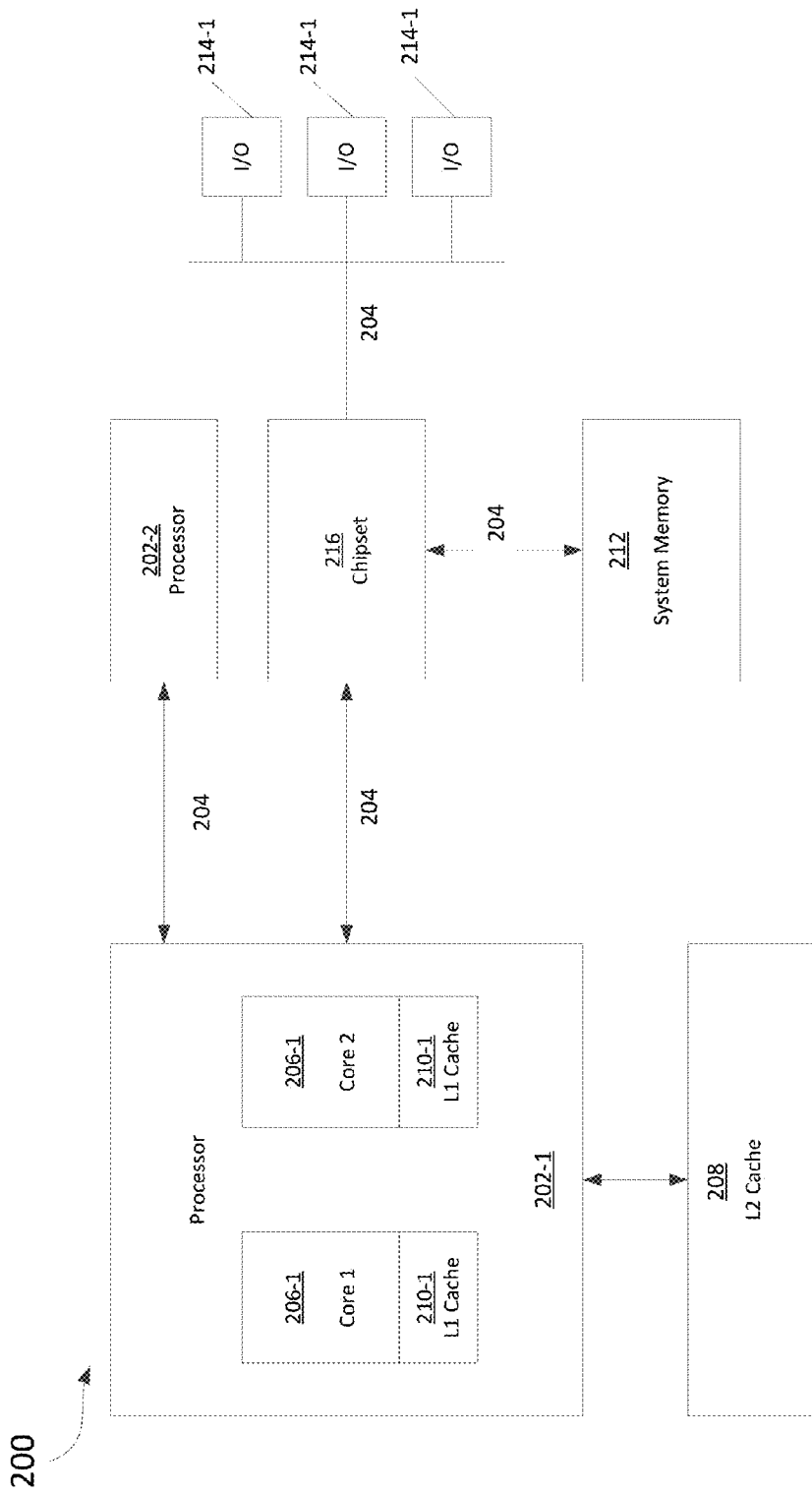
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
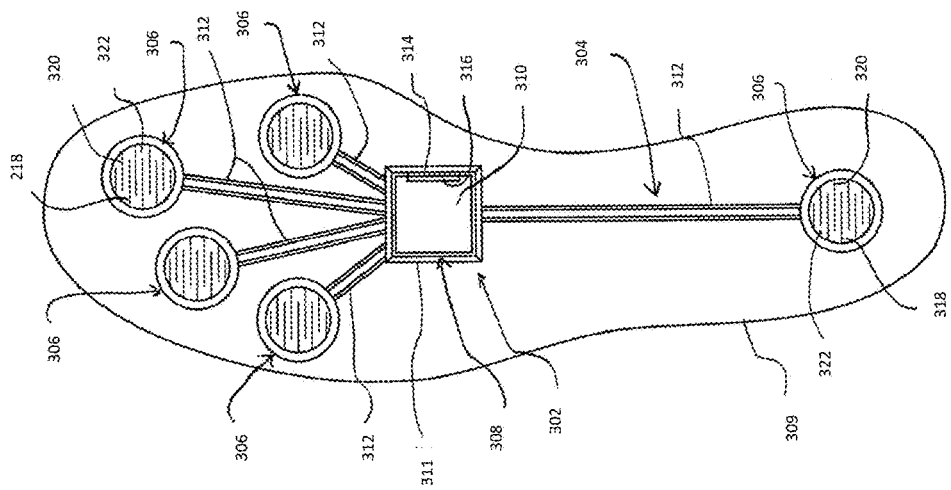
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
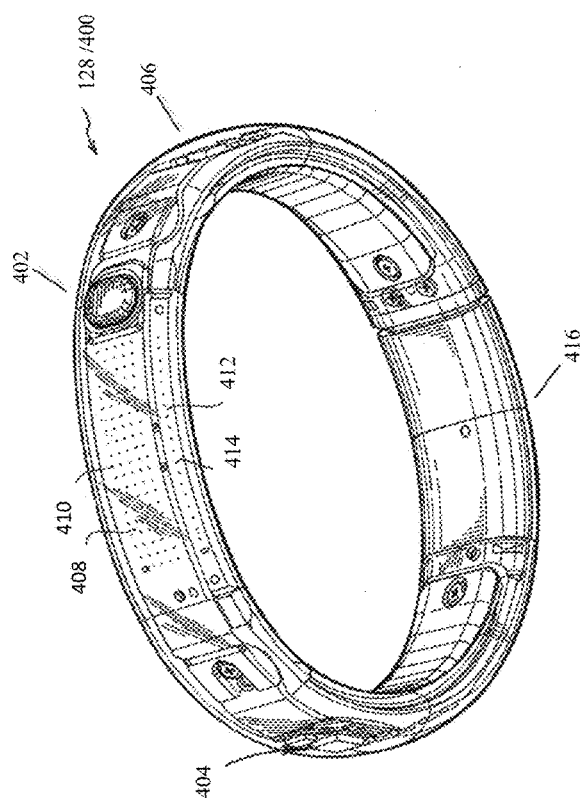
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
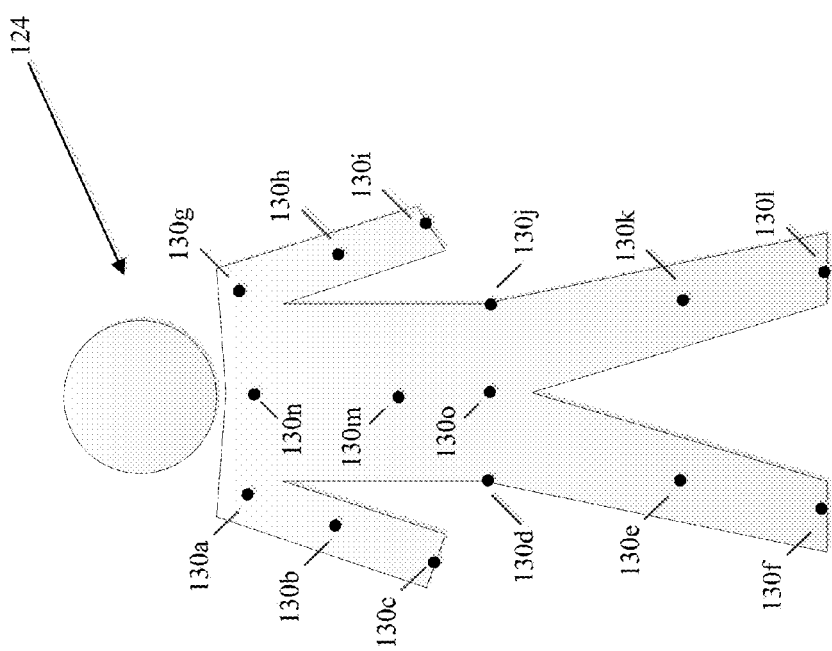
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Figure 6A:
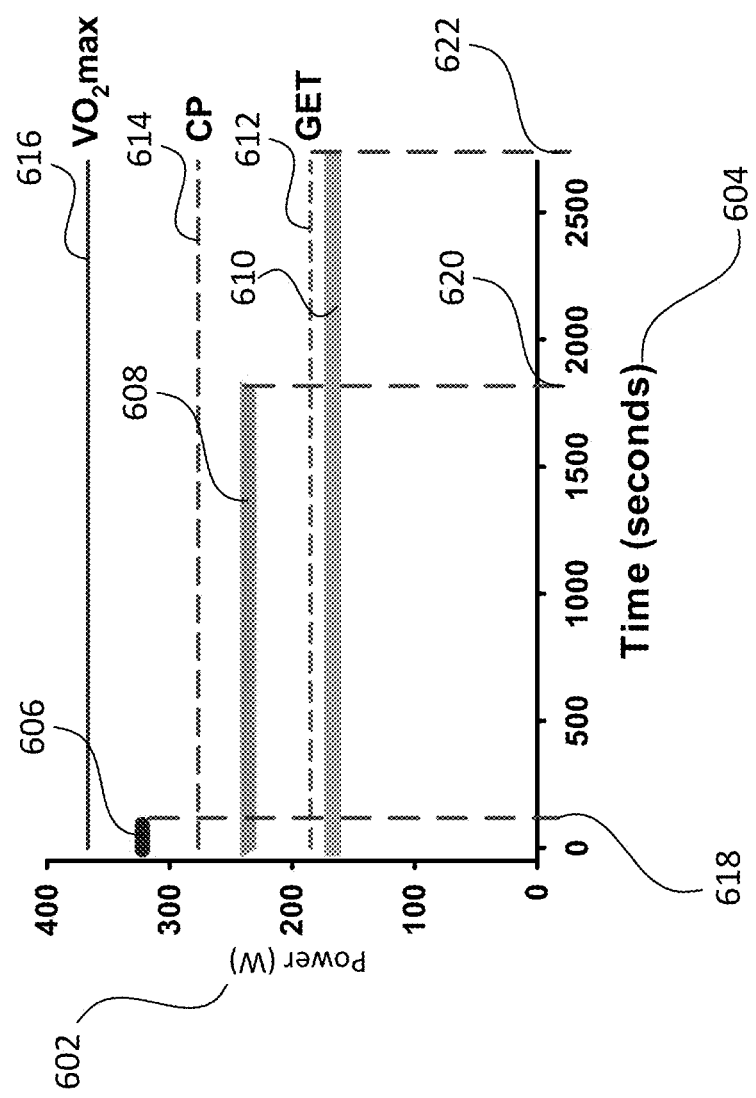
FIGS. 6A-6C depict graphs of exercise data associated with three exercise intensity domains, according to one or more aspects described herein.

Exercise may be categorized into multiple intensity domains. In one example, exercise may be categorized into four intensity domains, including: moderate, heavy, severe, and extreme, which are defined based on distinct metabolic profiles of an athlete or user. In one example, an athlete's exertion may be monitored using a power metric. FIG. 6A depicts three graphs; 606, 608, and 610, corresponding to three exercise sessions undertaken by a user, and such that exertion is graphed as power (y-axis 602) versus time (x-axis 604). Accordingly, graphs 606, 608, and 610 may correspond to three separate exercise sessions carried out at an approximately constant work rate. As such, graphs 606, 608, and 610 are depicted in FIG. 6A as approximately level graphs. In one specific example, the exercise sessions associated with graph 606, 608, and 610 may correspond to a user cycling against an approximately constant resistance (approximately constant speed, approximately constant gradient, approximately constant wind resistance, among others). In one example, each of the exercise sessions associated with graph 606, 608, and 610 may be carried out in a controlled environment, such as a lab-based environment, and such that an athlete may cycle on a stationary exercise bicycle against a controlled, and approximately constant resistance, and at an approximately constant speed. As such, a power associated with an exercise session may be calculated based on a resistance applied to the exercise bicycle, and a speed at which the person being monitored (referred to as the athlete or user) is cycling. In another example, graphs 606, 608, and 610 may correspond to three monitored running exercise sessions carried out against an approximately constant resistance (at an approximately constant speed, and an approximately constant gradient). As such, graphs 606, 608, and 610 may correspond to a user running on a treadmill at approximately constant speed and an approximately constant gradient. Additionally or alternatively, graphs 606, 608, and 610 may correspond to three exercise sessions monitored as a user cycles at three approximately constant work rates (approximately constant power) in a non-lab-based environment on a regular bicycle, or as a user runs at three approximately constant work rates in a non-lab-based environment. Furthermore, graphs 606, 608, and 610 may correspond to alternative forms of exercise (e.g. cross-country skiing, speed skating, among others).

Graphs 606, 608, and 610 schematically depict a same exercise type carried out by a same user at three approximately constant work rates corresponding to three different exercise intensity domains for that user. In particular, graph 610 may correspond to a moderate exercise intensity domain, graph 608 corresponds to a heavy exercise intensity domain, and graph 606 corresponds to a severe exercise intensity domain. In one example, a moderate exercise intensity domain may be defined as corresponding to an exercise intensity (power level) below a lactate threshold (LT), which is schematically depicted as threshold line 612 in FIG. 6A, and otherwise referred to as a gas exchange threshold (GET), lactate inflection point (LIP), or anaerobic threshold (AT). As such, a lactate threshold may correspond to an exercise intensity at which lactate (in particular, lactic acid) starts to accumulate in the bloodstream of the exercising user. In one specific example, graph 610 may be approximately 10% below the lactate threshold for the user being monitored.

In one example, graph 608 may correspond to a heavy exercise intensity domain, and such that a heavy exercise intensity domain may be defined as an exercise intensity carried out between the lactate threshold associated with line 612, and a critical intensity (CI) (otherwise referred to as a critical power (CP)). In one example, a critical intensity for the user associated with graphs 606, 608, and 610 may be denoted by line 614. As such, when an exercise intensity is below the critical intensity, any elevation in blood lactate and oxygen consumption ($VO_2$) may be stabilized after approximately 10 to 15 minutes. The work rate at a critical intensity may be defined as the highest sustainable work rate for a prolonged duration that does not elicit maximal oxygen uptake. In one example, graph 608 may be approximately 15% below the critical intensity 614.

Graph 606 may correspond to a severe exercise intensity domain. A severe exercise intensity domain may correspond to an exercise intensity above the critical intensity schematically depicted by line 614. As such, a work rate within the severe exercise intensity domain may lead, inexorably, to maximal oxygen consumption, which may be referred to as acute fatigue. The amount of work a user is able to do above the critical intensity may be capacity-limited, but rate-independent. In other words, the amount of work that a given user is able to perform above a critical intensity may be fixed, regardless of the rate at which the work is done (i.e. the power). This amount of work that the user is able to perform may be referred to as a finite reserve capacity, and may be denoted as W'. In one example, the finite reserve capacity may, alternatively, be referred to as an anaerobic capacity, or anaerobic work capacity. In one example, where the finite reserve capacity is expressed as a distance, it may be alternatively denoted by D'. In one example, the severe exercise session associated with graph 606 may be approximately 15% above the critical intensity associated with line 614.

Line 616 schematically denotes maximal oxygen consumption ($VO_{2max}$) for the user associated with graphs 606, 608, and 610. This maximal oxygen consumption may, alternatively, be referred to as maximal oxygen uptake, peak oxygen uptake, or maximal aerobic capacity, and may be the maximum rate of oxygen consumption for the user. In one example, the maximal oxygen consumption may be expressed in liters of oxygen per minute (L/min), or in milliliters of oxygen per kilogram of body mass per minute (mL/(kg·min)).

The length of each of graphs 606, 608, and 610 corresponds to the durations of the three exercise sessions within the moderate (graph 610), heavy (graph 608), and severe (graph 606) exercise intensity domains. Accordingly, the severe exercise intensity session 606 was carried out for a duration corresponding to time 618. Similarly, the heavy exercise intensity session 608 was carried out for a duration corresponding to time 620, and the moderate exercise intensity session 610 was carried out for a duration corresponding to time 622. In one implementation, knowledge of the critical intensity corresponding to line 614, an intensity above the critical intensity (e.g. an intensity associated with an exercise session corresponding to graph 606), and a duration 618 of the exercise session within the severe exercise intensity domain (i.e. above the critical intensity) may be utilized to calculate the finite reserve capacity for a user. In one example, the finite reserve capacity may be calculated as an integration of a power graph above the critical power. For the example of graph 606 (at constant power), the area under the graph but above the critical power may be calculated as:

Finite reserve capacity, $W'(J)$=Intensity above a critical intensity ($W$)×time to fatigue ($s$).

In one example, once a critical intensity and a finite work capacity associated with a given athlete are known (i.e. are identified and/or calculated), real-time monitoring of an athletic performance of the athlete, by an activity monitoring device, such as one or more of devices 112, 114, 128, 200, and/or 400, among others, may be used to provide feedback regarding a current exercise intensity relative to a critical intensity for the athlete. Additionally or alternatively, given a critical intensity and a finite work capacity associated with the athlete, the activity monitoring device may be utilized to predict one or more outcomes of a current exercise session. As such, an activity monitoring device may be utilized to, among others, predict a race time for an athlete. Further details related to utilization of critical intensity and finite work capacity information to provide feedback to a user are discussed later in the various disclosures that follow.

Figure 6B:
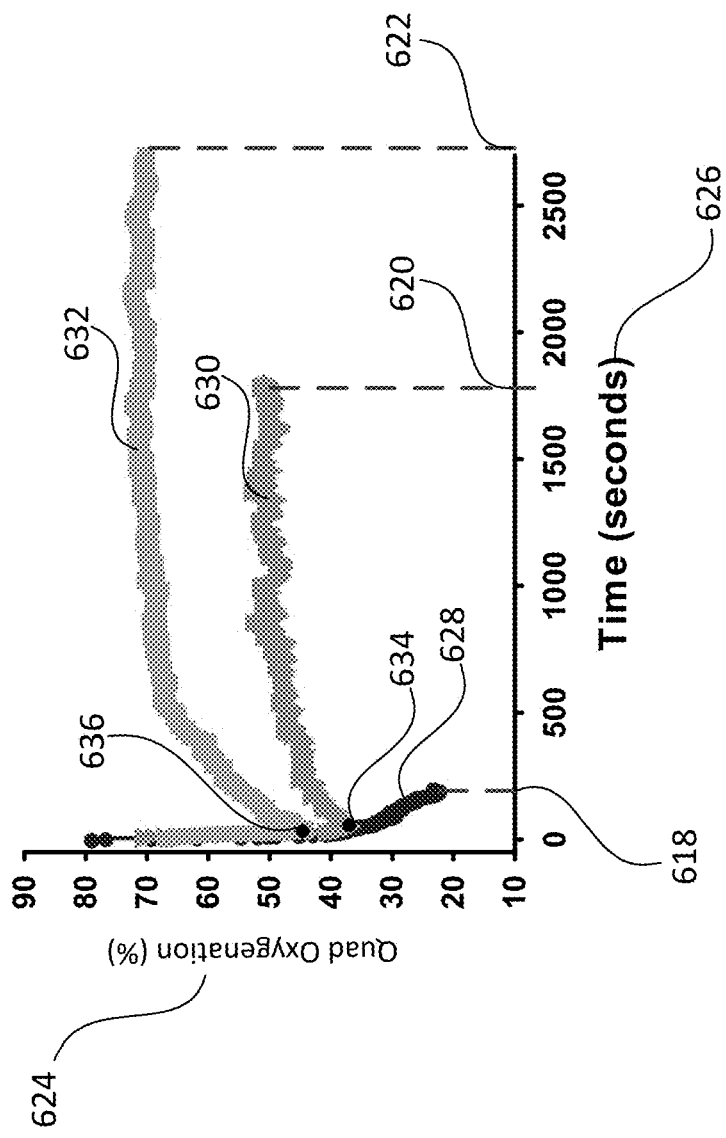

Muscle oxygenation, $MO_2$, may be utilized as a metric for monitoring exercise performance of an athlete. In one example, muscle oxygenation may be monitored in order to identify, among others, a critical intensity and/or anaerobic work capacity associated with an athlete. An activity monitoring device incorporating a muscle oxygenation sensor is discussed in further detail in relation to FIG. 7. FIG. 6B schematically depicts three graphs 628, 630, and 632 of muscle oxygenation percentage, $MO_2$ (%) (y-axis 624) versus time (x-axis 626). The three graphs 628, 630, and 632 correspond to the three graphs 606, 608, and 610 from FIG. 6A (i.e. the muscle oxygenation percentage data used to plot graphs 628, 630, and 632 was received from the exercise testing associated with graphs 606, 608, and 610). In one example, graphs 628, 630, and 632 may each depict muscle oxygenation percentage associated with a quadriceps muscle of an athlete, and such that for each of graphs 628, 630, and 632, the muscle oxygenation percentage data may be detected by a same sensor type (as described in further detail in relation to FIG. 7), and detected from an approximately same location on an athlete's body (i.e. proximate a quadriceps muscle of the athlete).

Graph 628 schematically depicts a progression of muscle oxygenation percentage of a quadriceps muscle of an athlete exercising within a severe exercise intensity domain (i.e. exercising at an intensity corresponding to graph 606). As depicted in FIG. 6B, graph 628 depicts a steady decline in muscle oxygenation percentage, without exhibiting an increase in muscle oxygenation percentage before the end of the exercise (point of fatigue) at time 618. Graph 630 schematically depicts a progression of muscle oxygenation percentage of a quadriceps muscle of an athlete exercising within a heavy exercise intensity domain (i.e. exercising at an intensity corresponding to graph 608). As depicted in FIG. 6B, graph 630 depicts a decline in muscle oxygenation percentage during a first time period, until point 634. At point 634, graph 630 exhibits a recovery in muscle oxygenation percentage before the exercise is completed (before the athlete fatigues) at time 620. Graph 632 schematically depicts a progression of muscle oxygenation percentage of the quadriceps muscle of the athlete exercising within a moderate exercise intensity domain (i.e. exercising at an intensity corresponding to graph 610). As depicted in FIG. 6B, graph 632 depicts a decline in muscle oxygenation percentage during a first time period, until point 636. At point 636, graph 632 exhibits a recovery in muscle oxygenation percentage before the exercise is completed at time 622.

As previously discussed, the data used to plot graphs 628, 630, and 632 may be received from a sensor configured to detect muscle oxygenation of a quadriceps muscle of an athlete. Further, the exercise sessions associated with graphs 628, 630, and 632 may include cycling or running sessions, among others, and such that the athlete's leg muscles are considered active muscles for the exercise sessions (i.e. as opposed to the athlete's arm muscles, among others). In summary, FIG. 6B schematically depicts that muscle oxygenation percentage of an active quadriceps muscle for a given exercise section may exhibit recovery from an initial decline when exercising within a moderate (graph 632) or a heavy (graph 630) exercise intensity domain, but that muscle oxygenation percentage will not recover when exercising within a severe exercise intensity domain.

Figure 6C:
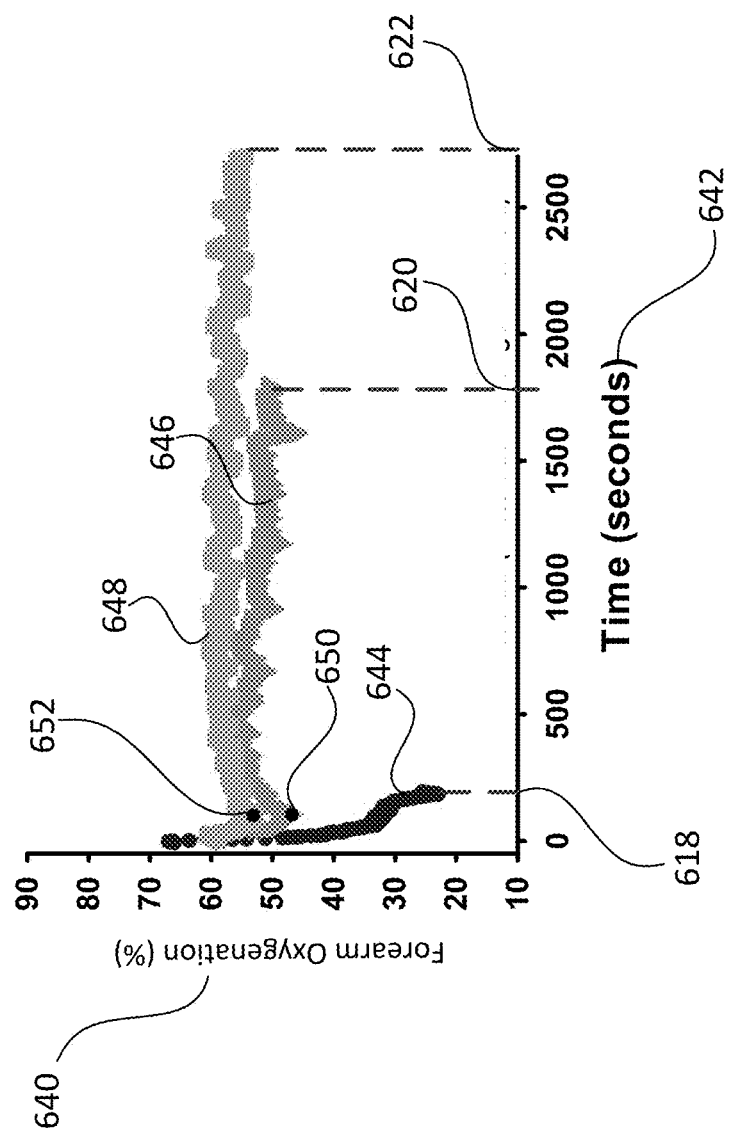

FIG. 6C schematically depicts three graphs 644, 646, and 648 of muscle oxygenation percentage (y-axis 640) versus time (x-axis 642). The three graphs 644, 646, and 648 correspond to the three graphs 606, 608, and 610 from FIG. 6A (i.e. the muscle oxygenation percentage data used to plot graphs 644, 646, and 648 may be received from the exercise testing associated with graphs 606, 608, and 610). In one example, graphs 644, 646, and 648 may each depict muscle oxygenation percentage associated with a forearm muscle of the athlete. As such, graphs 644, 646, and 648 may be associated with an inactive muscle for an exercise session that concentrates on the athlete's leg muscles (e.g. cycling or running, among others). As such, graphs 644, 646, and 648 may be plotted from data detected by a same sensor type (as described in further detail in relation to FIG. 7), and detected from an approximately same location on the athlete's body (i.e. proximate a forearm muscle of the athlete).

In one example, graphs 644, 646, and 648 may exhibit similar trends to graphs 628, 630, and 632 from FIG. 6B. In particular, graph 644 depicts a steady decline in muscle oxygenation percentage, without exhibiting an increase in muscle oxygenation percentage before the end of the exercise (at point 618). As such, graph 644 may be associated with a severe exercise intensity domain, and with graph 606 from FIG. 6A. Graph 646 schematically depicts a progression of muscle oxygenation percentage of a forearm muscle of an athlete exercising within a heavy exercise intensity domain (i.e. exercising at an intensity corresponding to graph 608). As depicted in FIG. 6C, graph 646 depicts a decline in muscle oxygenation percentage during a first time period, up until point 650. At point 650, graph 646 exhibits a recovery in muscle oxygenation percentage before the exercise is completed at time 620. Graph 648 schematically depicts a progression of muscle oxygenation percentage of a forearm muscle of the athlete exercising within a moderate exercise intensity domain (i.e. exercising at an intensity corresponding to graph 610). As depicted in FIG. 6C, graph 648 depicts a decline in muscle oxygenation percentage during a first time period, up until point 652. At point 652, graph 648 exhibits a recovery in muscle oxygenation percentage before the exercise is completed at time 622.

Accordingly, FIGS. 6B and 6C schematically depict that similar trends in muscle oxygenation percentage may be exhibited by both active and inactive muscles when exercising within moderate, heavy, and severe exercise intensity domains. In this way, a muscle oxygenation sensor, such as that described in further detail in relation to FIG. 7, may be positioned on an active or inactive muscle in order to detect useful activity data for an athlete.

Figure 7:
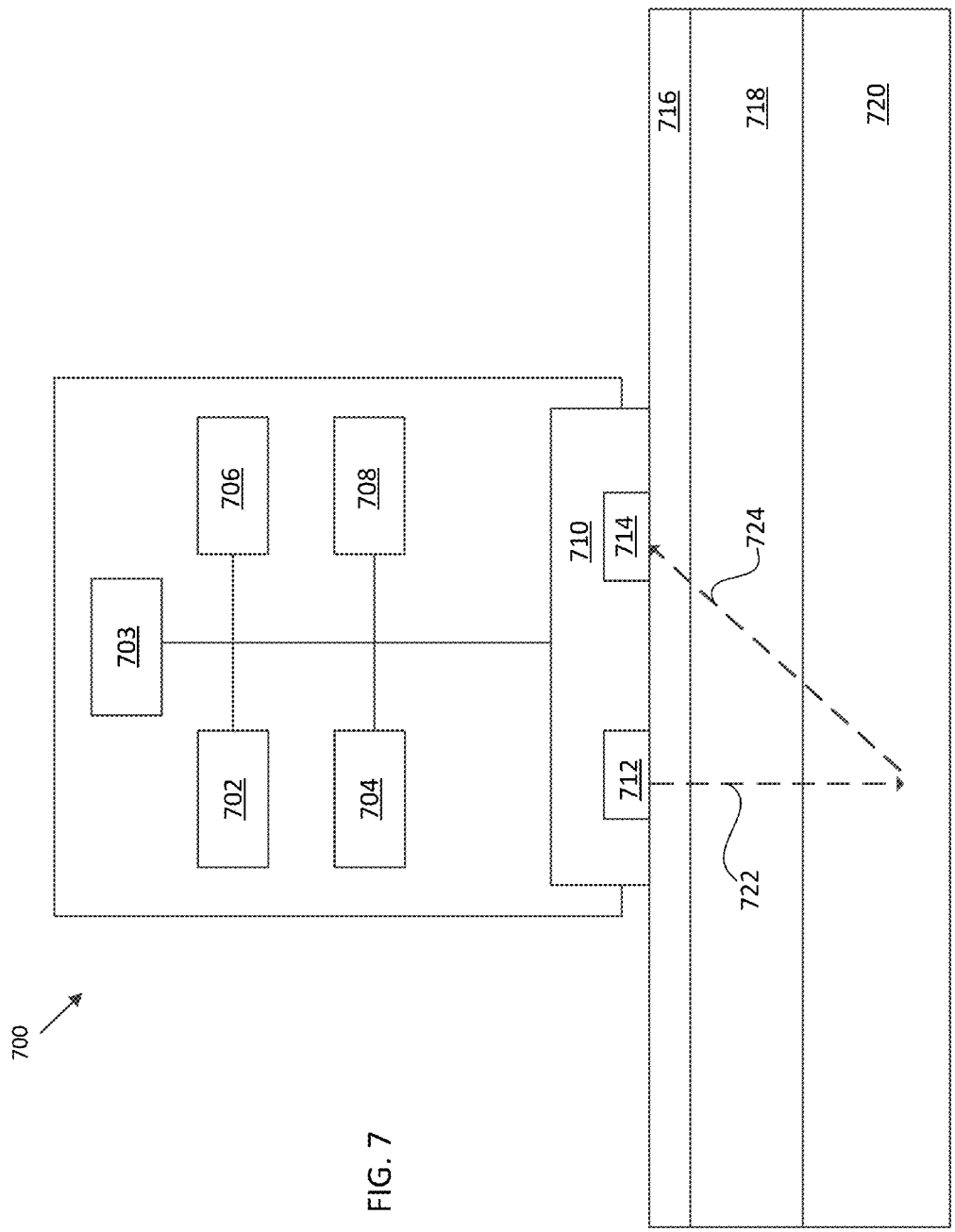
FIG. 7 schematically depicts an activity monitoring device, according to one or more aspects described herein.

FIG. 7 schematically depicts an activity monitoring device 700. In one example, the activity monitoring device 700 may include one or more elements and/or functionality similar to devices 112, 114, 128, 200, and/or 400, among others. Accordingly, the activity monitoring device 700 may comprise a processor 702, which may be similar to one or more of processors 202-1 and 202-2. Processor 702 may comprise one or more processing cores configured to execute one or more computational instructions in parallel. Additionally or alternatively, processor 702 may utilize one or more processing cores to execute computational instructions in series, or a combination of series and parallel processing. Further, processor 702 may be embodied with any computational clock speed (clock speed may be related to a rate at which computational instructions may be executed by the processor 702) disclosed herein or generally known in the art. In one example, the processor 702 may be configured to execute computer-executable instructions stored on a non-transitory computer-readable medium, such as memory 704. As such, memory 704 may be similar to memory 212, and may include, but may not be limited to, persistent or volatile memory. As such, memory 704 may include one or more of random access memory (RAM), read only memory (ROM), solid-state memory, optical or magnetic storage, and/or any other medium that can be used to store electronic information.

In one implementation, electrical energy may be provided to one or more of the components (i.e. components 702, 704, 706, 708, and/or 710) of the activity monitoring device 700 by a power supply 703. As such, the power supply 703 may comprise one or more of a battery, a photovoltaic cell, a thermoelectric generator, or a wired electrical supply from an external source. Further, the power supply 703 may be configured to supply one or more components of the activity monitoring device 700 with an electrical output having any voltage, and configured to supply any current, without departing from the scope of these disclosures.

The activity monitoring device 700 may include a sensor 706. As such, sensor 706 may comprise an accelerometer, a gyroscope, a location-determining device (e.g., GPS), temperature sensor (including ambient temperature and/or body temperature), sleep pattern sensors, heart rate monitor, image-capturing sensor, moisture sensor, force sensor, compass, angular rate sensor, and/or combinations thereof among others. In one implementation, the activity monitoring device 700 may include an interface 708. As such, the interface 708 may be embodied with hardware and/or firmware and software configured to facilitate communication between the activity monitoring device 700 and external device or network, not depicted in FIG. 7. In one example, the interface 708 may facilitate wireless and/or wired communication between the activity monitoring device 700 and an external device or network. In one example, interface 708 may facilitate communication using one or more of Wi-Fi, Bluetooth, an Ethernet cable, a USB connection, or any other connection type disclosed herein or known in the art. As such, interface 708 may facilitate communication between the activity monitoring device 700 and an external device across a local area network (LAN), a wide area network (WAN), or the Internet, among others. Additionally or alternatively, interface 708 may facilitate communication between the activity monitoring device 708 and a user interface. As such, a user interface may include a display device, such as display device 116 and/or one or more input interfaces (e.g. one or more button interfaces, touchscreen interfaces, microphone interfaces, and the like).

Additionally or alternatively, the activity monitoring device 700 may include a muscle oxygenation sensor 710. In one example, the muscle oxygenation sensor 710 may be configured to emit electromagnetic radiation in a near-infrared wavelength range. As such, the muscle oxygenation sensor 710 may utilize near-infrared spectroscopy (NIRS). By positioning the muscle oxygenation sensor 710 proximate an area of skin 716 of a user, the emitted electromagnetic radiation, which is schematically depicted by arrow 722, may travel into the user's body through, in one example, a layer of skin 716, fat 718, and into a muscle tissue 720. In one example, oxyhemoglobin and deoxyhemoglobin may act as chromophores (absorbing differing amounts of light at different wavelengths). Further, oxyhemoglobin and deoxyhemoglobin may exhibit comparatively larger differences in absorption characteristics across a range of near infrared electromagnetic radiation. As such, the emitter 712 may be configured to emit electromagnetic radiation in a near infrared spectrum having a wavelength range of approximately 600 to 900 nm. In another example, the emitter 712 may be configured to emit infrared light having a wavelength range of approximately 630 to 850 nm. In yet another example, the emitter 712 may be configured to emit infrared light across another range, without departing from the scope of these disclosures. In one example, the emitter 712 may comprise one or more light emitting diode (LED) elements. In one specific example, the emitter 712 may comprise four light emitting diodes.

Accordingly, a portion of light emitted from the emitter 712 may be backscattered and detected by detector 714. In one example, line 724 may represent a portion of back scattered light detected by detector 714. As such, the muscle oxygenation sensor 710 may be configured to calculate an attenuation in intensity between emitted and detected light. This attenuation may be related to an amount of light absorbed by, among others, the oxyhemoglobin and deoxyhemoglobin chromophores. As such, by detecting an attenuation in emitted near infrared light, the muscle oxygenation sensor 710 may determine a concentration of oxyhemoglobin or deoxyhemoglobin. In turn, based upon the determined concentration of oxyhemoglobin or deoxyhemoglobin, the muscle oxygenation sensor 710 may calculate a muscle oxygenation percentage associated with the muscle 720.

In one implementation, the muscle oxygenation sensor 710 may calculate a muscle oxygenation percentage associated with muscle tissue 720 according to the Beer-Lambert law:

$$\log(I_{out}/I_{in}) = \varepsilon \cdot L \cdot c$$

where $I_{in}$ is an intensity of near-infrared radiation emitted from the emitter 712, $I_{out}$ is an intensity of near-infrared radiation detected by detector 714, $\varepsilon$ is a molar attenuation coefficient of the chromophore, c is an amount concentration of the chromophore, and l is a path length that the emitted near infrared radiation travels through the body (i.e. one or more of skin 716, fat 718, and muscle 720.

It will be appreciated that the light emitted from emitter 712 is schematically represented by line 722, and that portion of emitted light detected by detector 714 is schematically represented by line 724. In practice, a path of light emitted from emitter 712 traveling into a user's body (i.e. through one or more of skin 716, fat 718, and muscle 720), and light detected by detector 714 may be complex, and comprise a plurality of different paths.

In one example, the muscle oxygenation sensor 710 of the activity monitoring device 700 may be configured to be positioned proximate an area of skin 716 of a user. As such, in one example, the emitter 712 and the detector 714 may be positioned such that there exists substantially no separation between the emitter 712 and the skin 716, and similarly, substantially no separation between the detector 714 and the skin 716. In another example, the activity monitoring device 700 may be configured to be positioned proximate an area of skin 716 of a user, such that a gap between the emitter 712 and the skin 716, and/or the detector 714 in the skin 716 does not include a layer of clothing. In yet another example, the activity monitoring device 700 may be configured to be positioned proximate an area of skin 716 of a user, such that one or more layers of clothing may be positioned between the emitter 712 and the skin 716, and/or the detector 714 and the skin 716.

Figure 8:
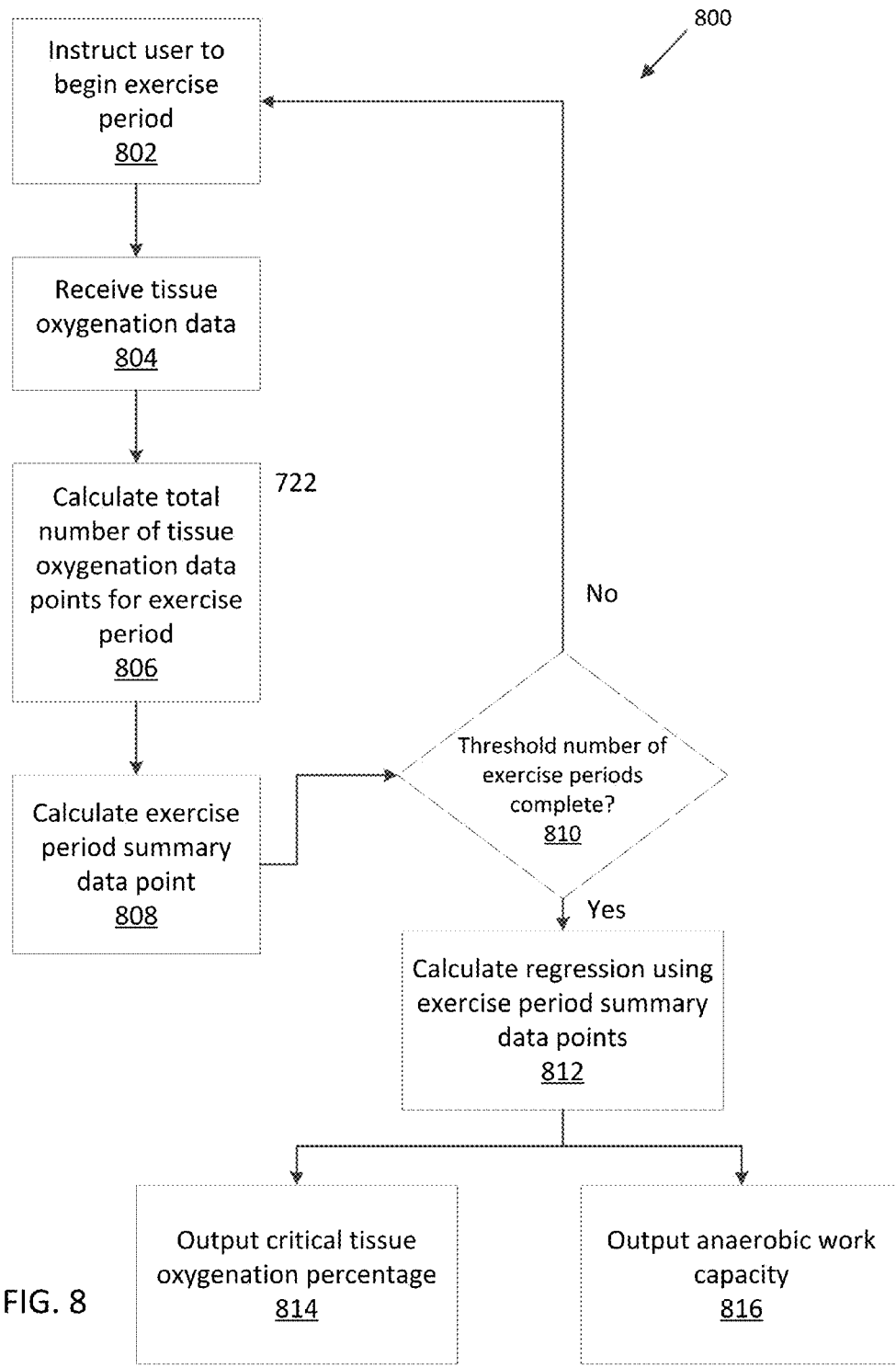
FIG. 8 schematically depicts a flowchart diagram for calculation of a critical tissue oxygenation percentage and/or an anaerobic work capacity, from a tissue oxygenation sensor data, according to one or more aspects described herein.

In one example, the activity monitoring device 700, and in particular, the muscle oxygenation sensor 710, may be utilized to determine (in one example, to calculate) a critical intensity and/or an anaerobic work capacity associated with a user. In one specific example, the muscle oxygenation sensor 710 may be utilized to determine a critical muscle oxygenation percentage at which a user reaches a critical intensity of exercise. Accordingly, FIG. 8 schematically depicts a flowchart diagram 800 that may be utilized to calculate one or more of a critical tissue oxygenation percentage and/or an anaerobic work capacity of a user from data outputted from a tissue oxygenation sensor, such as sensor 710. As such, the critical tissue oxygenation percentage may, in one example, be a critical tissue oxygenation percentage of muscle tissue, among others.

In one implementation, in order to calculate one or more of a critical tissue oxygenation percentage and/or an anaerobic work capacity, a user may provide an activity monitoring device, such as device 700, with test data. In one example, test data may be generated by the sensor, such as sensor 710, during an exercise period, which may otherwise be referred to as an exercise session. In one example, an exercise period may comprise a prescribed duration during which a user is instructed to run as quickly as possible (i.e. as far as possible) within the prescribed time limit. In certain specific examples, an exercise period may instruct a user to run as far as possible within, for example, a minute, two minutes, three minutes, four minutes, five minutes, six minutes, seven minutes, eight minutes, nine minutes, 10 minutes, 12 minutes, 15 minutes, 20 minutes, or any other duration. Accordingly, a tissue oxygenation sensor, such as sensor 710, may be configured to output a tissue oxygenation percentage data point each second during an exercise period. Alternatively, the tissue oxygenation sensor, such as sensor 710, may be configured to output a tissue oxygenation percentage data point at a different frequency, which may be 0.25 Hz, 0.5 Hz, 2 Hz, 3 Hz, 4 Hz, or any other frequency. In one example, an exercise period prescribed for a user in order to generate test data may ensure that the user exercises at an intensity above a critical intensity for the user during at least a portion of the prescribed duration of the exercise period. Accordingly, in one example, one or more processes may be executed to instruct a user to begin an exercise period at block 802 of flowchart 800.

As previously discussed, a tissue oxygenation sensor, such as sensor 710, may be used to detect, and to output data indicative of, a tissue oxygenation percentage. In one example, the tissue oxygenation sensor 710 may output a data point indicative of a current tissue oxygenation percentage for each second of an exercise period. Accordingly, in one example, the outputted tissue oxygenation data may be received for further processing by, in one example, processor 702, at block 804 of flowchart 800.

In one implementation, a tissue oxygenation percentage for each second of a prescribed exercise period may be stored. As such, tissue oxygenation percentages for each second of a prescribed exercise period may be stored in, for example, memory 704. Upon completion of a given exercise period, a number may be calculated corresponding to a total number of the stored tissue oxygenation percentages for each second of a duration of a prescribed exercise period. This number may be referred to as a total number of tissue oxygenation data points for an exercise period. This total number of tissue oxygenation data points may be calculated by, in one example, processor 702, and at block 806 of flowchart 800.

An exercise period utilized to generate data in order to determine a critical muscle oxygenation percentage and/or an anaerobic work capacity of the user may be summarized as a data point comprising two pieces of information. This exercise period summary data point may comprise the total number of tissue oxygenation data points, as determined, in one example, at block 806, in addition to the total time (i.e. the duration) of the exercise period/session. In one example, the two pieces of information (i.e. the total number of tissue oxygenation data points, and the total time) may be expressed as a coordinate point. In one example, this coordinate point P may be of the form $P(x_1, y_1)$, where $y_1$ may be the total number of tissue oxygenation data points (muscle oxygenation percentage (%)×time (s)), and $x_1$ may be the total time (s). In this way, the exercise period summary data point expressed as a coordinate point may be plotted, as schematically depicted in FIG. 9. In one example, the exercise period summary data point may be calculated at block 808 of flowchart 800.

In one implementation, in order to calculate one or more of a critical tissue oxygenation percentage and/or an anaerobic work capacity of a user, two or more exercise period summary data points may be utilized. In one example, the durations of the exercise periods used to generate the two or more exercise period summary data points may be different. Accordingly, in one example, one or more processes may be executed to determine whether a threshold number of exercise periods have been completed by the user in order to calculate one or more of a critical tissue oxygenation percentage and/or an anaerobic work capacity for the user. As previously described, this threshold number of exercise periods may be at least two, at least three, at least four, or at least five, among others. In one specific example, one or more processes may be executed by processor 702 to determine whether the threshold number of exercise periods have been completed at decision block 810 of flowchart 800. Accordingly, if the threshold number of exercise periods has been met or exceeded, flowchart 800 proceeds to block 812. If, however, the threshold number of exercise periods has not been met, flowchart 800 proceeds from decision block 810 back to block 802.

In one example, a regression may be calculated using the two or more exercise period summary data points that were calculated from two or more prescribed exercise periods. This regression may be a linear, or a curvilinear regression. As such, any computational processes known in the art for calculation of a linear or curvilinear regression may be utilized with this disclosure. In one implementation, at least a portion of a calculated regression may be utilized to determine one or more of a critical tissue oxygenation percentage and/or an anaerobic work capacity of the user. In one specific example, one or more processes may be executed to calculate a regression at block 812 of flowchart 800.

At least a portion of a regression calculated using the two or more exercise period summary data points may be utilized to determine a critical tissue oxygenation percentage for a user. Specifically, the critical tissue oxygenation percentage may correspond to a slope of the regression line (or a slope of a linear portion of a curvilinear regression). One or more processes may be executed to output a critical tissue oxygenation percentage calculated as a slope of a regression line through the two or more exercise period summary data points at block 814 of flowchart 800.

At least a portion of a regression calculated using the two or more exercise period summary data points may be utilized to determine an anaerobic capacity of the user. Specifically, the anaerobic capacity may correspond to an intercept of the regression line (or an intercept of a linear portion of a curvilinear regression). In one example, the anaerobic capacity may be expressed as a total number of tissue oxygenation data points (tissue oxygenation percentage (%)×time (s)) above a critical oxygenation percentage (%). In one implementation, one or more processes may be executed to output an anaerobic capacity calculated as an intercept of a regression line through the two or more exercise period summary data points at block 816 of flowchart 800.

Figure 9A:
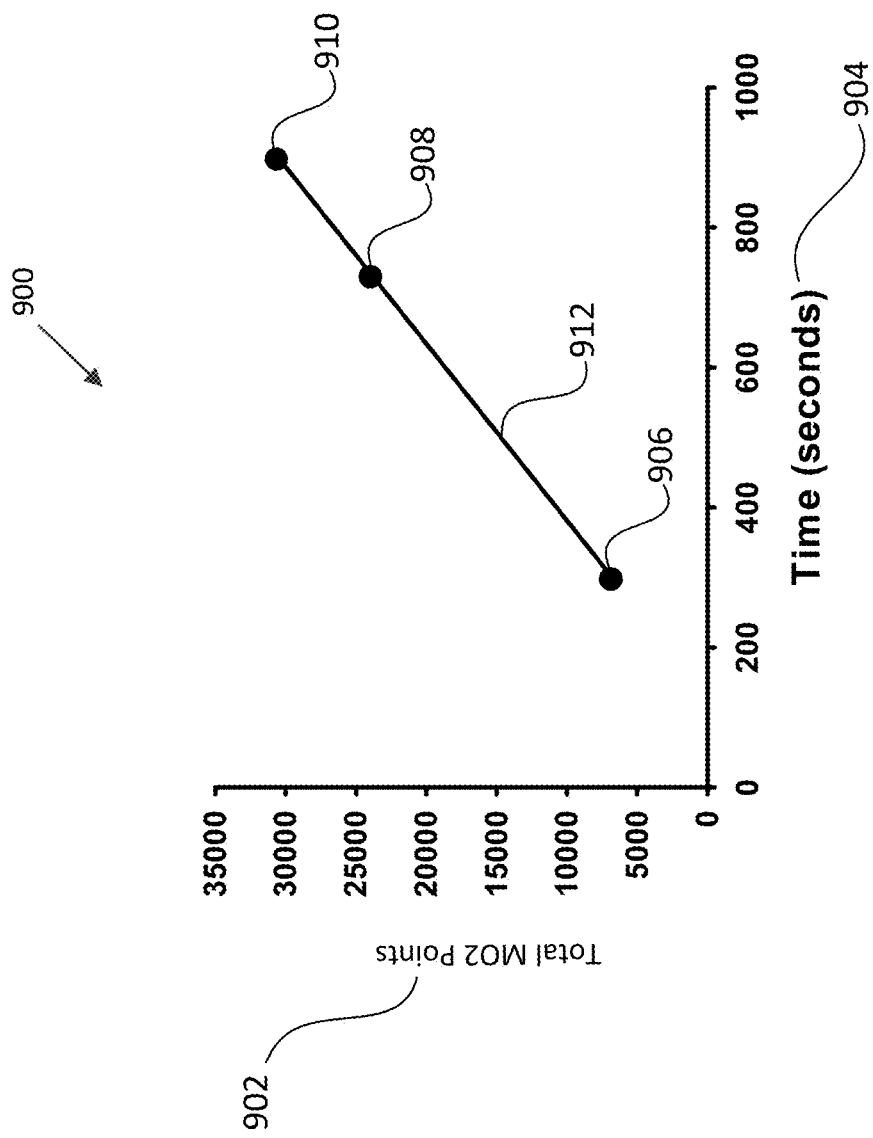
FIGS. 9A-9B depict graphs of muscle oxygenation sensor data from multiple exercise sessions, according to one or more aspects described herein.

FIG. 9A is a chart that plots testing data from multiple exercise periods, or sessions, for a given user. In particular, FIG. 9A is a chart 900 plotting total muscle oxygenation points 902 against time 904. Points 906, 908, and 910 are each exercise period summary data points, as described in relation to FIG. 8. As such, the exercise period summary data points 906, 908, 910 may be calculated for a same user, and for, in this example, three separate exercise sessions. Accordingly, each of the exercise period summary data points 906, 908, and 910 may represent a separate exercise session. In particular, the exercise sessions associated with the exercise period summary data points 906, 908, and 910 may have durations of approximately 300 seconds, 720 seconds, and 900 seconds, respectively. Further, during the respective exercise sessions, muscle oxygenation percentage data detected for the user may be integrated for each second of a total duration of a given exercise session to give a total number of muscle oxygenation points equal to approximately 6000, 25,000, and 30,000 for the respective exercise period summary data points 906, 908, and 910.

In one example, the exercise period summary data points 906, 908, 910 may each represent a separate exercise session, and such that a portion of each of these exercise sessions is carried out within a severe exercise intensity domain for a user. In one implementation, the exercise period summary data points 906, 908, 910 may each represent a separate exercise session carried out in a continuous manner (nonstop exercise without breaks, e.g. continuous running and/or cycling). However, in another implementation, one or more of the exercise period summary data points 906, 908, 910 may each represent a separate exercise session carried out in an intermittent manner (a non-continuous exercise session with one or more periods of inactivity/low activity and one or more periods of high activity, e.g. participation in team sports, such as basketball, soccer, and the like).

In one implementation, a regression line 912 may be calculated using the three exercise period summary data points 906, 908, and 910, as plotted on chart 900. In one example, this regression line 912 may be of the form:

$$y = m_a x + c_a$$

where y is a total number of muscle oxygenation points (y-axis), x is a time (s) (x-axis), $m_a$ is the slope of the regression line 912, and $c_a$ is the intercept of the regression line 912 on the y-axis.

For the example experimental data used to generate the exercise period summary data points 906, 908, and 910, the regression line 912 may have the form: y=39.62x−5112.13, with an $r^2$ value of 0.99999. It is noted that this regression line 912 formula is merely included as one example result, and may not correspond to the example values discussed above for exercise period summary data points 906, 908, and 910.

In one example, a regression line, such as regression line 912, through two or more exercise period summary data points, such as the exercise period summary data points 906, 908, and 910, may be used to calculate a critical muscle oxygenation percentage and/or a total number of muscle oxygenation points above a critical muscle oxygenation percentage (which may be proportional to an anaerobic work capacity) for a user. In one example, given regression line 912 of the form: y=mx+c, the critical muscle oxygenation percentage may be equal to m, the slope of the regression line 912, and the total number of muscle oxygenation points above the critical muscle oxygenation percentage may be equal to c (or |c|, the absolute value of c), the intercept of the regression line 912 on the y-axis. In particular, given the experimental data depicted in chart 900, the critical muscle oxygenation percentage for the user may be 39.62%, and the total number of muscle oxygenation points above the critical muscle oxygenation percentage may be 5112.13.

In another example, the regression line 912 may be calculated through a plurality of exercise period summary data points greater than the three exercise period summary data points 906, 908, 910 depicted in FIG. 9A. Further, any methodology known in the art for calculation of a linear regression may be utilized with these disclosures to calculate a regression line 912. Additionally, while FIG. 9A graphically depicts a regression line 912, the activity monitoring device 700 may be configured to calculate a critical muscle oxygenation percentage for a user and/or a total number of muscle oxygenation points above a critical muscle oxygenation percentage, without requiring that a regression line be plotted. I.e. the activity monitoring device 700 may calculate one or more of a critical muscle oxygenation percentage and/or a total number of muscle oxygenation points above a critical muscle oxygenation percentage from muscle oxygenation data outputted from the muscle oxygenation sensor 710 without calculating and/or plotting a regression line through exercise period summary data points. As such, the depiction of regression line 912 may a pictorial description of methodology used by the activity monitoring device 700; however the activity monitoring device 700 may utilize alternative computational processes to calculate the same resulting critical muscle oxygenation percentage and/or total number of muscle oxygenation points above the critical muscle oxygenation percentage.

Figure 9B:
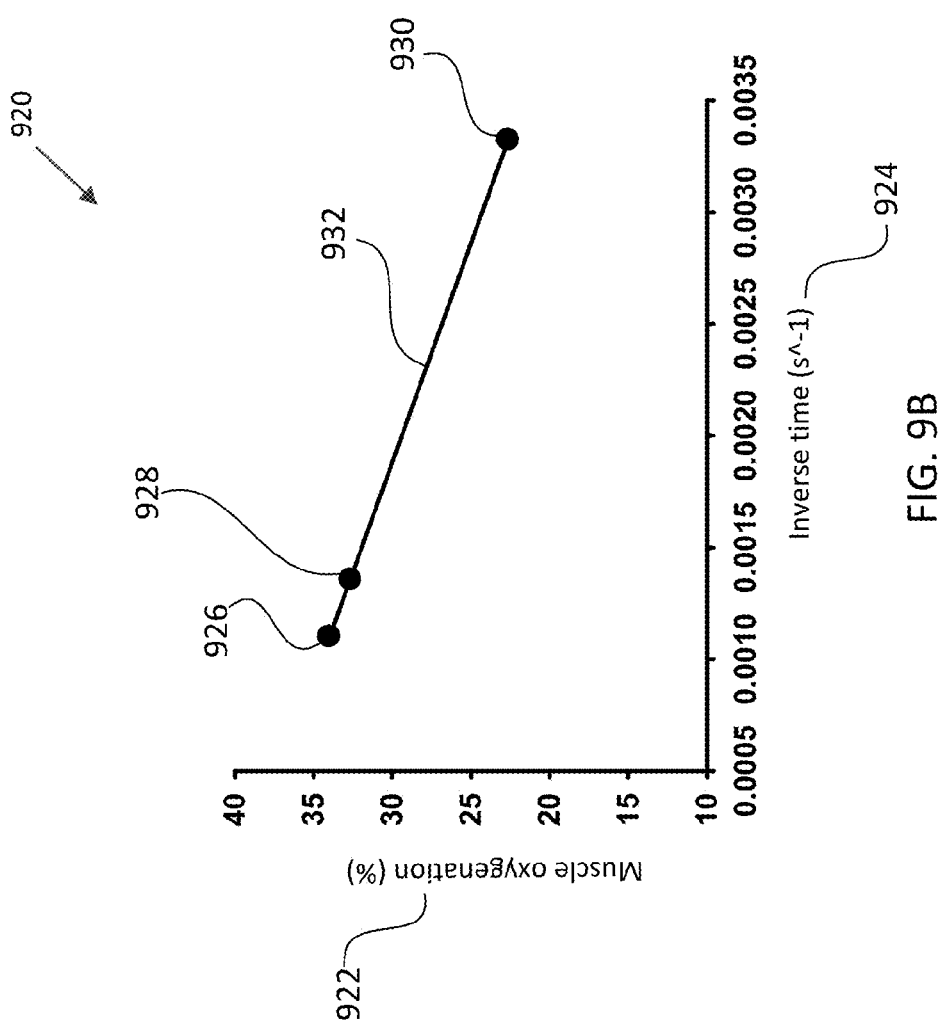

FIG. 9B depicts a chart 920 plotting test data from multiple exercise periods for a same user. In particular, FIG. 9B depicts chart 920 plotting muscle oxygenation percentage (%) 922 against inverse time ($s^{-1}$) 924. In one example, the data points 926, 928, and 930 may each represent a separate exercise session. In one implementation, a data point, from the data points 926, 928, 930, may be of the form ($x_2$,$y_2$), where $y_2$ is an average muscle oxygenation percentage over a total exercise session, and is calculated, in one example, as a sum of muscle oxygenation percentages for each second of an exercise period (in seconds), divided by the duration of the exercise period (in seconds). Those of ordinary skill in the art will recognize that the time resolution (or sampling rate) utilized may be different than the one second resolution described herein, without departing from the scope of these disclosures. For example, $y_2$ may be calculated, in another example, as a sum of muscle oxygenation percentages for each half second interval an exercise period divided by the total number of half seconds in the exercise period, among many other resolutions. Accordingly, $x_2$ may be calculated as 1/(total duration of a given exercise period), giving a result as an inverse time, with units of seconds$^{-1}$ ($s^{-1}$). In one specific implementation, data point 926 may include the same information as exercise period summary data point 910. Similarly, data point 928 may include the same information as exercise period summary data point 908, and data point 930 may include the same information as exercise period summary data point 906.

In one implementation, a regression line 932 may be calculated using two or more data points, such as data points 926, 928, 930. In one example, the regression line 932 may be of the form:

$$y=m_b x+c_b$$

where y is a muscle oxygenation percentage (%) (y-axis), x is an inverse time ($s^{-1}$) (x-axis), $m_b$ is the slope of the regression line 932, and $c_b$ is the intercept of the regression line 932 on the y-axis.

In one example, for the specific data depicted in chart 920, the regression line 932 may have the form: y=−5102.35x+ 39.6, with an $r^2$ value of 0.99999. Accordingly, $m_b$, the slope of the regression line 932 (or $|m_b|$ the absolute value), may equal the number of muscle oxygenation points above a critical muscle oxygenation percentage for a user. Similarly, c, the intercept may be equal to the critical muscle oxygenation percentage for the user.

Figure 10:
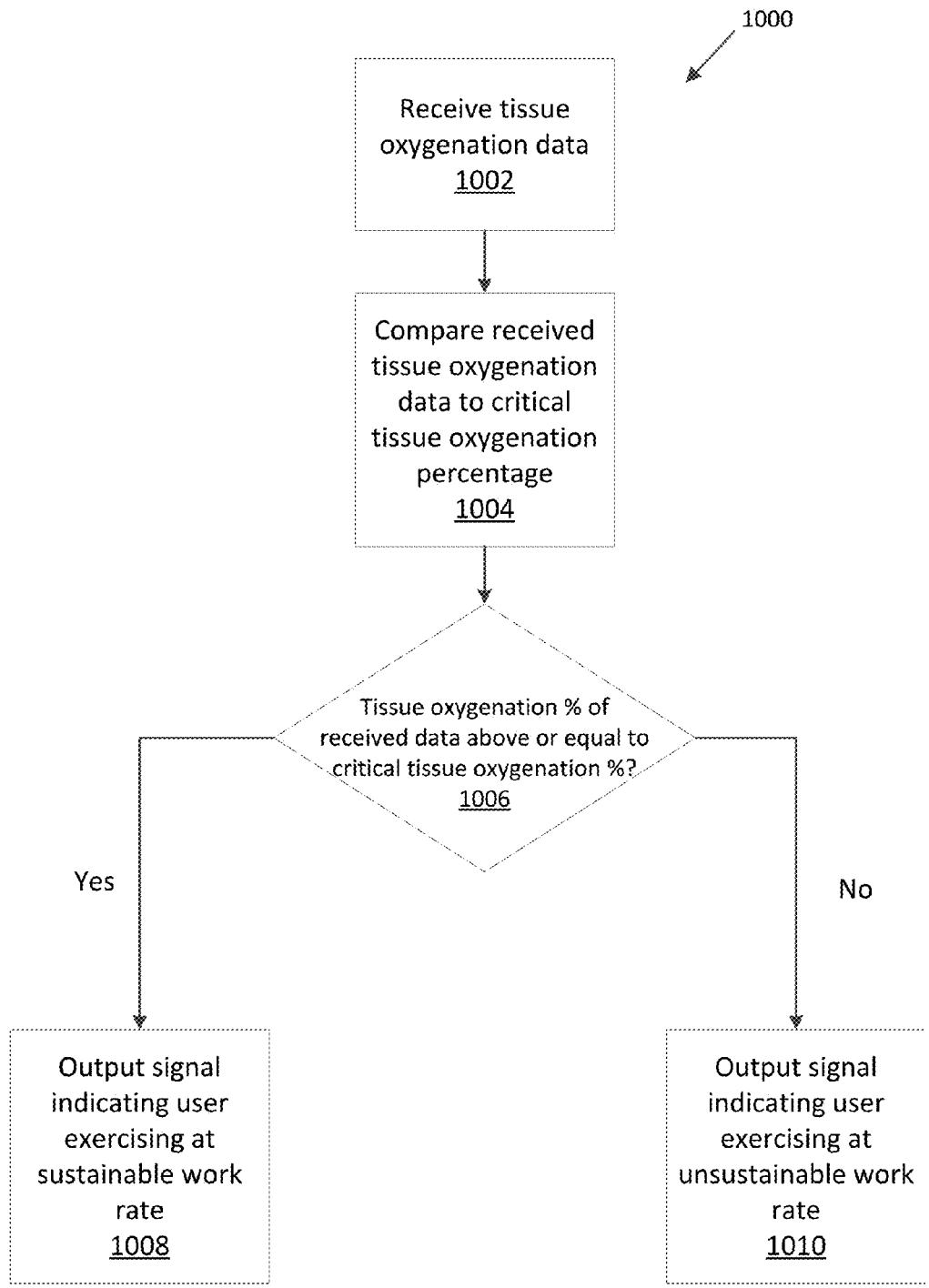
FIG. 10 depicts a flowchart diagram for determination as to whether a user is exercising at an unsustainable work rate within a severe exercise intensity domain, according to one or more aspects described herein.

FIG. 10 is a flowchart diagram 1000 that may be utilized to determine whether a user is exercising at an unsustainable work rate within a severe exercise intensity domain. In one implementation, an activity monitoring device, such as device 700, may receive tissue oxygenation data indicative of a real-time tissue oxygenation percentage for the user while exercising. Accordingly, this tissue oxygenation data may be generated by, in one example, muscle oxygenation sensor 710. As such, one or more processes may be executed by, in one example, processor 702, to receive the tissue oxygenation data. These one or more processes to receive the tissue oxygenation data may be executed at block 1002 of flowchart 1000.

In one implementation, received tissue oxygenation data may be compared to a critical tissue oxygenation percentage for the user. As such, a critical oxygenation percentage for a user may be calculated by an activity monitoring device, such as processor 702 of device 700, and stored memory, such as memory 704. Further, the critical muscle oxygenation percentage for a user may be calculated using one or more processes described in relation to FIG. 8. In one example, the received tissue oxygenation data may be compared to the critical tissue oxygenation percentage for the user by processor 702. As such, one or more processes executed by processor 702 to compare the received tissue oxygenation data to the critical tissue oxygenation percentage for the user may be executed at block 1004 of flowchart 1000.

A comparison of received tissue oxygenation data to a critical tissue oxygenation percentage for a user may include a determination as to whether the received, real-time tissue oxygenation percentage is above or equal to the critical tissue oxygenation percentage. This determination may represented by decision block 1006 of flowchart 1000. Accordingly, if the received tissue oxygenation data represents a tissue oxygenation percentage that is equal to or above a critical tissue oxygenation percentage for the user, the activity monitoring device 700 may output a signal indicating that the user is exercising at a sustainable work rate. In one example, this output signal may be communicated to a user via one or more indicator lights, a user interface, an audible signal, or a haptic feedback signal, among others. As such, the output signal may be communicated through interface 708 of the activity monitoring device 700. In one example, the one or more processes executed to output a signal indicating that the user is exercising at a sustainable work rate (i.e. outside of a severe exercise intensity domain) may be executed at block 1008 of flowchart 1000. In one implementation, if the received tissue oxygenation data represents a tissue oxygenation percentage that is below a critical tissue oxygenation percentage for the user, the activity monitoring device 700 may output a signal indicating that the user is exercising at an unsustainable work rate. In one example, this output signal may be delivered in a similar manner to the output signal described in relation to block 1008. Further, the one or more processes executed to output a signal indicating that the user is exercising at an unsustainable work rate (i.e. within a severe exercise intensity domain) may be executed at block 1010 of flowchart 1000.

Figure 11:
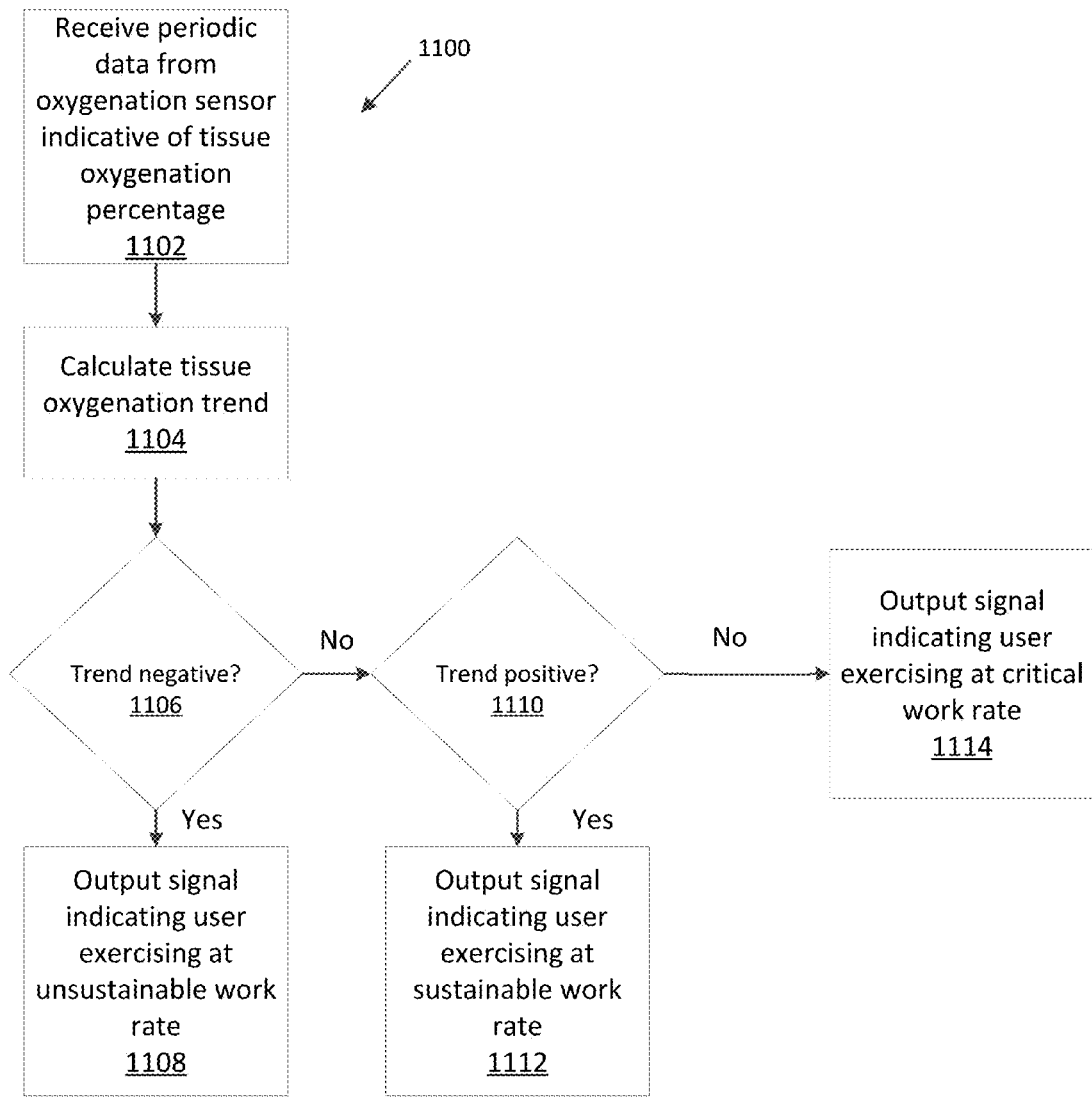
FIG. 11 depicts a flowchart diagram for determination as to whether a user is exercising at an unsustainable, a sustainable, or a critical work rate, according to one or more aspects described herein.

FIG. 11 is a flowchart diagram 1100 that may be utilized to determine if a user is exercising at an unsustainable, a sustainable, or a critical work rate. In one implementation, an activity monitoring device, such as device 700, may receive periodic data from a tissue oxygenation sensor, such as sensor 710, indicative of a real-time oxygenation percentage of a tissue of a user while exercising. Accordingly, tissue oxygenation percentage data may be received by, in one example, processor 702, from sensor 710, and with a periodicity of one sample per second (1 Hz). In another implementation, the sensor 710 may output a data point indicative of a tissue oxygenation percentage once every two seconds (0.5 Hz), once every three seconds (0.33 Hz), or once every four seconds (0.25 Hz), among others. Further, tissue oxygenation data may be generated by, and received from, the sensor 710 at any rate, without departing from the scope of these disclosures. In one example, one or more processes may be executed to receive, by a processor, such as processor 702, periodic data from a tissue oxygenation sensor indicative of a tissue oxygenation percentage at block 1102 of flowchart 1100.

In one implementation, tissue oxygenation data received from a tissue oxygenation sensor, such as sensor 710, may be stored in memory, such as memory 704. Accordingly, in one example, a trend in tissue oxygenation data may be calculated based upon a comparison of a most recently-received tissue oxygenation percentage data point to one or more previously-stored tissue oxygenation percentage data points. In one example, one or more processes may be executed by processor 702 of the activity monitoring device 700, to calculate a change in tissue oxygenation percentage over a time spanning between a saved tissue oxygenation percentage data point, and a most recently-received tissue oxygenation percentage data point. In one implementation, this change may be calculated as a positive number, which may be indicative of an increase in tissue oxygenation percentage, as the negative number, which may be indicative of a decrease in tissue oxygenation percentage, or as a zero value, which may be indicative of no change in tissue oxygenation percentage. In another implementation, one or more processes may be executed by processor 702 of the activity monitoring device 700 to calculate a trend in tissue oxygenation percentage as a slope of a regression line, and calculated using two or more tissue oxygenation percentage data points. As such, if the slope of the calculated line has a negative value, it may be indicative of a decrease in tissue oxygenation percentage. Similarly, if the slope of the line is calculated as having a positive value, it may be indicative of an increase in tissue oxygenation percentage, and if the slope of the line is calculated as having a zero value, it may be indicative of no change in tissue oxygenation. In one example, one or more processes for calculation of a tissue oxygenation trend may be executed at block 1104 of flowchart 1100.

Figure 15:
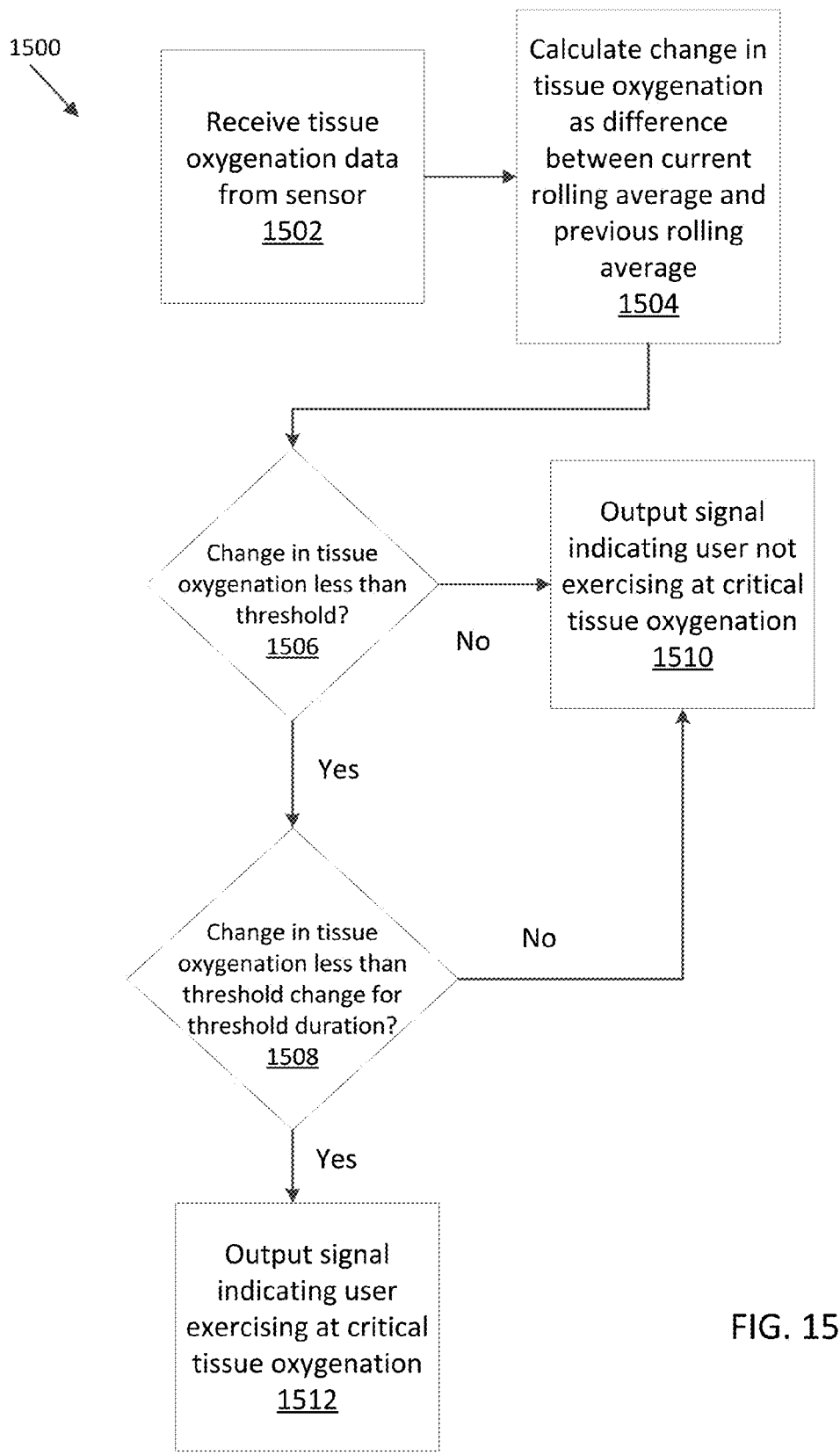
FIG. 15 depicts a flowchart diagram for determination as to whether the received tissue oxygenation data represents exercise at a critical intensity, according to one or more aspects described herein.

In additional or alternative implementations, a trend in tissue oxygenation may be calculated, such as at block 1104, according to the one or more processes described in relation to FIG. 15.

Decision block 1106 may represent one or more processes executed by processor 702 to determine if the calculated tissue oxygenation trend from block 1104 represents a negative trend. Accordingly, if it is determined that the calculated tissue oxygenation trend is negative, flowchart 1100 may proceed to block 1108. In one implementation, upon determining that data received from a tissue oxygenation sensor is representative of a negative trend, one or more processes may be executed to output a signal indicating that the user may be exercising at an unsustainable work rate. As such, one or more processes configured to output a signal indicating that the user may be exercising at an unsustainable work rate may be executed at block 1108. In another implementation, if it is determined that data received from a tissue oxygenation sensor is not representative of a negative trend, flowchart 1100 may proceed to decision block 1110. Accordingly, decision block 1110 may be associated with one or more processes executed to determine whether the calculated tissue oxygenation trend is positive. If it is determined that the calculated tissue oxygenation trend is positive, flowchart 1100 may proceed to block 1112. Accordingly, in one example, if it is determined that the calculated tissue oxygenation trend is positive, a signal may be outputted to indicate that the user is exercising at a sustainable work rate. In one example, the output signal indicating that the user is exercising at a sustainable work may be executed at block 1112 of flowchart 1100. In another example, if it is determined that the calculated tissue oxygenation trend is not positive, flowchart 1100 may proceed to block 1114. In this way, it may be determined that the calculated tissue oxygenation trend is approximately level (unchanged). As such, a level tissue oxygenation trend may be indicative of a user exercising at a critical work rate. Accordingly, in response to determining that the tissue oxygenation trend is approximately level, one or more processes may be executed to output a signal indicating that the user is exercising at a critical work rate. In one implementation, these one or more processes may be executed at block 1114 of flowchart 1100.

It is noted that flowchart 1100 may calculate a tissue oxygenation trend from two or more data points indicative of muscle oxygenation percentages at two or more different time points. As such, any numerical methodology known in the art may be utilized to calculate a trend between two or more such points, including, among others, calculation of a slope of a line connecting two points, or calculation of a regression line using a plurality of points, among others.

Figure 12:
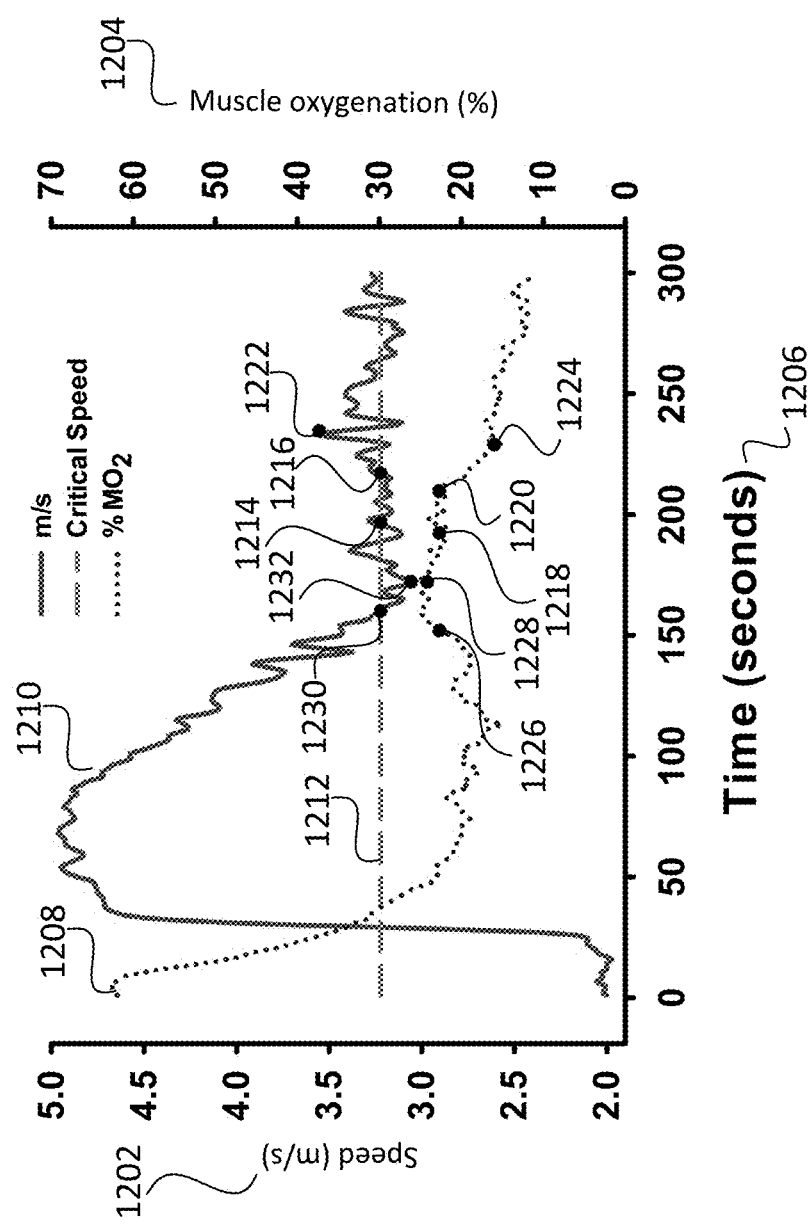
FIG. 12 depicts graphs of speed and muscle oxygenation output data generated during an exercise session, according to one or more aspects described herein.

FIG. 12 depicts two graphs of data generated during a same exercise session. The two depicted graphs include muscle oxygenation percentage data 1208 and running speed data 1210 plotted against a common timescale 1206. In one implementation, the muscle oxygenation percentage data 1208 may be generated by a muscle oxygenation sensor, such as sensor 710. Further, the running speed data 1210 may be calculated based on sensor data generated by sensor 706, which may include, among others, an accelerometer, or a location-determining sensor. Accordingly, the graph of running speed 1210 may be associated with scale 1202, and the graph of muscle oxygenation 1208 may be associated with scale 1204. In one example, graphs 1208 and 1210 schematically depict relationships between muscle oxygenation percentage and a running speed. In one example, the period between points 1218 and 1220 on the muscle oxygenation percentage graph 1208 may represent a substantially level trend in muscle oxygenation percentage. Accordingly, points 1214 and 1216 on the speed graph 1210 may correspond to points 1218 and 1220, and such that the approximately level trend in muscle oxygenation percentage between points 1218 and 1220 corresponds to a critical speed, as schematically indicated by line 1212. In another example, a substantially negative trend in muscle oxygenation percentage between points 1220 and 1224 on the muscle oxygenation graph 1208 may correspond to an increase in speed above the critical speed between points 1216 and 1222 on the speed graph 1210. In yet another example, a positive trend in muscle oxygenation between points 1226 and 1228 on the muscle oxygenation graph 1208 may correspond to a decrease in speed below a critical speed between points 1230 and 1232 on the speed graph 1210.

Figure 13:
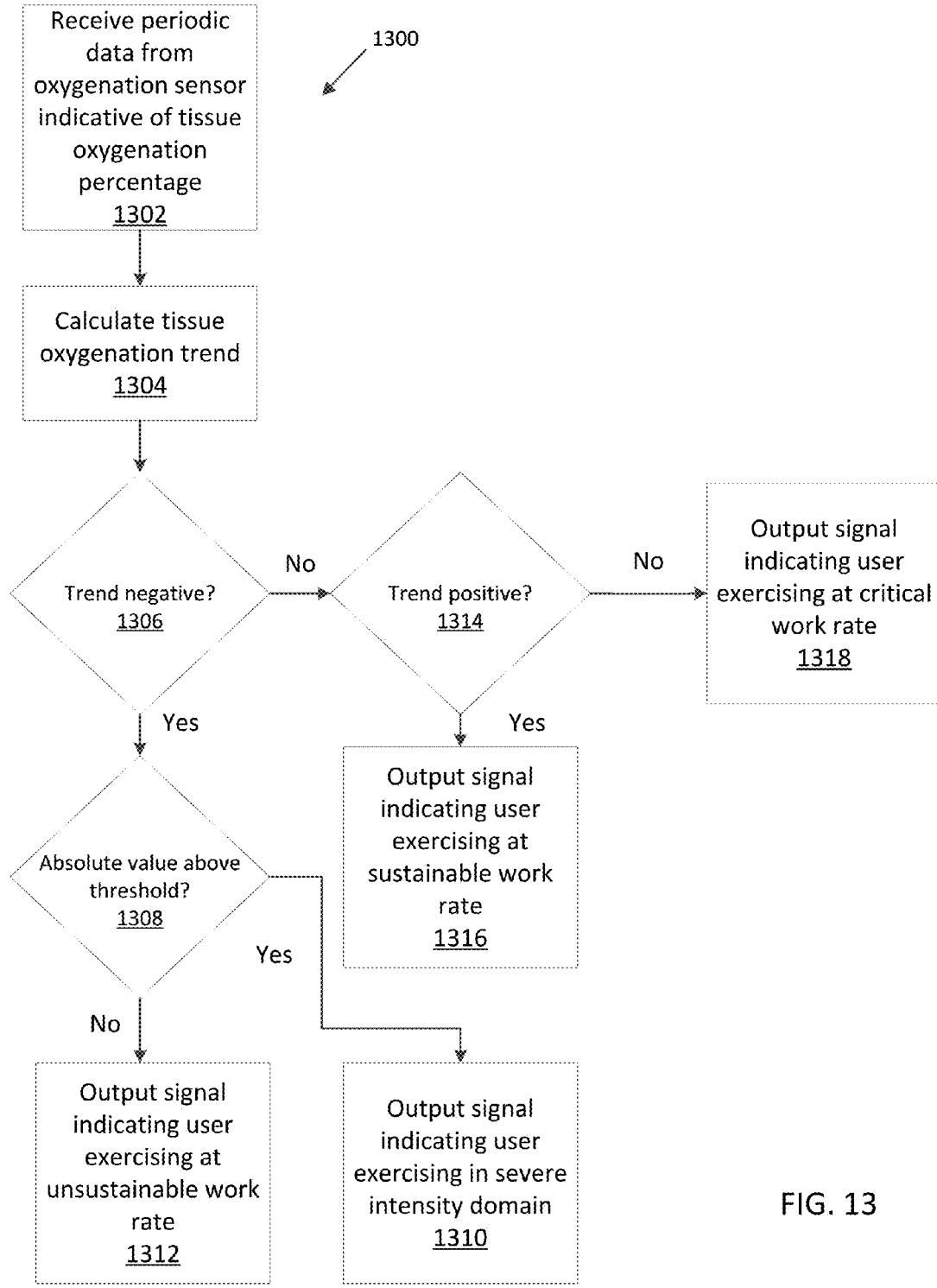
FIG. 13 depicts a flowchart diagram for determination as to whether a user is exercising within a severe exercise intensity domain, according to one or more aspects described herein.

FIG. 13 is a flowchart diagram 1300 that may be utilized to determine if a user is exercising within a severe exercise intensity domain. In one implementation, an activity monitoring device, such as device 700, may receive periodic data from a tissue oxygenation sensor, such as sensor 710, indicative of a real-time oxygenation percentage of a tissue of a user while exercising. Accordingly, tissue oxygenation percentage data may be received by, in one example, processor 702, from sensor 710, and with a periodicity of one sample per second (1 Hz). In another implementation, the sensor 710 may output a data point indicative of a tissue oxygenation percentage once every two seconds (0.5 Hz), once every three seconds (0.33 Hz), once every four seconds (0.25 Hz), among others. Further, tissue oxygenation data may be generated by, and received from, the sensor 710 at any rate, without departing from the scope of these disclosures. In one example, one or more processes may be executed to receive, by a processor, such as processor 702, periodic data from a tissue oxygenation sensor indicative of a tissue oxygenation percentage at block 1302 of flowchart 1300.

In one implementation, tissue oxygenation data received from a tissue oxygenation sensor, such as sensor 710, may be stored in memory, such as memory 704. Accordingly, in one example, a trend in tissue oxygenation data may be calculated based upon a comparison of a most recently-received tissue oxygenation percentage data point, to one or more previously-stored tissue oxygenation percentage data points. In one example, one or more processes may be executed by processor 702 of the activity monitoring device 700 to calculate a change in tissue oxygenation percentage over a time spanning between a saved tissue oxygenation percentage data point, and a most recently-received tissue oxygenation percentage data point. In another implementation, one or more processes may be executed by processor 702 of the activity monitoring device 700 to calculate a trend in tissue oxygenation percentage as a slope of a regression line calculated using two or more tissue oxygenation percentage data points. In one example, one or more processes for calculation of a tissue oxygenation trend may be executed at block 1304 of flowchart 1300.

Decision block 1306 may represent one or more processes executed by processor 702 to determine if the calculated tissue oxygenation trend from block 1304 represents a negative trend. Accordingly, if it is determined that the calculated tissue oxygenation trend is negative, flowchart 1300 may proceed to decision block 1308. In one implementation, decision block 1308 may execute one or more processes to calculate an absolute value of a negative trend (negative slope) identified at decision block 1306. Additionally, decision block 1308 may represent one or more processes configured to compare the absolute value of the negative trend to a threshold value. In one example, if the absolute value is above a threshold value, flowchart 1300 may proceed to block 1310. Accordingly, the threshold value may comprise any value, without departing from the scope of these disclosures. In one example, upon determining that the absolute value is above a threshold value, one or more processes may be configured to output a signal indicating that the user is exercising in a severe intensity domain. As such, these one or more processes configured to output a signal indicating that the user is exercising within a severe intensity domain may be executed at block 1310. If, however, the absolute value is below a threshold, flowchart 1300 may proceed to block 1312. Accordingly, block 1312 may comprise one or more processes that may be executed to output a signal indicating that the user is exercising at an unsustainable work rate.

In another implementation, if it is determined that data received from a tissue oxygenation sensor is not representative of a negative trend, flowchart 1300 may proceed to decision block 1314. Accordingly, decision block 1314 may be associated with one or more processes executed to determine whether the calculated tissue oxygenation trend is positive. If it is determined that the calculated tissue oxygenation trend is positive, flowchart 1300 may proceed to block 1316. Accordingly, in one example, if it is determined that the calculated tissue oxygenation trend is positive, a signal may be outputted to indicate that the user is exercising at a sustainable work rate. In one example, the output signal indicating that the user is exercising at a sustainable work may be executed at block 1316 of flowchart 1300. In another example, if it is determined that the calculated tissue oxygenation trend is not positive, flowchart 1300 may proceed to block 1318. In this way, it may be determined that the calculated tissue oxygenation trend is approximately level (unchanged). As such, a level tissue oxygenation trend may be indicative of a user exercising at a critical work rate. Accordingly, in response to determining that the tissue oxygenation trend is approximately level, one or more processes may be executed to output a signal indicating that the user is exercising at a critical work rate. In one implementation, these one or more processes may be executed at block 1318 of flowchart 1300.

Figure 14A:
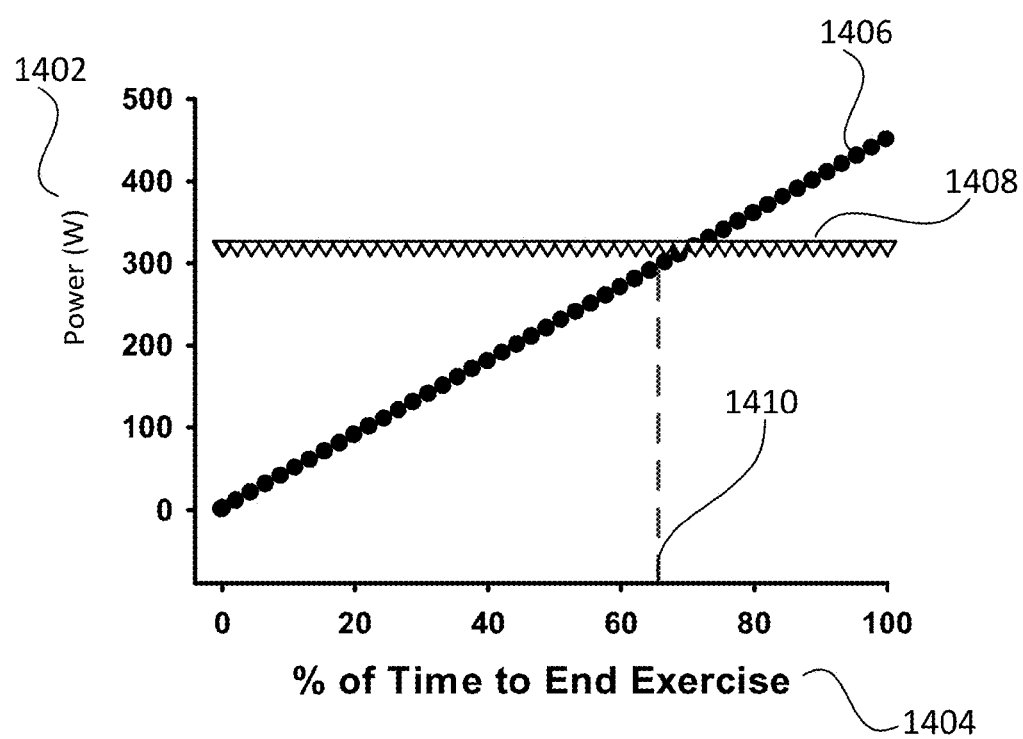
FIGS. 14A-14B depict graphs of power and muscle oxygenation output data from two exercise sessions, according to one or more aspects described herein.

FIG. 14A depicts two graphs plotted using data from two separate exercise sessions participated in by a same user. In particular, graph 1406 comprises output data from a ramped work rate exercise session. In one example, work rate (W) may be depicted on the y-axis 1402. Accordingly, the data associated with graph 1406 may be generated from data outputted during an exercise session that prescribes a linearly-increasing work rate that increases from a work rate below a critical intensity, to a work rate above a critical intensity for the user. Graph 1408 may be generated from data outputted during an exercise session that prescribes a constant work rate. In one example, the constant work rate associated with graph 1408 may be approximately 15% above a critical intensity for the user. Accordingly, the exercise session associated with graph 1408 may be within a severe exercise intensity domain for the user. In one example, the x-axis 1404 represents a percentage of time to the end of an exercise session. Further, point 1410 represents an approximate time at which the ramped work rate exercise session reaches the critical intensity for the user.

Figure 14B:
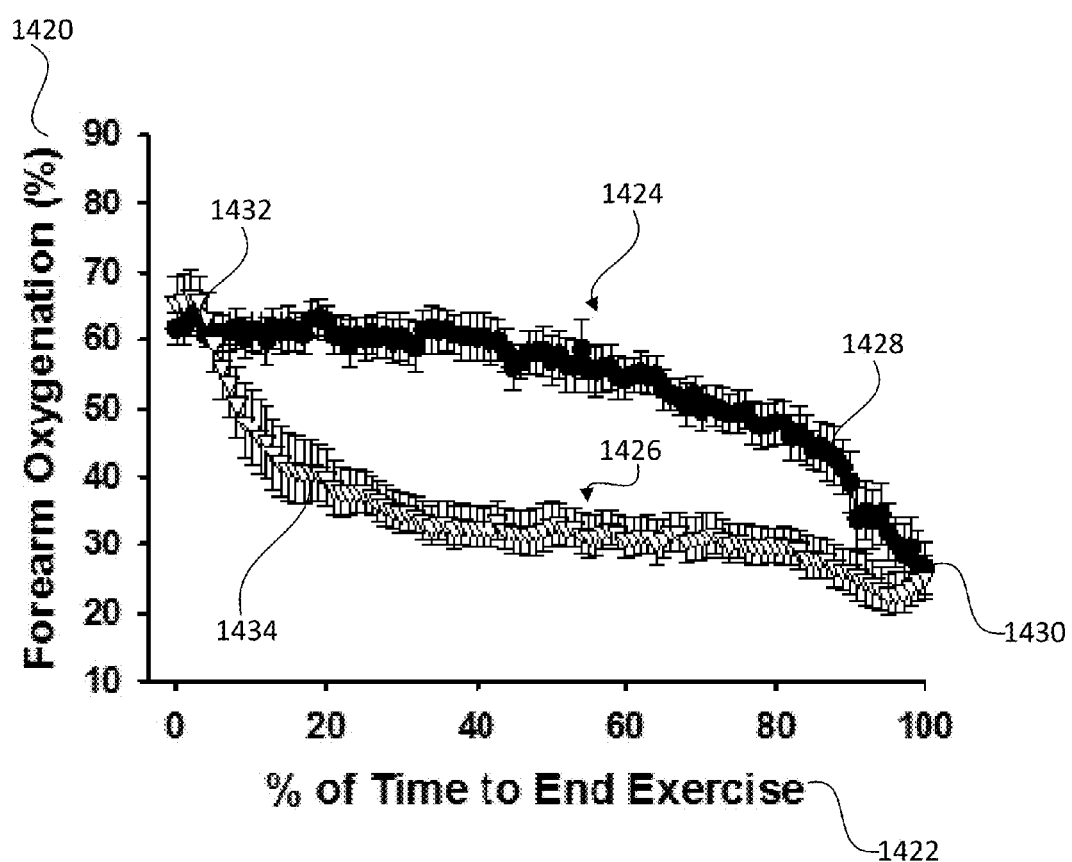

FIG. 14B depicts two graphs plotted using data from the same two separate exercise sessions from FIG. 14A. In particular, graph 1424 may correspond to the ramped work rate exercise session associated with graph 1406. Additionally, graph 1426 may correspond to the constant work rate exercise session associated with graph 1408. In one example, graphs 1424 and 1426 may be plotted as tissue oxygenation percentage on a y-axis 1420 versus percentage of time to an end of exercise session on an x-axis 1422. In one example, graphs 1406, 1408, 1424, and 1426 may share a common x-axis scale.

In one implementation, graph 1426, which is plotted using data from a constant work rate exercise session with a constant work rate at approximately 15% above a critical intensity for the user, may exhibit a steep slope between points 1432 and 1434 at the beginning of the exercise session (i.e. between approximately 0 and 20% of the time to the end of the exercise session). However, a graph 1426 may transition to a shallower slope between points 1434 and 1430 as the constant work rate exercise session is completed.

In one example, graph 1424, which may commence at a work rate below a critical intensity, may exhibit a shallower slope between points 1432 and 1428. Accordingly, point 1428 may approximately correspond to a point at which the ramped exercise intensity session associated with graph 1406 reaches the critical intensity for the user (i.e. transitions from a heavy to a severe exercise intensity domain for the user). As such, a slope of the graph 1424 may steepen between points 1428 and 1430.

Accordingly, in one example, a slope of graph 1424 between points 1428 and 1430 may represent a slope with absolute value above a threshold value, said threshold value corresponding to a critical intensity for the user. In one example, a slope of graphs 1424 between points 1428 and 1430 may be approximately equal to a slope of graph 1426 between points 1432 and 1434.

FIG. 15 is a flowchart diagram 1500 that may be executed as one or more processes, such as by device 700, to determine if received tissue oxygenation data represents exercise by a user at a critical intensity. In one example, tissue oxygenation data may be received from a sensor, such as sensor 710 associated with the device 700. As such, the tissue oxygenation data may correspond to muscle oxygenation, and may be expressed as muscle oxygenation percentages. Accordingly, one or more processes may be executed to receive tissue oxygenation data from a sensor at block 1502 of process 1500. Further, tissue oxygenation data may be received from a sensor, such as sensor 710, with any periodicity, or at non-periodic intervals, without departing from the scope of these disclosures. In one implementation, data received from a tissue oxygenation sensor at block 1502 may be stored in memory, such as memory 704.

In one example, a change in tissue oxygenation may be calculated as a difference between a current rolling average and a previous rolling average of tissue oxygenation. Accordingly, a current rolling average may be calculated as an average value of tissue oxygenation percentage over a first duration, whereby the current rolling average may include a most-recently received sensor data point. In another implementation, a current rolling average may be calculated as an average value of tissue oxygenation percentage over a predetermined number of received sensor data points (which may be received with a periodicity, or non-periodically). In certain specific examples, a current rolling average may be calculated as an average muscle oxygenation percentage for those muscle oxygenation percentage data points received during the past five seconds, including a most-recently received data point. However, alternative times for the first duration may be utilized, without departing from the scope of these disclosures. For example, the first duration may be one second, two seconds, three seconds, four seconds, and six seconds, seven seconds, eight seconds, nine seconds, ten seconds, or any other duration. Further, the previous rolling average may be calculated as an average value of tissue oxygenation percentage over a second duration, whereby the previous rolling average does not include the most-recently received sensor data point (i.e. may include at least all the data points used to calculate the current rolling average, except the most-recently received sensor data point). In one example, the previous rolling average may be calculated for a second duration, equal to the first duration. In one implementation, the difference between the present rolling average, and the previous rolling average may be calculated by subtraction, thereby resulting in a percentage muscle oxygenation difference. In one implementation, one or more processes utilized to calculate a change in tissue oxygenation may be executed at block 1504 of process 1500, and by, in one example, processor 702.

In order to determine whether a calculated change in tissue oxygenation corresponds to a critical tissue oxygenation (critical intensity) for a given user, the calculated change in tissue oxygenation may be compared to a threshold value. In one example, this threshold value of change in tissue oxygenation percentage may include any oxygenation value. In one specific example, the threshold value of change in tissue oxygenation percentage may be less than 0.1 (i.e. the received tissue oxygenation percentage may not correspond to a critical tissue oxygenation percentage unless a difference between a current rolling average of tissue oxygenation percentage and a previous rolling average is less than 0.1 (units of tissue oxygenation percentage)). In another example, the received tissue oxygenation percentage may not correspond to a critical tissue oxygenation percentage unless a difference between a current rolling average of tissue oxygenation percentage and a previous rolling average is less than or equal to 0.1 (units of tissue oxygenation percentage). Additional or alternative tissue oxygenation thresholds may include 0.2, 0.3, 0.4, 0.5, 0.6 among others. In one example, one or more processes may be executed to determine whether a change in tissue oxygenation is less than a threshold at decision block 1506 of process 1500.

If it is determined that a calculated change in tissue oxygenation is greater than or equal to a threshold value (or in another implementation, if it is determined that a calculated change in tissue oxygenation is greater than to a threshold value), one or more processes may be executed to output a signal indicating that the user is not exercising at a critical tissue oxygenation. Accordingly, these one or more processes may be executed at block 1510, and by a processor, such as processor 702. If, however, it is determined that the calculated change in tissue oxygenation is less than a threshold value (or in another implementation, less than or equal to the threshold value), flowchart 1500 may proceed to decision block 1508.

Accordingly, decision block 1508 may represent one or more processes executed to determine whether the change in tissue oxygenation (that is less than the previously-described threshold value, or in another implementation, less than or equal to the threshold value) is consistent/steady for a threshold duration (i.e. that the change in tissue oxygenation percentage is less than a threshold change, and for a predetermined threshold duration). Accordingly, any threshold duration may be utilized with these disclosures. In certain specific examples, the threshold duration may be equal to at least one second, at least two seconds, at least three seconds, at least four seconds, at least five seconds, or at least 10 seconds, among others. If it is determined that the calculated change in tissue oxygenation is not consistent for the threshold duration, flowchart 1500 may proceed to block 1510. If, however, it is determined that the calculated change in tissue oxygenation is consistent for the threshold duration, flowchart 1500 may proceed to block 1512.

As such, upon determining that the calculated change in tissue oxygenation is consistent for a threshold duration, one or more processes may be executed to output a signal indicating that a user is exercising at a critical work rate/critical tissue oxygenation (which may be expressed as a tissue oxygenation percentage). These one or more processes configured to output a signal indicating that the user is exercising at a critical work rate may be executed by processor 702. Further, one or more processes may be executed at block 1512 to output a tissue oxygenation percentage corresponding to those received sensor values for which the difference between the current rolling average and previous rolling average is less than the threshold. This tissue oxygenation percentage may be a critical tissue oxygenation percentage for the user.

In one example, there may be variation in a critical muscle oxygenation percentage calculated for a user during different times of a same exercise. Accordingly, in one example, the critical tissue oxygenation percentage outputted at block 1512 may be averaged across multiple separately-calculated critical tissue oxygenation percentages for a same user during an exercise session, among others.

In one implementation, the tissue oxygenation discussed in relation to flowchart 1500, as well as throughout this disclosure, may comprise a muscle oxygenation for any muscle within a user's body. Further, this calculated critical tissue oxygenation percentage value may be utilized to calculate an anaerobic work capacity (M') for the user (in one example, this anaerobic work capacity may be expressed as a total number of muscle oxygenation points), and calculated as a difference between a current muscle oxygenation percentage ($MO_{2\ current}$) (above the critical muscle oxygenation percentage) and the critical muscle oxygenation percentage ($MO_{2\ crit}$), summed over a duration of an exercise session to fatigue:

$$M' = \Sigma_{t=0}^{fatigue}(MO_{2\ current} - MO_{2\ crit})\ \text{(Units: muscle oxygenation points);\ \ (First anaerobic work capacity equation)}$$

Figure 16:
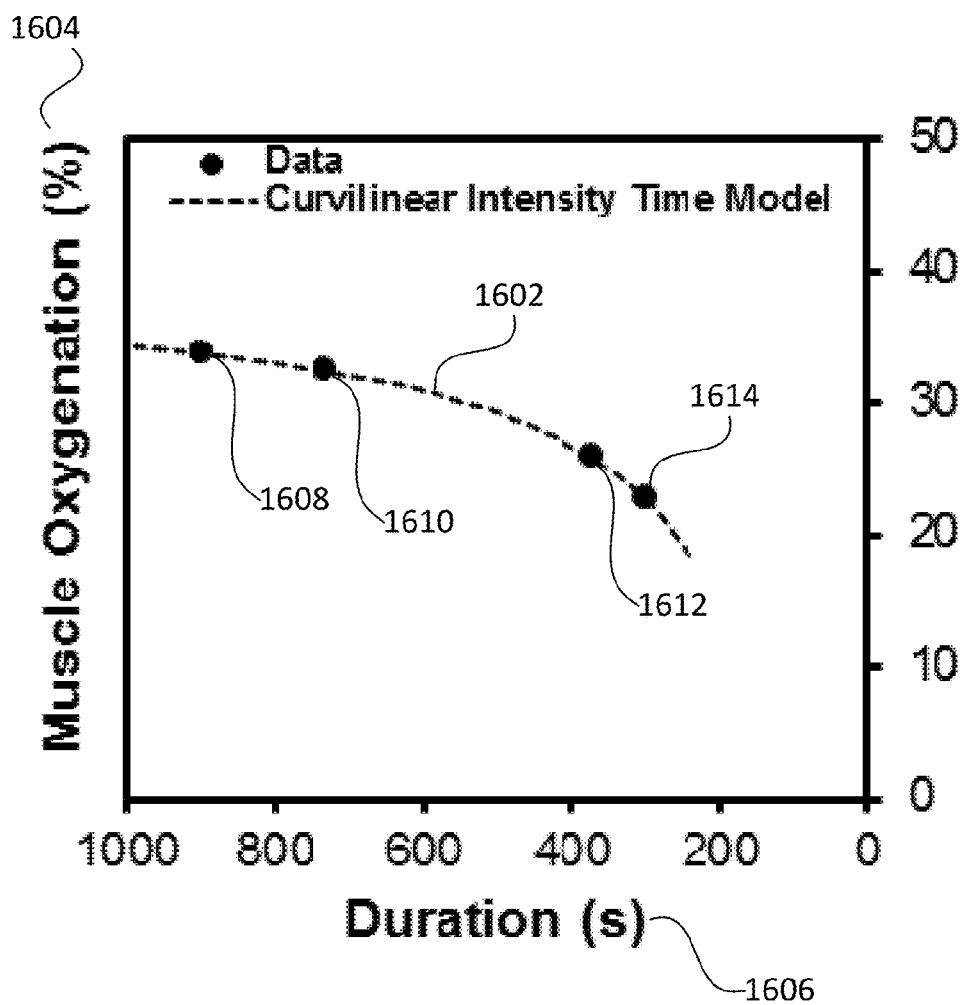
FIG. 16 depicts a graph of muscle oxygenation percentage for different exercise sessions, according to one or more aspects described herein.

FIG. 16 depicts a graph 1602 of muscle oxygenation percentage (%) plotted on the y-axis 1604 versus duration (time) (s) on the x-axis 1606. In one example, graph 1602 comprises data points 1608, 1610, 1612, and 1614, wherein data points 1608, 1610, 1612, and 1614 represent separate exercise sessions. As such, a data point, from data points 1608, 1610, 1612, and 1614, may be associated with a total time of an exercise session, and a muscle oxygenation percentage associated with that exercise session. In one example, this muscle oxygenation percentage may be an average muscle oxygenation over the total time of the exercise session. In another example, this muscle oxygenation percentage may be a muscle oxygenation percentage at the end of the exercise session, among others. In one implementation, graph 1602 displays a trend in muscle oxygenation percentage for different exercise session durations. In particular, graph 1602 may indicate that a comparatively shorter exercise session, such as that exercise session associated with data point 1614, may be associated with a lower muscle oxygenation percentage. This trend may be due to a user exercising at a comparatively higher work rate for a comparatively shorter time. In contrast to a data point 1614, data point 1608 may be associated with a comparatively longer exercise session, and may be associated with a higher muscle oxygenation percentage as a result of a user exercising for a comparatively longer time, and adopting, in one example, a less strenuous pacing strategy in order to conserve energy for the comparatively longer exercise session duration. In one example, graph 1602 may comprise a curvilinear regression plotted through data points 1608, 1610, 1612, and 1614. As such, any processes known in the art may be utilized to construct graph 1610, without departing from these disclosures.

Figure 17:
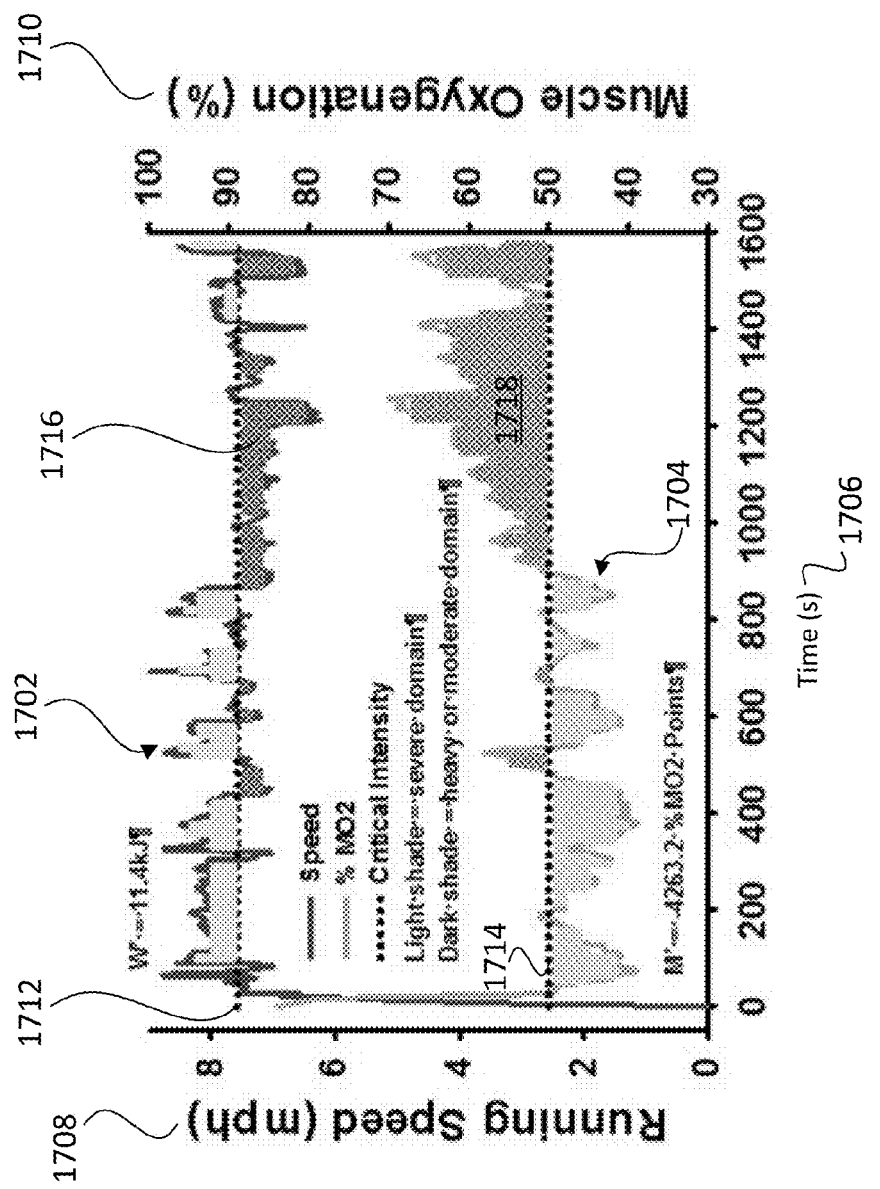
FIG. 17 depicts graphs of speed and muscle oxygenation output data generated during a same exercise session, according to one or more aspects described herein.

FIG. 17 depicts two graphs of data generated during a same exercise session. The two depicted graphs include muscle oxygenation percentage data 1702 and running speed data 1704 plotted against a common timescale 1706. In one implementation, the muscle oxygenation percentage data 1702 may be generated by a muscle oxygenation sensor, such as sensor 710. Further, the running speed data 1704 may be calculated based on sensor data generated by sensor 706, which may include, among others, an accelerometer, or a location-determining sensor. Accordingly, the graph of running speed 1702 may be associated with scale 1708, and the graph of muscle oxygenation 1704 may be associated with scale 1710. In one example, graphs 1702 and 1704 schematically depict relationships between muscle oxygenation percentage and a running speed. In one implementation, given the critical intensity (critical running speed) denoted by line 1712, and the critical intensity (critical muscle oxygenation percentage) denoted by line 1714, a relationship between the speed 1702, and the muscle oxygenation percentage 1704 may be recognized. In particular, when a user's speed is below a critical speed, such as within shaded area 1716, a corresponding muscle oxygenation percentage for the user will be above a critical muscle oxygenation percentage 1714, such as within that shaded area 1718, and vice versa.

Figure 18:
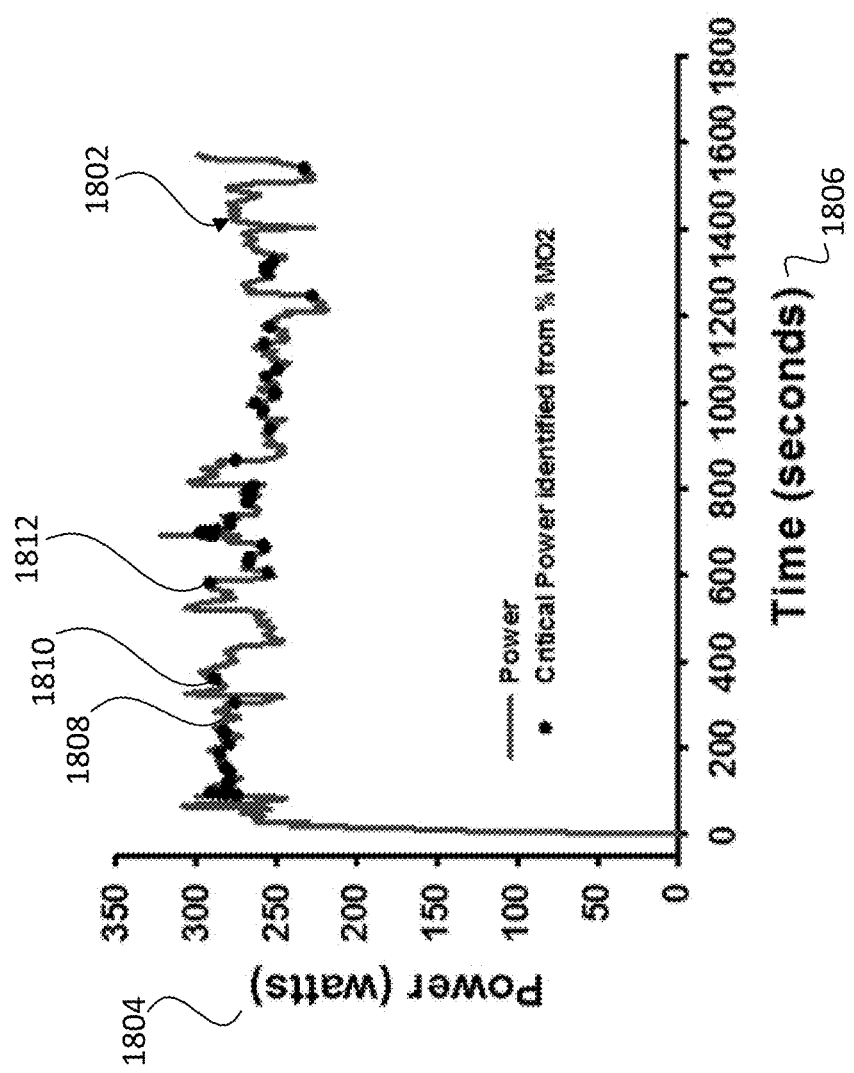
FIG. 18 depicts a graph of power output data from an exercise session, according to one or more aspects described herein.

FIG. 18 depicts a graph 1802 of power on a y-axis 1804 versus time on the x-axis 1806 for an exercise session. As will be readily appreciated, the data associated with FIG. 18 may be derived from any exercise/sport type, without departing from the scope of these disclosures. For example, the graph 1802 may comprise data outputted from a power sensor during a running session, cycling session, tennis game, basketball game, or soccer game, among others. In one example, graph 1802 may comprise power data received by a processor, such as processor 702 of activity monitoring device 700. As such, the activity monitoring device 700 may comprise, or may be configured to communicate with, a power sensor from which power data is directly outputted, or from which power values may be calculated. Accordingly, as described herein, a power sensor may comprise an accelerometer from which acceleration data input may be utilized to calculate a user's speed, and further, a user's rate of energy consumption (power). In another example, a power sensor may comprise a dynamometer that may be operatively coupled to an exercise bike on which a user is exercising, among others.

Figure 19:
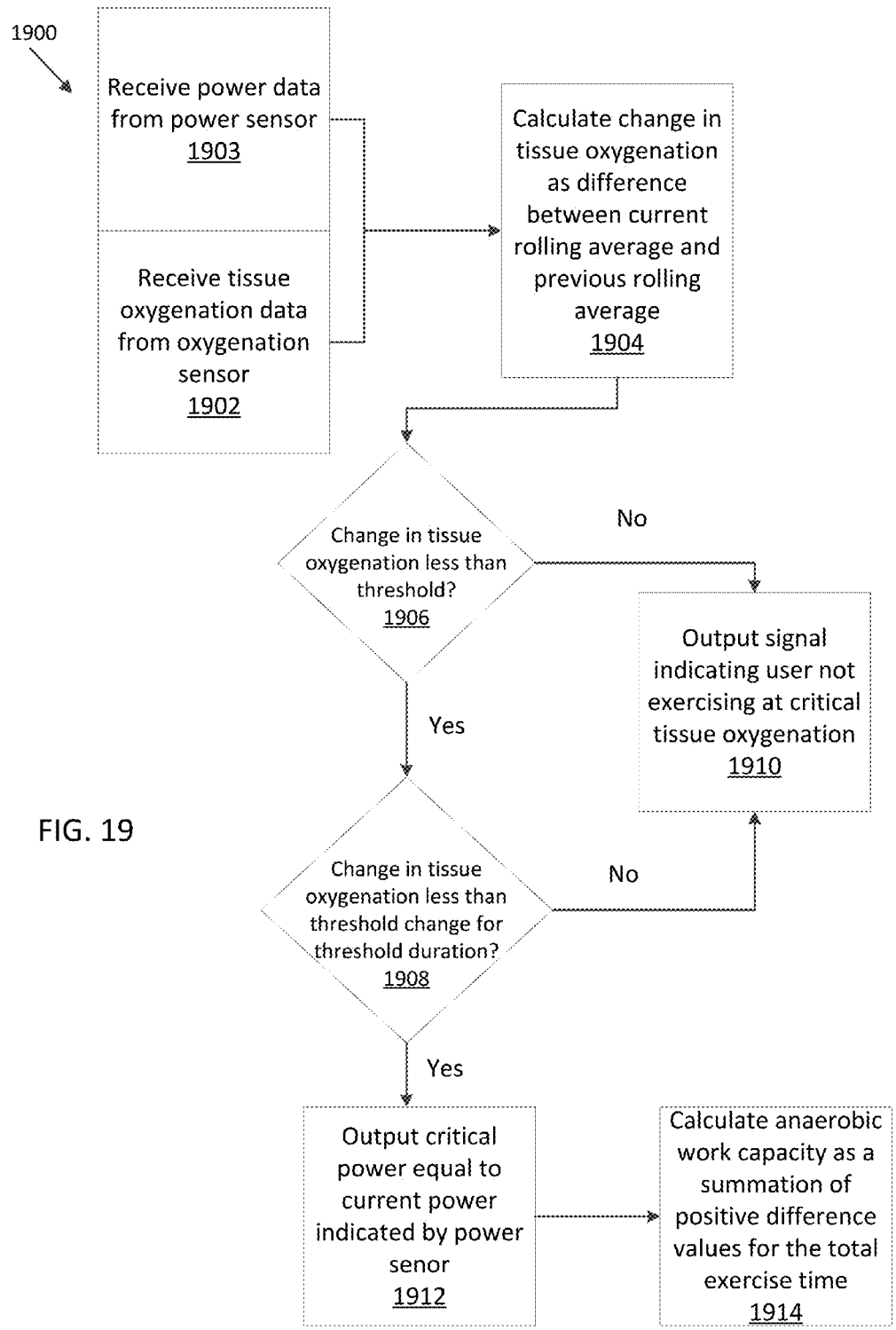
FIG. 19 depicts a flowchart diagram for calculation of a critical power associated with an exercise session, according to one or more aspects described herein.

In one example, the data points 1808, 1810, and 1812 may represent calculated critical power values for the user. Accordingly, in one example, these critical power values may be calculated using one or more processes described in relation to FIG. 19. As such, FIG. 19 depicts a flowchart diagram 1900 that may be executed by activity monitoring device 700. In one implementation, flowchart diagram 1900 may be utilized to calculate a critical power associated with an exercise session undertaken by a user. Further, this exercise session may comprise at least a portion undertaken within a severe exercise intensity domain. In one example, flowchart diagram 1900 may utilize a tissue oxygenation sensor, such as sensor 710, and a power sensor, which may comprise one or more of a dynamometer, or an accelerometer, among others. In one example, the tissue oxygenation sensor may be configured to output data indicative of a tissue oxygenation percentage with a periodicity, or at a non-periodic rate. Accordingly, a periodicity with which the tissue oxygenation sensor outputs data points indicative of a tissue oxygenation percentage may have any value, without departing from the scope of these disclosures. Further, the activity monitoring device 700 may execute one or more processes to receive tissue oxygenation data at block 1902 of flowchart 1900. The activity monitoring device 700 may, in one example, execute one or more processes to receive power data from a sensor, at block 1903 of flowchart 1900.

A change in tissue oxygenation may be calculated as a difference between a current tissue oxygenation value and a previous tissue oxygenation value. Accordingly, in one implementation, the current tissue oxygenation value may correspond to a rolling average, and similarly, the previous tissue oxygenation value may correspond to a previous rolling average of tissue oxygenation. As such, the current rolling average may be calculated as an average value of tissue oxygenation percentage over a first duration, whereby the current rolling average may include a most-recently received sensor data point. In another implementation, a current rolling average may be calculated as an average value of tissue oxygenation percentage over a predetermined number of received sensor data points (which may be received with a periodicity, or at a non-periodic rate). In certain specific examples, a current rolling average may be calculated as an average muscle oxygenation percentage for those muscle oxygenation percentage data points received during the past five seconds, including a most-recently received data point. However, alternative times for this first duration may be utilized, without departing from the scope of these disclosures. For example, the first duration may be at least one second, two seconds, three seconds, four seconds, and six seconds, seven seconds, eight seconds, nine seconds, ten seconds. In another example, the first duration may range between zero and one seconds, one and three seconds, two and six seconds, or five and ten seconds, or any other duration or time range.

In one example, the previous rolling average may be calculated as an average value of tissue oxygenation percentage over a second duration, whereby the previous rolling average may not include the most-recently received sensor data point (i.e. may include at least all the data points used to calculate the current rolling average, except the most-recently received sensor data point). In one example, the previous rolling average may be calculated for a second duration, equal to the first duration. In one implementation, the difference between the current rolling average, and the previous rolling average may be calculated by subtraction, thereby resulting in a percentage muscle oxygenation difference. In one implementation, one or more processes utilized to calculate a change in tissue oxygenation may be executed at block 1904 of process 1900, and by, in one example, processor 702.

In one implementation, in order to determine whether a calculated change in tissue oxygenation corresponds to a critical tissue oxygenation (critical intensity) for a given user, the calculated change in tissue oxygenation may be compared to a threshold value. In one example, this threshold value of change in tissue oxygenation percentage may include any oxygenation value. In one specific example, the threshold value of change in tissue oxygenation percentage may be less than or equal to 0.1 (i.e. the received tissue oxygenation percentage may not correspond to a critical tissue oxygenation percentage unless a difference between a current rolling average of tissue oxygenation percentage and a previous rolling average is less than or equal to 0.1 (units of tissue oxygenation percentage)). Additional or alternative tissue oxygenation thresholds may include, among others, 0.2, 0.3, 0.4, 0.5, 0.6. In one example, one or more processes may be executed to determine whether a change in tissue oxygenation is less than a threshold at decision block 1906 of process 1900.

If it is determined that a calculated change in tissue oxygenation is greater than a threshold value, one or more processes may be executed to output a signal (output to, in one example, an interface, such as a graphical user interface, or a wireless interface/transceiver) indicating that the user is not exercising at a critical tissue oxygenation. Accordingly, these one or more processes may be executed at block 1910, and by a processor, such as processor 702. If, however, it is determined that the calculated change in tissue oxygenation is less than or equal to a threshold value, flowchart 1900 may proceed to decision block 1908.

Accordingly, decision block 1908 may represent one or more processes executed to determine whether the change in tissue oxygenation (that is less than or equal to the previously-described threshold value) is consistent/steady for a threshold duration (i.e. that the change in tissue oxygenation percentage is less than or equal to a threshold change, and for a predetermined threshold duration). Accordingly, any threshold duration may be utilized with these disclosures. In certain specific examples, the threshold duration may be equal to at least one second, at least two seconds, at least three seconds, at least four seconds, at least five seconds, or at least 10 seconds, or range between approximately 1 and 10 seconds, or 5 and 15 seconds, among others. If it is determined that the calculated change in tissue oxygenation is not consistent for the threshold duration, flowchart 1900 may proceed to block 1910. If, however, it is determined that the calculated change in tissue oxygenation is consistent for the threshold duration, flowchart 1900 may proceed to block 1912.

As such, upon determining that the calculated change in tissue oxygenation is consistent for a threshold duration, one or more processes may be executed to output a signal indicating that a user is exercising at a critical work rate/critical tissue oxygenation. Specifically, in one example, one or more processes may be executed to output a critical power of the user equal to the current power as indicated by the power sensor at a time corresponding to the identified critical tissue oxygenation. Alternatively, a critical power may correspond to an average power as indicated by the power sensor over a time period corresponding to the calculation of the calculated consistent change in tissue oxygenation. As such, these one or more processes configured to output a critical power to an interface may be executed by processor 702. Further, one or more processes may be executed at block 1912 to output the critical power corresponding to those received sensor values for which the difference between the current rolling average and previous rolling average is less than or equal to the threshold.

In one example, there may be some degree of variation in a calculated/identified critical power for a user based upon multiple calculations of the critical muscle oxygenation during different times of a same exercise. Accordingly, in one example, the critical power outputted at block 1912 may be averaged across multiple separately-calculated critical tissue oxygenation percentages for a same user during an exercise session, among others. Accordingly, in one example, the data points 1808, 1810, and 1812 may represent exemplary data points from a plurality of critical power results corresponding to multiple calculations of critical tissue oxygenation of the user. As such, in one example, the critical power values associated with data points 1808, 1810, and 1812 may be averaged.

In one implementation, the tissue oxygenation discussed in relation to flowchart 1900, as well as throughout this disclosure, may comprise a muscle oxygenation for any muscle within a user's body. Further, the critical power value calculated at block 1912 may be utilized to calculate an anaerobic work capacity (W') for the user (in one example, this anaerobic work capacity may be expressed as a power (units: W)), and calculated as a difference between a current muscle oxygenation percentage (Power$_{current}$) (above the critical muscle oxygenation percentage) and the critical power (Power$_{crit}$), summed over a duration of an exercise session. As such, these calculated differences may be referred to as positive difference values. In one example, an exercise session may end in user fatigue. Accordingly, one or more processes utilized to calculate an anaerobic work capacity may be executed by processor 702 at block 1914:

$W' = \Sigma_{t=0}^{fatigue}$ (Power$_{current}$− Power$_{crit}$) (Units: W);   (Second anaerobic work capacity equation)

In certain examples, a critical velocity and an anaerobic work capacity for a user may be calculated based upon sensor output data indicating, or used to calculate, a speed of the user. As such, a critical velocity and an anaerobic work capacity for a user may be calculated based upon sensor data received from, among others, an accelerometer, a location-determining sensor, or a bicycle speedometer, and without utilizing a tissue oxygenation sensor, as previously described. In one implementation, the present disclosure describes results of a plurality of validation tests utilized to validate a relationship between speed data and a critical intensity for a user. Accordingly, in one example, an end speed may be calculated in order to estimate a critical speed for a user.

Figure 20:
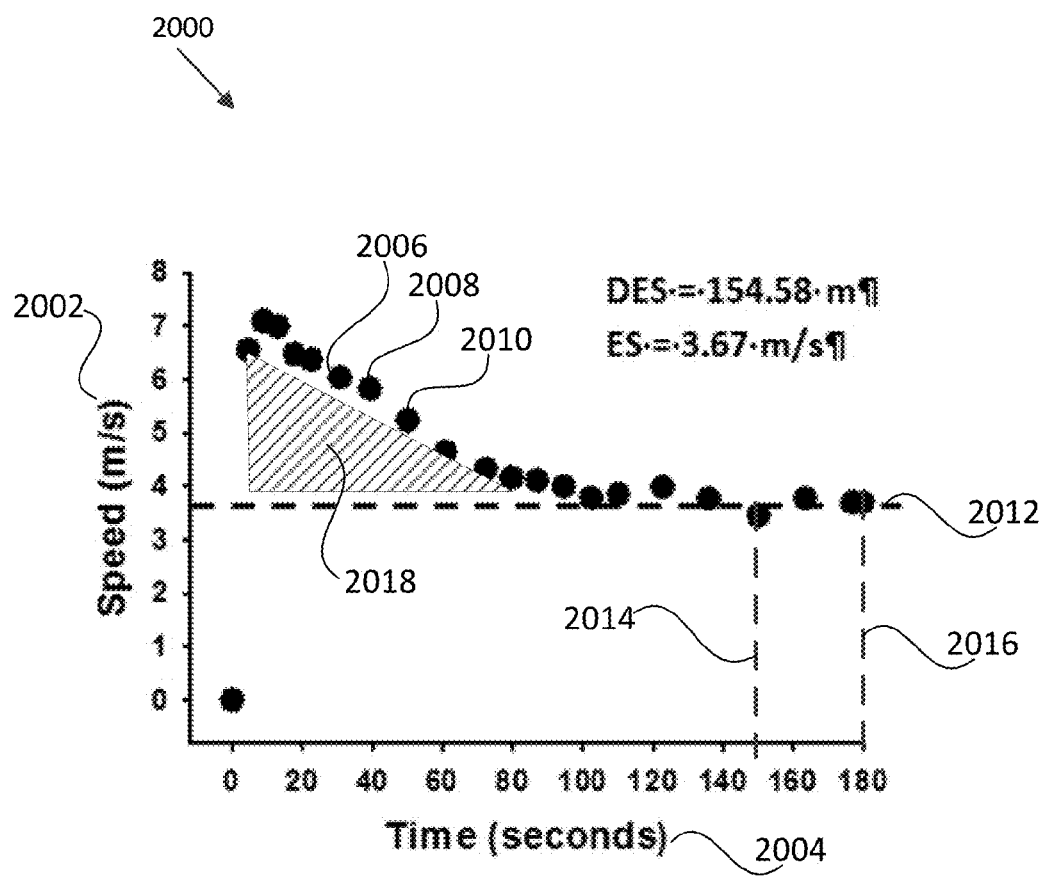
FIG. 20 depicts a graph of output speed data for an exercise session, according to one or more aspects described herein.

FIG. 20 depicts a graph 2000 that may be utilized to calculate an end speed of the user during an exercise session, and comprising speed on the y-axis 2002 versus time on the x-axis 2004. The plotted data points, of which data points 2006, 2008, 2010 are an exemplary sub-set, comprise measurements of a speed of the user at a given time during a same exercise session. In one example, the end speed, denoted by line 2012, may be calculated as an average of a sub-set of the plurality of data points that make up the graph 2000. In particular, the end speed 2012 may be calculated as an average of those data points during a final 30 seconds of the duration of the exercise session (e.g. an average of those data points between lines 2014 and 2016). However, an end speed may be calculated as an average speed for different durations, such as, among others, a final 20 seconds, 10 seconds, or 5 seconds of an exercise session, or any other duration. In one example, graph 2000 may represent data points associated with an exercise session having a prescribed duration. Accordingly, the prescribed duration may range from 1 minute to 10 minutes. In one specific example, the exercise session associated with graph 2000 may be a three minute all-out trial, whereby a user is instructed to exercise as a highest subjective intensity level for the prescribed duration (three minutes). Additional or alternative exercise session prescriptions (times and/or intensity levels) may be utilized without departing from the scope of these disclosures.

In one example, based upon validation testing comparing calculated end speeds for multiple users across multiple separate exercise sessions, a relationship between a calculated end speed and a critical speed for a given user may was identified. In particular, for a plurality of validation tests, 90% of a sample population of users were found to be able to sustain exercise for up to 15 minutes when exercising between 5% and 10% below a calculated end speed for a three minute all-out trial. Additionally, for the plurality of validation tests, 85% of the sample population of users were found to be able to sustain exercise for up to 20 minutes when exercised between 5% and 10% below the calculated end speed for the three minute all-out trial. Accordingly, in one example, a critical velocity for a user may be estimated by reducing a calculated end speed by 5 to 10% (e.g. calculating 90-95% of an end speed of a user). In one specific example, a critical velocity may be estimated for a user by calculating 92.5% of an end speed, among others.

In one implementation, an anaerobic work capacity, expressed as a distance, it may be calculated based upon a calculated end speed for a user. Accordingly, from a plurality of validation testing comparing a distance above end speed to an anaerobic work capacity for a given user, it was found that an anaerobic work capacity may be estimated by increasing a calculated end speed by, in one example, 25% to 35%. In another specific example, an anaerobic work capacity may be estimated by increasing the calculated end speed by 30%. Accordingly, in one example, the distance above end speed may be as that area 2018 from FIG. 20 (e.g. an integration of differences between speed data points and the calculated end speed 2012 across the duration of the exercise session associated with graph 2000).

Figure 21:
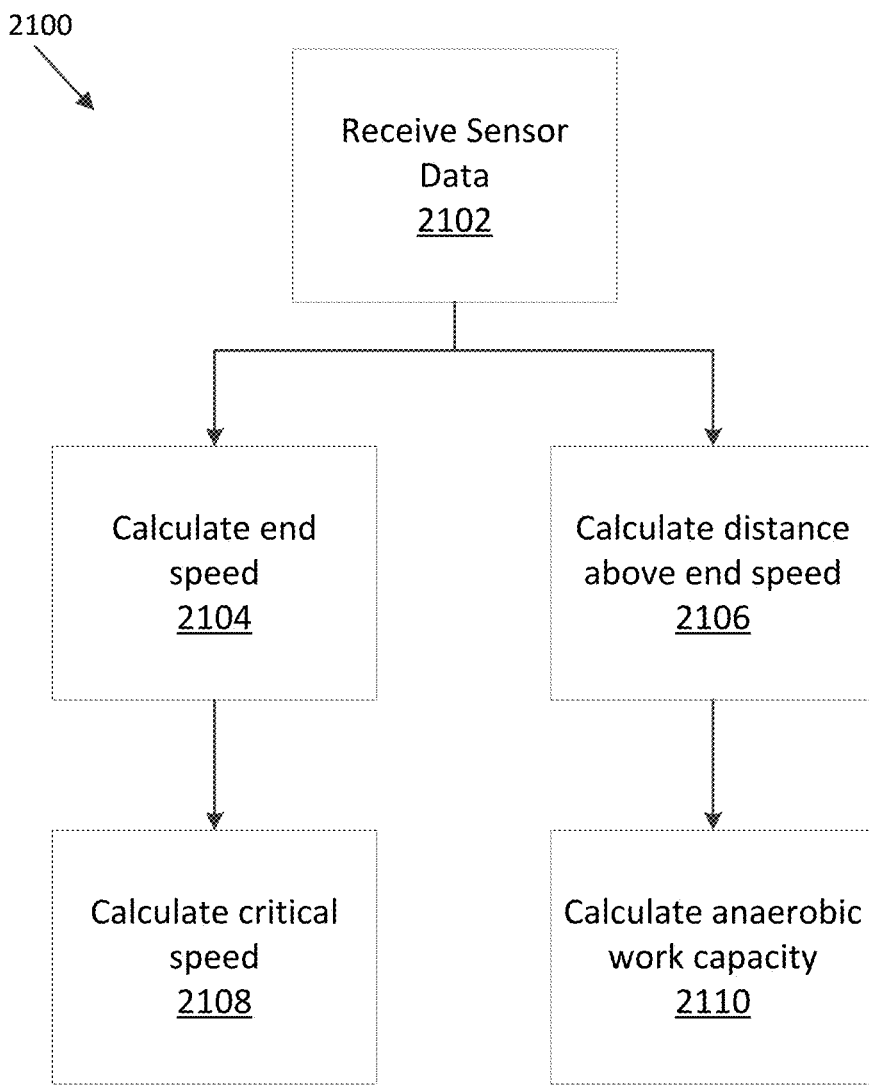
FIG. 21 is a flowchart diagram that may be utilized to calculate a critical speed and an anaerobic work capacity based upon speed sensor data, according to one or more aspects described herein.

FIG. 21 is a flowchart diagram 2100 that may be utilized to calculate a critical speed and an anaerobic work capacity for a user based upon sensor data indicative of a speed of the user. Accordingly, in one example, one or more processes associated with flowchart diagram 2100 may be executed by an activity monitoring device, such as device 700. It is noted that flowchart diagram may utilized a sensor, such as sensor 706 of device 700, but may not utilize an oxygenation sensor, such as sensor 710. In one example, the activity monitoring device 700 may receive sensor data from a sensor, such as sensor 706. The received sensor data may comprise data points indicative of a speed of the user at various time points during an exercise session. In another example, the received sensor data points may comprise data indicative of a location of the user, and may be utilized to calculate a speed. In one example, data points may be received periodically, and with any periodicity, without departing from the scope of these disclosures. The received data points may be associated with an exercise session having a prescribed duration and intensity. In particular, the exercise session may comprise a three minute all-out trial that instructs a user to exercise as a highest subjective intensity for a three minute duration. In another example, a prescribed duration of 2 to 5 minutes maybe utilized. In other examples, alternative durations may be utilized, without departing from the scope of these disclosures. In one example, one or more processes may be executed to receive sensor data at block 2102 of flowchart 2100.

An end speed may be calculated from received sensor data as an average speed of a sub-set of a plurality of sensor data points received during an exercise session. In one specific example, an end speed may be calculated as an average speed during a last 30 seconds of the prescribed duration of the exercise session. However, alternative sub-sections of a prescribed duration of an exercise session may be utilized to calculate an end speed, without departing from the scope of these disclosures. In one example, one or more processes may be executed, such as by a processor 702 to calculate an end speed at block 2104 of flowchart 2100.

A distance above the end speed may be calculated by summing differences between instantaneous speeds (Speed$_{current}$) and the calculated end speed (Speed$_{end}$) across the duration of the exercise session (i.e. between time t=0 and the end of the session, time t=session end). In one implementation, one or more processes may be executed to calculate a distance above an end speed at block 2106 of flowchart 2100:

Distance above end speed=$\Sigma_{t=0}^{session\ end}$ (Speed$_{current}$−Speed$_{end}$) (Units: m); (Distance above end speed equation)

In one example, a critical speed may be calculated/estimated based upon the calculated end speed. In one implementation, a critical speed may be calculated by decreasing the calculated end speed by between 5 and 10%:

Speed$_{critical}$=Speed$_{end}$*(90-95%).

In one specific example, a critical speed may be calculated as 92.5% of a calculated end speed:

Speed$_{critical}$=Speed$_{end}$*(92.5%).

In one implementation, one or more processes may be executed to calculate a critical speed, based upon the calculated end speed, at block 2108 of flowchart 2100.

In one example, an anaerobic work capacity may be calculated based upon the calculated distance above an end speed. Accordingly, the anaerobic work capacity may be calculated as 125% to 135% of a distance above the calculated end speed:

Anaerobic work capacity=(distance above end speed)*(125-135%).

In one specific example, an anaerobic work capacity may be calculated as 130% of a distance above the calculated end speed:

Anaerobic work capacity=(distance above end speed)*(130%).

In one implementation, one or more processes may be executed to calculate the anaerobic work capacity, based upon the calculated distance above the end speed, at block 2110 of flowchart 2100.

Figure 22:
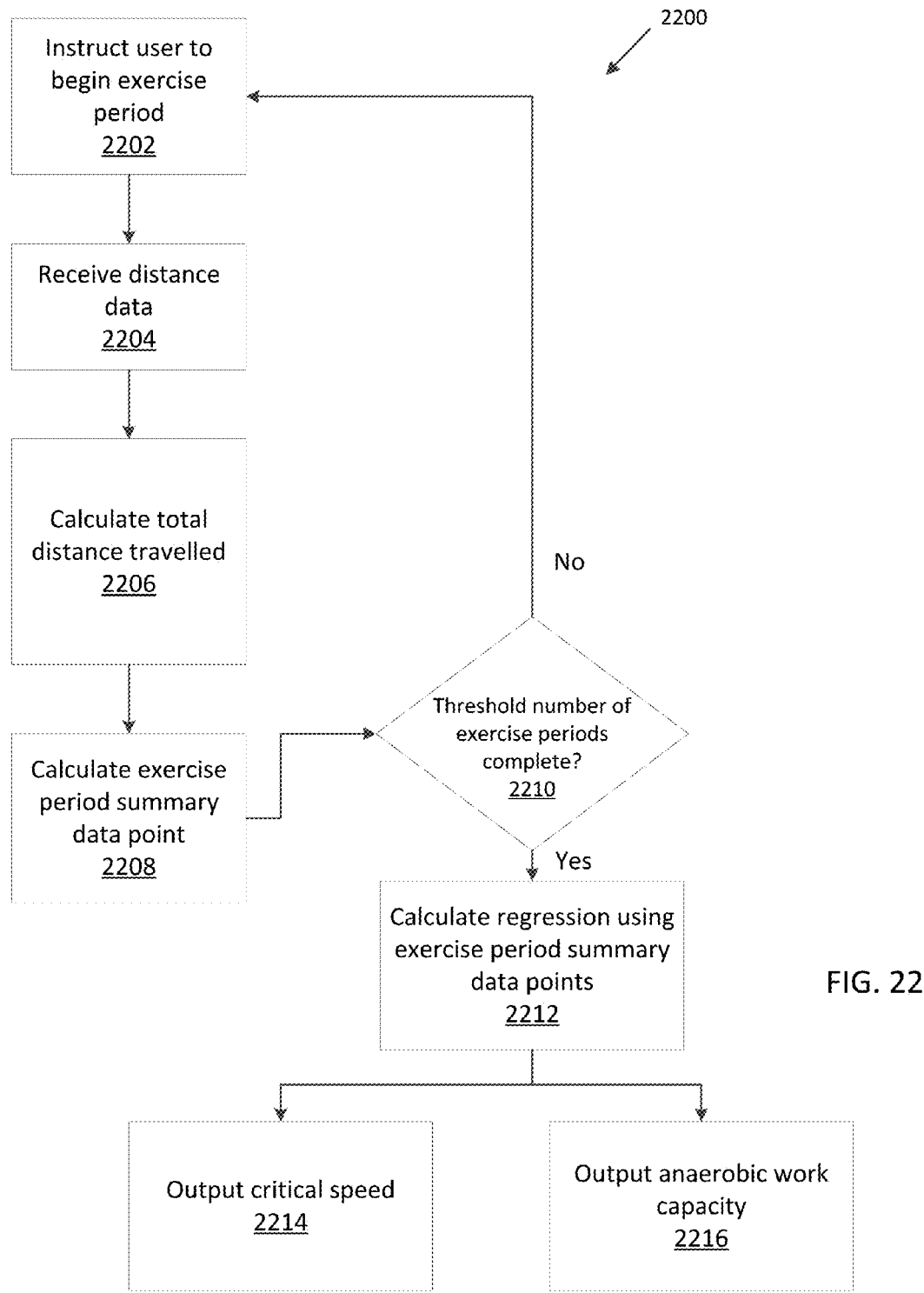
FIG. 22 is a flowchart diagram that may be utilized to calculate a critical speed and/or an anaerobic work capacity of the user, according to one or more aspects described herein.

In one implementation, a critical speed and an anaerobic work capacity associated with a user may be calculated from data received from a sensor configured to output data indicative of a distance traveled by the user during an exercise session (e.g. distance traveled while running, cycling, and the like). As such, the sensor may comprise one or more of an accelerometer, a location determining sensor, or a bicycle speedometer, among others. As such, the sensor may be configured to output data indicative of a location of a user, which may in turn be used to calculate a distance traveled by the user, as well as to determine a time taken to travel the recorded distance. Accordingly, FIG. 22 schematically depicts a flowchart diagram 2200 that may be utilized to calculate one or more of a critical speed and/or an anaerobic work capacity of a user from data outputted from a sensor, such as sensor 706.

In one implementation, in order to calculate one or more of a critical speed and/or an anaerobic work capacity, a user may provide an activity monitoring device, such as device 700, with test data. In one example, test data may be generated by a sensor, such as sensor 706, during an exercise period, which may otherwise be referred to as an exercise session. In one example, an exercise period may comprise a prescribed duration during which a user is instructed to run as quickly as possible (i.e. as far as possible) within the prescribed time limit. In certain specific examples, an exercise period may instruct a user to run as far as possible within, for example, a minute, two minutes, three minutes, four minutes, five minutes, six minutes, seven minutes, eight minutes, nine minutes, 10 minutes, 12 minutes, 15 minutes, 20 minutes, or any other duration. Accordingly, a sensor, such as sensor 706, may be configured to output a location of the user for each second of an exercise period. In turn, this location data may be utilized to calculate a total distance traveled by the user during the exercise period. Alternatively, the sensor 706, may be configured to a location data point at a different frequency, which may be 0.25 Hz, 0.5 Hz, 2 Hz, 3 Hz, 4 Hz, or any other frequency. In one example, an exercise period prescribed for a user in order to generate test data may ensure that the user exercises at an intensity above a critical intensity for the user during at least a portion of the prescribed duration of the exercise period. Accordingly, in one example, one or more processes may be executed to instruct a user to begin an exercise period at block 2202 of flowchart 2200.

In one example, the sensor 706 may output a data point indicative of a current location and/or a distance traveled by the user for each second of an exercise period. Accordingly, in one example, the outputted data may be received for further processing by, in one example, processor 702, at block 2204 of flowchart 2200.

In one implementation, a data point associated with each second of a prescribed exercise period may be stored. As such, location data for each second of a prescribed exercise period may be stored in, for example, memory 704. Upon completion of a given exercise period, a total distance traveled during a prescribed exercise period may be calculated. In one implementation, this total distance traveled may be calculated by, in one example processor 702, and at block 2206 of flowchart 2200.

Figure 23:
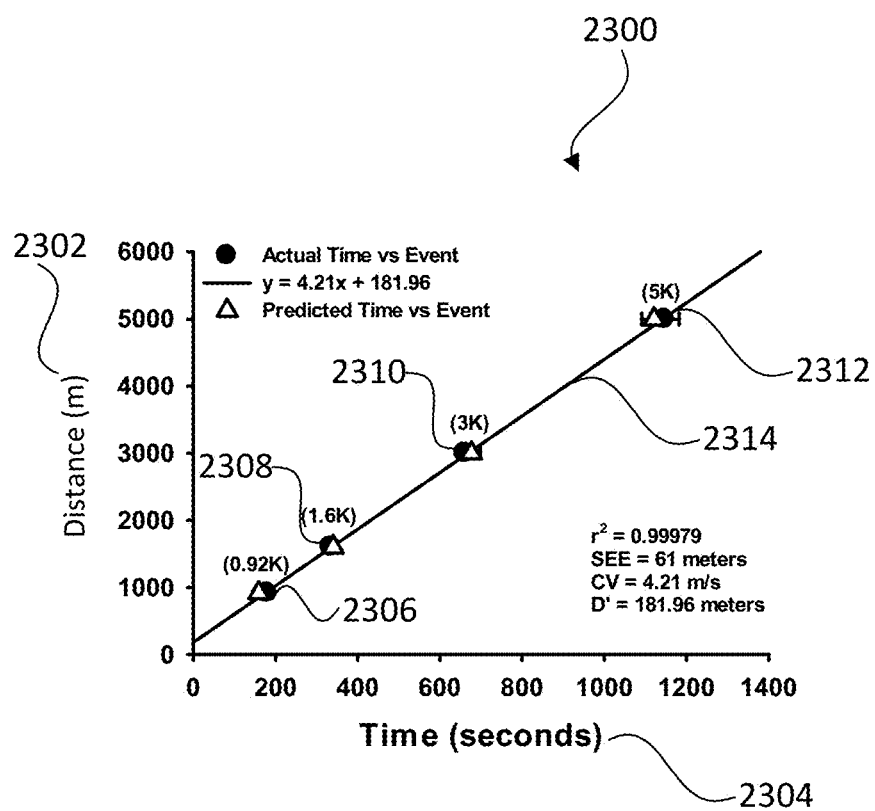
FIG. 23 is a chart that plots distance data for multiple exercise sessions of a user, according to one or more aspects described herein.

In one example, an exercise period utilized to generate data in order to determine a critical speed and/or an anaerobic work capacity of the user may be summarized as a data point comprising two pieces of information. This exercise period summary data point may comprise the total distance traveled, as determined, in one example, at block 2206, in addition to the total time (i.e. the duration) of the exercise period/session. In one example, the two pieces of information (i.e. the total distance, and the total time) may be expressed as a coordinate point. In one example, this coordinate point P may be of the form P(x$_3$, y$_3$), where y$_3$ may be the total distance (m), and x$_3$ may be the total time (s). In this way, the exercise period summary data point expressed as a coordinate point may be plotted, as schematically depicted in FIG. 23. In one example, the exercise period summary data point may be calculated at block 2208 of flowchart 2200.

In one implementation, in order to calculate one or more of a critical speed and/or an anaerobic work capacity of a user, two or more exercise period summary data points may be utilized. In one example, the durations of the exercise periods used to generate the two or more exercise period summary data points may be different. Accordingly, in one example, one or more processes may be executed to determine whether a threshold number of exercise periods have been completed by the user in order to calculate one or more of a critical speed and/or an anaerobic work capacity for the user. As previously described, this threshold number of exercise periods may be at least two, at least three, at least four, or at least five, among others. In one specific example, one or more processes may be executed by processor 702 to determine whether the threshold number of exercise periods have been completed at decision block 2210 of flowchart 2200. Accordingly, if the threshold number of exercise periods has been met or exceeded, flowchart 2200 proceeds to block 2212. If, however, the threshold number of exercise periods has not been met, flowchart 2200 proceeds from decision block 2210 back to block 2202.

In one example, a regression may be calculated using the two or more exercise period summary data points that were calculated from two or more prescribed exercise periods. In one example, this regression may be a linear, or a curvilinear regression. As such, any computational processes known in the art for calculation of a linear or curvilinear regression may be utilized with this disclosure. In one implementation, at least a portion of a calculated regression may be utilized to determine one or more of a critical tissue oxygenation percentage and/or an anaerobic work capacity of the user. In one specific example, one or more processes may be executed to calculate a regression at block 2212 of flowchart 2200.

In one example, at least a portion of a regression calculated using the two or more exercise period summary data points may be utilized to determine a critical speed for a user. Specifically, the critical speed may correspond to a slope of the regression line (or a slope of a linear portion of a curvilinear regression). In one implementation, one or more processes may be executed to output a critical speed calculated as a slope of a regression line through the two or more exercise period summary data points at block 2214 of flowchart 2200.

In another example, at least a portion of a regression calculated using the two or more exercise period summary data points may be utilized to determine an anaerobic capacity for of the user. Specifically, the anaerobic capacity may correspond to an intercept of the regression line (or an intercept of a linear portion of a curvilinear regression). In one example, the anaerobic capacity may be expressed as a total distance (m) above a critical speed (m/s). In one implementation, one or more processes may be executed to output an anaerobic capacity calculated as an intercept of a regression line through the two or more exercise period summary data points, at block 2216 of flowchart 2200.

FIG. 23 is a chart that plots testing data from multiple exercise sessions for a given user. In particular, FIG. 23 is a chart 2300 plotting distance 2302 against time 2304. Points 2306, 2308, 2310, and 2312 may each represent a separate exercise sessions, and such that at least a portion of each of these exercise sessions is carried out within a severe exercise intensity domain for the user. In one implementation, the exercise period summary data points 2306, 2308, 2310, and 2312 may each represent a separate exercise session carried out in a continuous manner. However, in another implementation, one or more of the exercise period summary data points 2306, 2308, 2310, and 2312 may represent a separate exercise session carried out in an intermittent manner.

In one implementation, a regression line 2314 may be calculated using the four exercise period summary data points 2306, 2308, 2310, and 2312, as plotted on chart 2300. In one example, this regression line 2314 may be of the form:

$$y = m_d x + c_d$$

where y is a total distance (y-axis), x is a time (s) (x-axis), $m_d$ is the slope of the regression line 2314 and $c_d$ is the intercept of the regression line 2314 on the y-axis.

For the example experimental data used to generate the exercise period summary data points 2306, 2308, 2310, and 2312, the regression line 2314 may have the form: y=4.21x+181.96, with an $r^2$ value of 0.99979. It is noted that this regression line 2314 formula is merely included as one example result.

In one example, a regression line, such as regression line 2314, through two or more exercise period summary data points, such as the exercise period summary data points 2306, 2308, 2310, and 2312, may be used to calculate a critical speed and/or a total distance above a critical speed (D') (which may be proportional to an anaerobic work capacity) for a user. In one example, given regression line 2314 of the form: y=mx+c, the critical speed may be equal to m, the slope of the regression line 2314, and the total distance above the critical speed may be equal to c (or |c|, the absolute value of c), the intercept of the regression line 2314 on the y-axis. In particular, given the experimental data depicted in chart 2300, the critical speed for the user may be 4.21 m/s and the total distance above the critical speed may be 181.96 m.

In certain examples, a critical velocity, a critical power, and/or an anaerobic work capacity may be calculated based upon a single input data point. In one implementation, this single input data point may comprise a race time (comprising a distance and a time taken to complete the race distance). In one example, a race time may be utilized based upon an assumption that at least a portion of the race was carried out within a severe exercise intensity domain. However, a single input data point comprising a distance completed and a time taken to complete the distance derived from an exercise session other than a race (i.e. an informal running session untaken by a user) may be utilized with the systems and methods described herein. In another implementation, a single input data point may be utilized to calculate a critical power and/or an anaerobic work capacity, and such that the single input data point may comprise the total amount of work done, and a total time taken.

Figure 24:
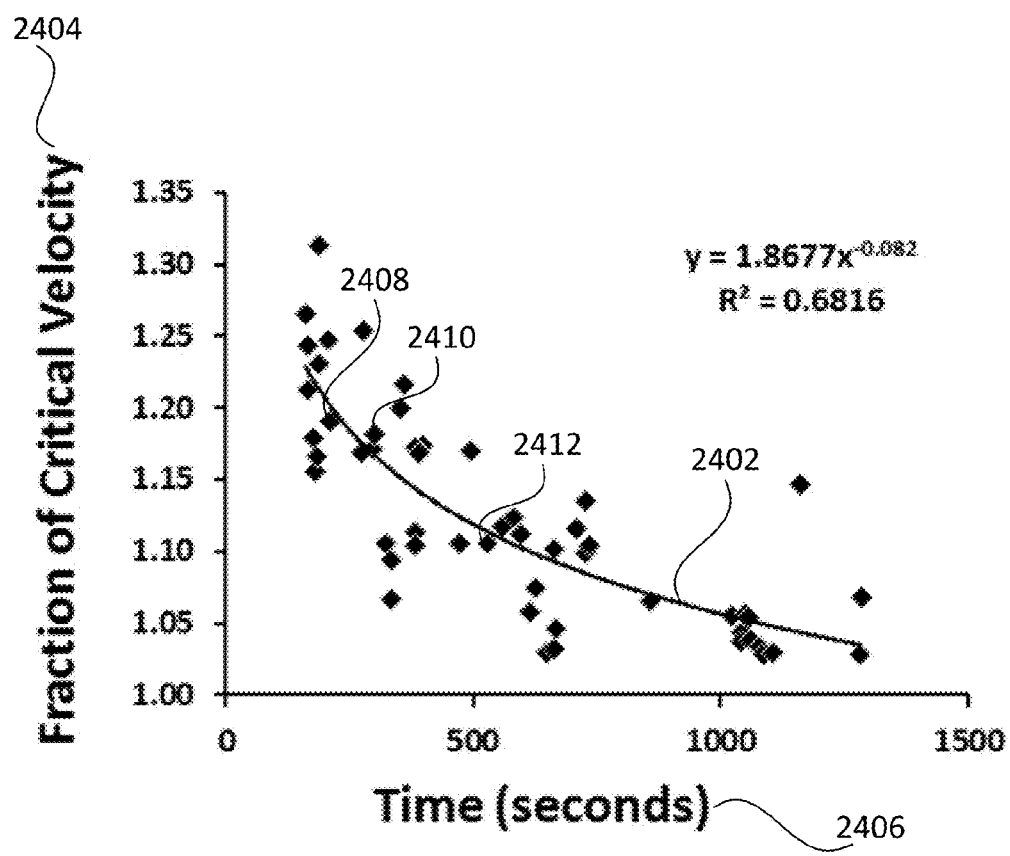
FIG. 24 schematically depicts a model for prediction of a critical velocity fraction for running, according to one or more aspects described herein.

In one implementation, a single input data point may be utilized to calculate one or more of a critical velocity, critical power, and/or an anaerobic work capacity based upon relationships (models) developed through analysis of multiple exercise sessions by multiple different users. In particular, FIG. 24 depicts a model 2402 that may be utilized to predict a fraction of a critical velocity (y-axis 2404) based upon an input of a total athletic session time (x-axis 2406) for running. The data points 2408, 2410, and 2412 are exemplary data points from a plurality of data points that may be utilized to develop the model 2402. Accordingly, data points 2408, 2410, and 2412 may represent separate exercise sessions (for a running exercise session) by a same user, or by different users. In one example, model 2402 may be of the form: y=1.8677*x$^{-0.082}$, with an $r^2$ value of 0.6816. In another example, model 2402 may be of the form: y=1.87*x$^{-0.1}$.

Figure 25:
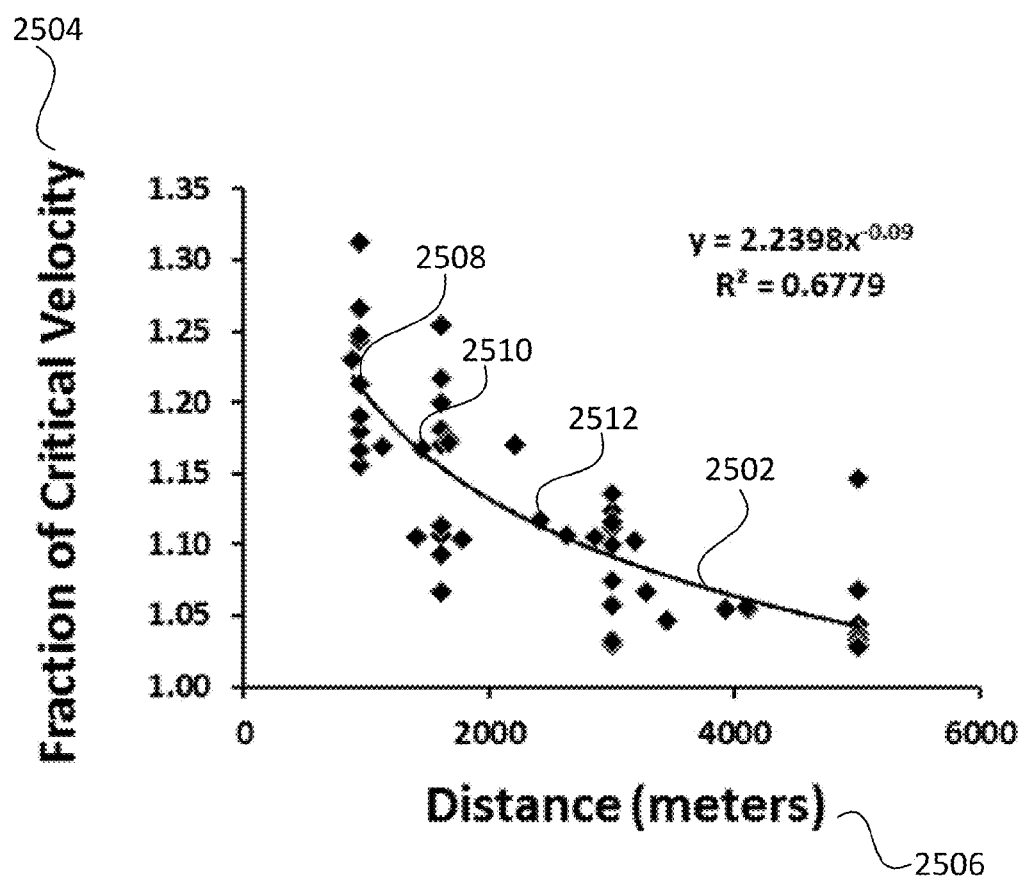
FIG. 25 schematically depicts a model for prediction of a critical velocity fraction for running, according to one or more aspects described herein.

FIG. 25 depicts a model 2502 that may be utilized to predict a fraction of a critical velocity (y-axis 2504) based upon an input of a total athletic session distance (x-axis 2506) for a running exercise session. The data points 2508, 2510, and 2512 are exemplary data points from a plurality of data points that may be utilized to develop the model 2502. Accordingly, data points 2508, 2510, and 2512 may represent separate exercise sessions (for a running exercise session) by a same user, or by different users. In one example, model 2502 may be of the form: y=2.2398*x$^{-0.09}$, with an $r^2$ value of 0.6779. In another example, model 2502 may be of the form: y=2.2*x$^{-0.1}$.

Figure 26:
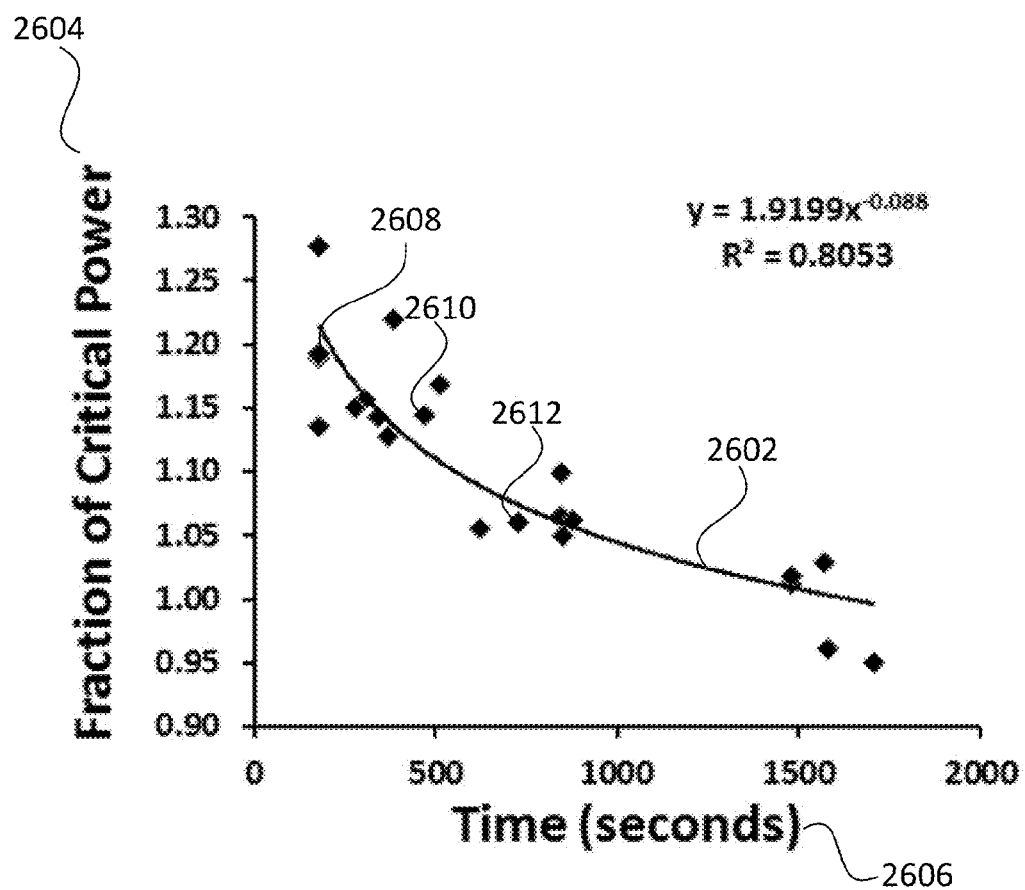
FIG. 26 schematically depicts a model for prediction of a critical velocity fraction for cycling, according to one or more aspects described herein.
Figure 27:
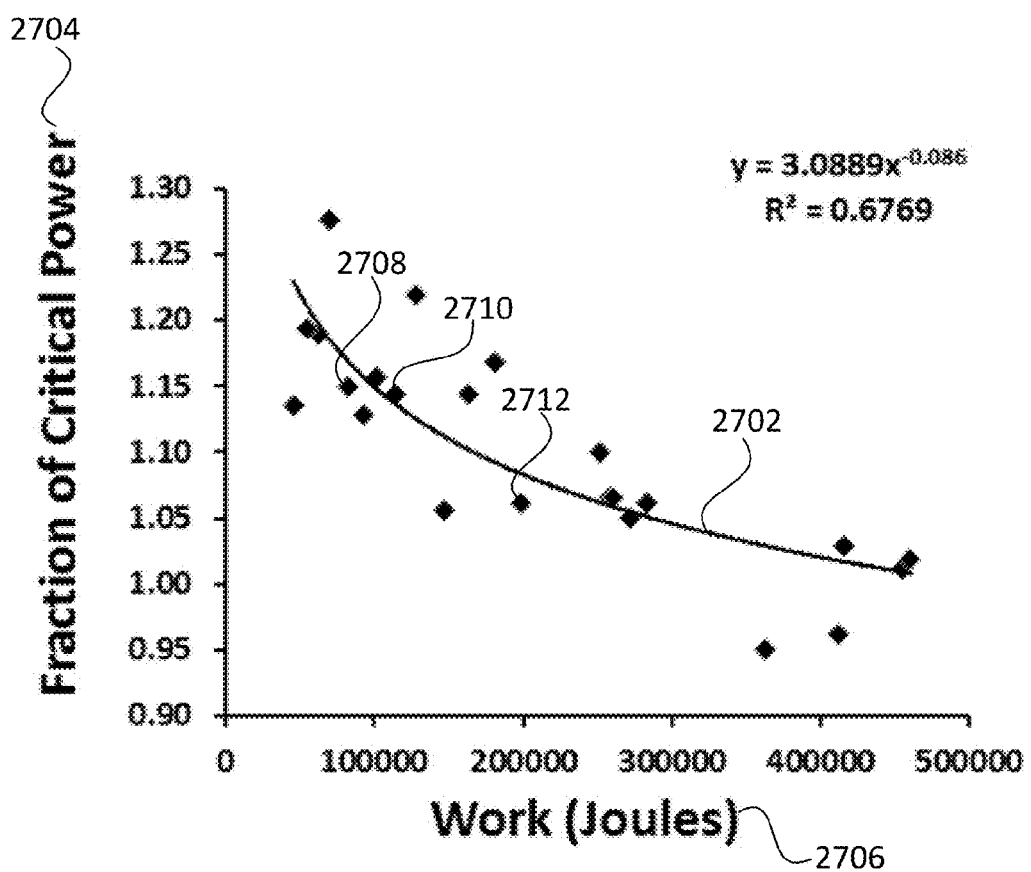
FIG. 27 schematically depicts a model for prediction of a critical velocity fraction for cycling, according to one or more aspects described herein.

FIG. 26 depicts a model 2602 that may be utilized to predict a fraction of a critical velocity (y-axis 2604) based upon an input of a total athletic session time (x-axis 2606)

for cycling. The data points 2608, 2610, and 2612 are exemplary data points from a plurality of data points that may be utilized to develop the model 2602. Accordingly, data points 2608, 2610, and 2612 may represent separate exercise sessions (for a cycling exercise session) by a same user, or by different users. In one example, model 2602 may be of the form: $y=1.9199*x^{-0.088}$, with an $r^2$ value of 0.8053. In another example, model 2602 may be of the form: $y=1.9*x^{-0.1}$ FIG. 27 depicts a model 2702 that may be utilized to predict a fraction of a critical velocity (y-axis 2704) based upon an input of a total amount of energy expended during an athletic session (x-axis 2706) for cycling. The data points 2708, 2710, and 2712 are exemplary data points from a plurality of data points that may be utilized to develop the model 2702. Accordingly, data points 2708, 2710, and 2712 may represent separate exercise sessions (for a cycling exercise session) by a same user, or by different users. In one example, model 2702 may be of the form: $y=3.0889*x^{-0.086}$, with an $r^2$ value of 0.6769. In another example, model 2702 may be of the form: $y=3.1*x^{-0.1}$.

In one implementation, models 2402, 2502, 2602, and/or 2702 may be calculated using any mathematical modeling methodology known in the art (e.g. regression modeling methodologies, among others).

Figure 28:
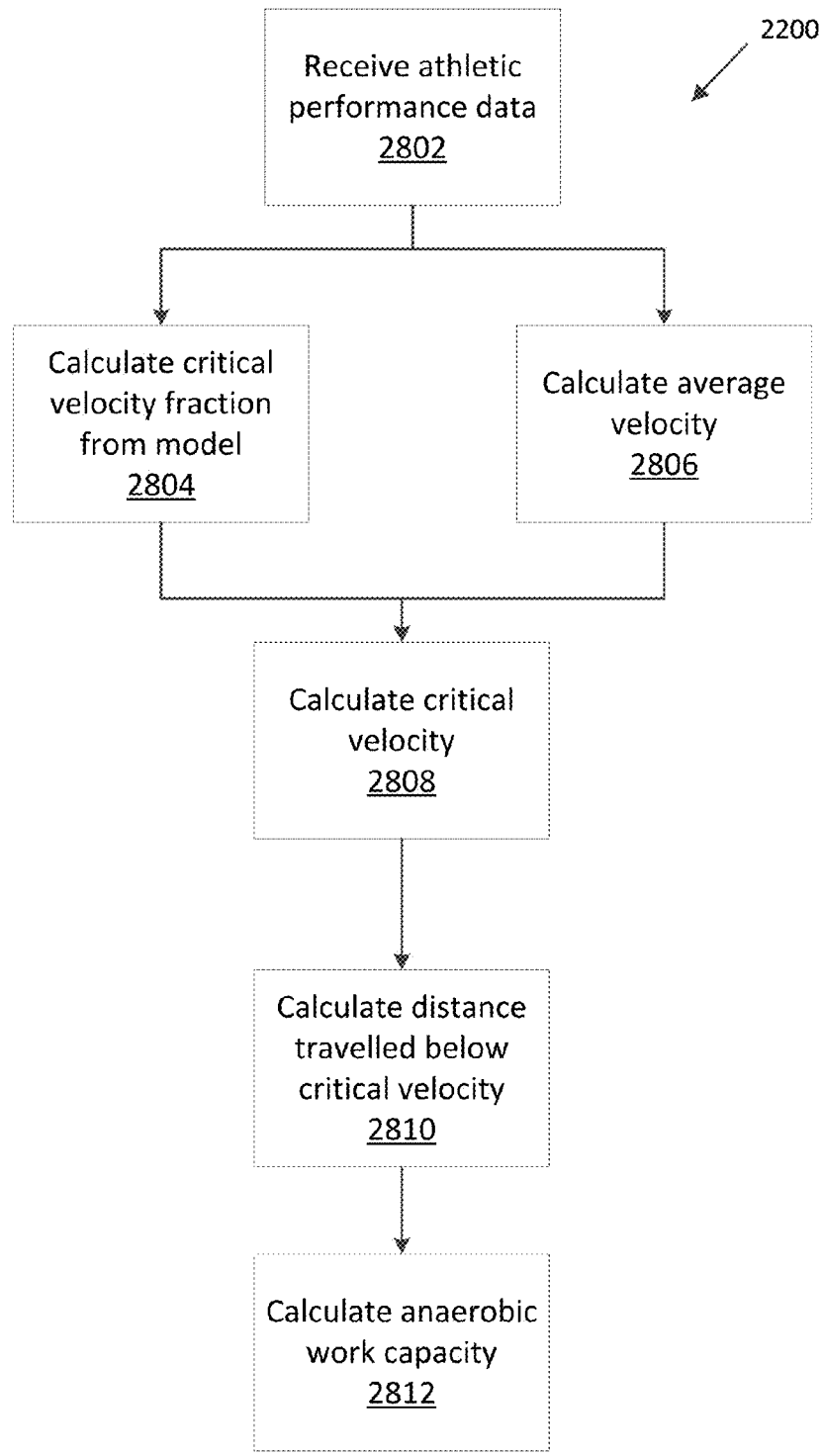
FIG. 28 is a flowchart diagram that may be utilized to calculate a critical velocity and an anaerobic work capacity based upon a single input data point, according to one or more aspects described herein.

FIG. 28 is a flowchart diagram 2800 that may be utilized to calculate one or more of a critical velocity (or critical power) and an anaerobic work capacity based upon a single input data point. Accordingly, the one or more processes associated with flowchart 2800 may be executed by a processor, such as processor 702. In one example, a single input data point may comprise a total time in combination with a total distance for an exercise session. In one example, at least a portion of the exercise session may be carried out within a severe exercise intensity domain. In another example, a single input data point may comprise a total power expended and a total time associated with an exercise session. Accordingly, one or more processes executed to receive the single input data point may be executed at block 2802. In one specific example, a data point may indicate that a user completed a 5 km race in 1300 seconds.

A mathematical model may be utilized to calculate a critical velocity fraction or a critical power fraction. Accordingly, an input to a model, from, in one example, models 2402, 2502, 2602, and/or 2702, may comprise a total distance traveled during an exercise session, a total time to complete an exercise session, or a total power expended during an exercise session. Further, the selection of a model, from, in one example, models 2402, 2502, 2602, and/or 2702, may be based upon an activity type (e.g. running or cycling, among others). In one implementation, one or more processes may be executed to calculate a critical velocity fraction or a critical power fraction at block 2804 of flowchart 2800. For the specific example of a 5 km race run completed in 1300 seconds, the critical velocity fraction may be calculated as $y=1.8677*(1300)^{-0.082}$ (model 2402), which implies that the critical velocity fraction (y)=1.045.

Additionally, an average velocity may be calculated as a total exercise session distance divided by a total time taken to complete the distance. In another implementation, an average exercise session power may be calculated as a total exercise session power divided by a total time taken to complete the exercise. Accordingly, one or more processes may be executed to calculate an average exercise session velocity, or an average exercise session power, at block 2806 of flowchart 2800. For the specific example of a 5 km race run in 1300 seconds, the average exercise session velocity may be 5000/1300=3.85 m/s.

A critical velocity may be calculated as an average velocity divided by the critical velocity fraction. Alternatively a critical power for a user may be calculated as an average power divided by the critical power fraction. Accordingly, one or more processes may be executed to calculate a critical velocity, or a critical power, at block 2808 of flowchart 2800. For the specific example of a 5 km race run in 1300 seconds, the critical velocity may be calculated as 3.85/1.045=3.68 m/s.

A total distance traveled below a critical velocity may be calculated as an average velocity multiplied by a total time associated with an exercise session. Alternatively, the total amount of energy expended below a critical power may be calculated as an average power multiplied by a total time associated with an exercise session. Accordingly, one or more processes may be executed to calculate a total distance traveled below a critical velocity, or a total amount of energy expended below a critical power, at block 2810 of flowchart 2800. For the specific example of a 5 km race run in 1300 seconds, the distance traveled below the critical velocity may be calculated as 3.68*1300=4784 m.

An anaerobic work capacity may be calculated as a distance above a critical velocity, or as a total amount of energy above a critical power. Accordingly, an anaerobic work capacity may be calculated (e.g. for running) as a difference between a total distance traveled during an exercise session and a total distance traveled below a critical velocity, as calculated at block 2810. Alternatively, an anaerobic work capacity may be calculated (e.g. for cycling) as a difference between a total amount of energy expended during an exercise session and a total amount of energy expended below a critical power, as calculated at block 2810. Accordingly, one or more processes may be executed to calculate an anaerobic work capacity at block 2812 of flowchart 2800. For the specific example of a 5 km race run in 1300 seconds, the distance traveled above the critical velocity (i.e. the anaerobic work capacity, D') may be equal to 5000−4784=216 m.

In certain implementations, a volume of oxygen consumption associated with an exercise session participated in by a user may be estimated without using any sensors. In particular, a volume of oxygen consumption of the user may be estimated based upon an athletic profile constructed using one or more questions answered by the user. This questionnaire may be administered to the user in an electronic format, and may comprise one or more questions. In one example, answers to these questions may be based on a scale. In one example, the scale may comprise numbers from 0 to 10. However, additional or alternative scales may be utilized, without departing from the scope of these disclosures. Specifically, the questions may include, among others: an estimation of bone size, an estimation of leanness of the user, an estimation of muscle size, an estimation of sleep quality, an estimation of relaxation habits, an estimation of nutrition quality, an estimation of smoking status, an estimation of drinking habits, and an estimation of an activeness of the user. Additional or alternative questionnaire questions utilized to construct an athletic profile for the user may include, a user's age, gender, height, waist circumference, weight, as well as an indication as to whether the user is pregnant. Still further questionnaire questions may include an estimation of a 5 km running race pace (or a pace associated with another distance), and an estimation of a number of days active during the week.

Figure 29:
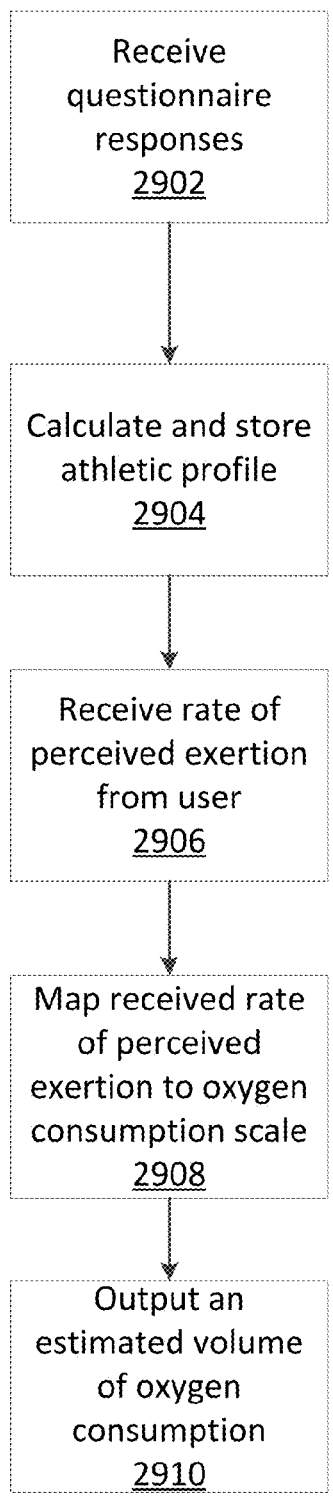
FIG. 29 is a flowchart diagram that may be utilized to estimate a volume of oxygen consumption in response to a received rate of perceived exertion of the user, according to one or more aspects described herein.

FIG. 29 depicts a flowchart diagram 2900 that may be utilized to estimate a volume of oxygen consumption of the user in response to a received rate of perceived exertion of the user, and using an athletic profile constructed using one or more questionnaire questions. In particular, a user may be asked to respond to one or more questionnaire questions, which may include one or more of those questions described above. Accordingly, one or more processes may be executed by a processor, such as processor 702 to receive one or more questionnaire responses at block 2902 of flowchart 2900.

An athletic profile may be calculated and stored, such as within memory 704, based upon one or more of the received questionnaire responses. Accordingly, this athletic profile may account for one or more physical and/or behavioral attributes associated with user, which may impact a volume of oxygen consumption for the user. In one example, the athletic profile may estimate a maximal volume of oxygen consumption associated with user, based upon one or more physical and/or behavioral attributes of the user. Accordingly, one or more processes may be executed to calculate and store the athletic profile at block 2904.

In one example, a user may input a rate of perceived exertion following an exercise session. This rate of perceived exertion may be received by a processor, such as processor 702 via an interface, such as interface 708. In one example, the rate of perceived exertion may be received as a number on a scale of 0 to 10. However, those of ordinary skill in the art will recognize that additional or alternative scales may be utilized with his rate of perceived exertion, without departing from the scope of these disclosures. In one example, the rate of perceived exertion may be received from the user at block 2906.

The received rate of perceived exertion may be mapped to an oxygen consumption scale for the user, based upon the constructed athletic profile for the user. In one example, the scale of the rate of perceived exertion may be linearly mapped to a volume of oxygen consumption scale delimited by a maximal oxygen consumption estimated for the user based upon the calculated athletic profile for the user. In other implementations, nonlinear mappings of the rate of perceived exertion scale to the volume of oxygen consumption scale may be utilized, without departing from the scope of these disclosures. Accordingly, one or more processes to map the received rate of perceived exertion to the oxygen consumption scale may be executed at block 2908. Additionally, one or more processes may be executed to output an estimated volume of oxygen consumption, based upon the inputted rate of perceived exertion of the user, at block 2910.

Figure 30:
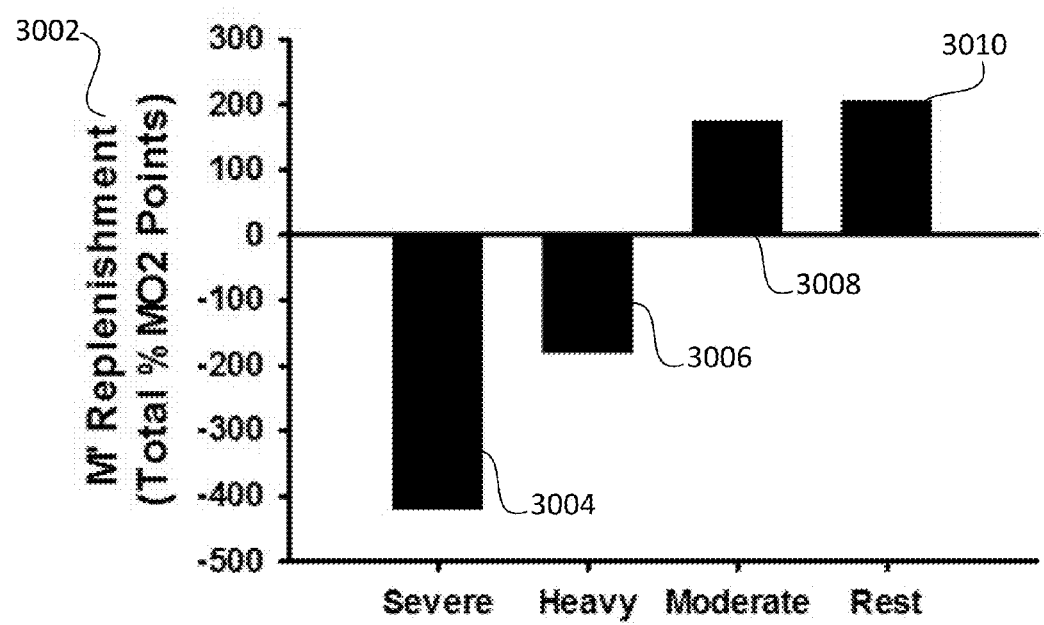
FIG. 30 schematically depicts an anaerobic work capacity replenishment rate, according to one or more aspects described herein.

In one example, an anaerobic work capacity of the user may be replenished when the user exercises at an intensity that is below a critical intensity (i.e. within a moderate or heavy exercise intensity domain). As previously described, an anaerobic work capacity may be expressed as a total number of muscle oxygenation points, as derived from muscle oxygenation sensor data, such as data outputted by oxygenation sensor 710. As such, the anaerobic work capacity may be denoted M'. In one example, replenishment of anaerobic work capacity may be denoted M'_rate and calculated as a difference between a current muscle oxygenation percentage and a critical muscle oxygenation percentage: M'_rate=% MO2−critical % MO2. In one example, the M'_rate may be continuously summed throughout a duration of an exercise period/trial in order to determine an M' balance (i.e. a total number of muscle oxygenation points). Accordingly, when a current muscle oxygenation percentage is below the critical muscle oxygenation percentage, the calculated M'_rate may be negative, and indicative of a finite work capacity (anaerobic work capacity) being consumed. Further, when a current muscle oxygenation percentage is above the critical muscle oxygenation percentage for a user, the M'_rate may be positive, and the finite work capacity may be replenished. FIG. 30 schematically depicts this consumption and replenishment of total muscle oxygenation points. In particular, FIG. 30 graphs M' replenishment on the y-axis 3002 for four different exercise intensity domains (i.e. severe 3004, heavy 3006, moderate 3008 and rest 3010). As such, FIG. 30 schematically demonstrates that an M'_rate associated with a severe exercise intensity domain may be negative, but the anaerobic work capacity of the user may be replenished as the user transitions to exercise within a heavy exercise intensity domain 3006, in a moderate exercise intensity domain 3008, and when the user is at rest 3010.

Various systems and methods are described in this disclosure for calculation of a critical intensity (critical velocity, or a critical power) for a user. Additionally, various systems and methods are described in this disclosure for calculation of an anaerobic work capacity/finite work capacity (M', D') associated with user. As such, given these calculated critical intensity and finite work capacity values, various activity metrics may be predicted. As such, those of ordinary skill in the art will recognize various methodologies that may be utilized predict athletic metrics using one or more of a critical intensity and a finite work capacity for a user, without departing from the scope of these disclosures. In one example a prediction of a time, t (s), to completion of an athletic event (e.g. a race), given a present velocity, $v_p$ (m/s), a critical velocity, $v_{crit}$ (m/s), and a finite work capacity, D' (m), may be given by: $t=D'/(v_p-v_{crit})$.

Utilizing Novel MO2 Parameters

One or more of the above-referenced embodiments related to a Critical Power model, for example, to predict time to exhaustion, including in a real-time environment. One of the example embodiments utilized two a priori inputs of exercise capacity (e.g., critical power and W'). In certain embodiments, one or more of these inputs may not be known readily accessible, measurable, and/or obtained from an accurate and/or precise source, such as under a time constraint.

As one specific example, a limitation (in some situations) to predicting TTE solely from work rate data, and incorporation via a Critical Power Model, which requires a priori defined inputs, is the ignorance of the physiological changes concurrent with long duration exercise. For example, it is well understood in the art that an athlete will fatigue over the course of, for example, 2 hours of heavy exercise, such that exercise capacity variables may no longer be equivalent to that at start of exercise. Novel systems and method disclosed herein overcome this and/or other possible limitations.

Therefore, disclosed herein are additional embodiments. In accordance with certain embodiments, systems and methods may utilize muscle oxygenation output as an input to directly predict time to exhaustion ("TTE") independent of the one or more aforementioned Critical Power model(s). In one embodiment, muscle oxygenation output may be the sole input utilized to determine time to exhaustion. Those skilled in the art will appreciate that time to exhaustion may be calculated by multiple different methodologies, for example, to determine which more closely resembles reality, available sensors and/or data, time constraints, battery or energy level of one or more devices, user preference, and/or other factors.

In accordance with certain implementations, the systems and methods may be applied to, and thus account for different activities. For example, an example implementation may be used to both continuous and intermittent activity, which was not available under prior art methodologies. In some embodiments, time to exhaustion may be calculated from a system/method regardless if the user is exercising or otherwise conducting movements at either, above, below, or at critical intensity. In one embodiment, systems and methods are implemented regardless of both: (1) whether the activity or motions are continuous or intermittent; and (2) whether the activity is above, below or at critical intensity. Thus, disclosed systems and methods account for the mode of exercise and the complete range of exercise intensity. Such implementations may be utilized to predict time to exhaustion in real-time.

In accordance with one embodiment, muscle oxygenation is obtained, measured and/or derived from one or more locations of the user's body during athletic movements. As shown in FIG. 31, muscle oxygenation, alone, can be used to accurately predict, in real time, time to exhaustion. As one example, using the novel systems and methods disclosed herein, time to exhaustion was accurately predicted for a plurality of exercise trials, in which the trails exhibited, when compared to each other, a range of exercise modes and duration as well as intensity.

Figure 31A:
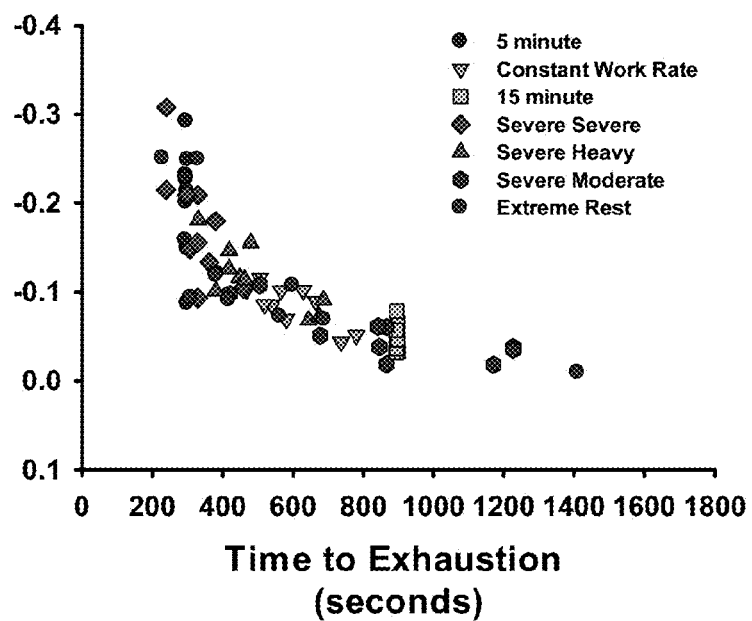
FIGS. 31A-31C are charts of an example embodiment in which average slope of muscle oxygenation for each of a plurality of exercise trials is compared to exhaustion time; specifically.
Figure 31B:
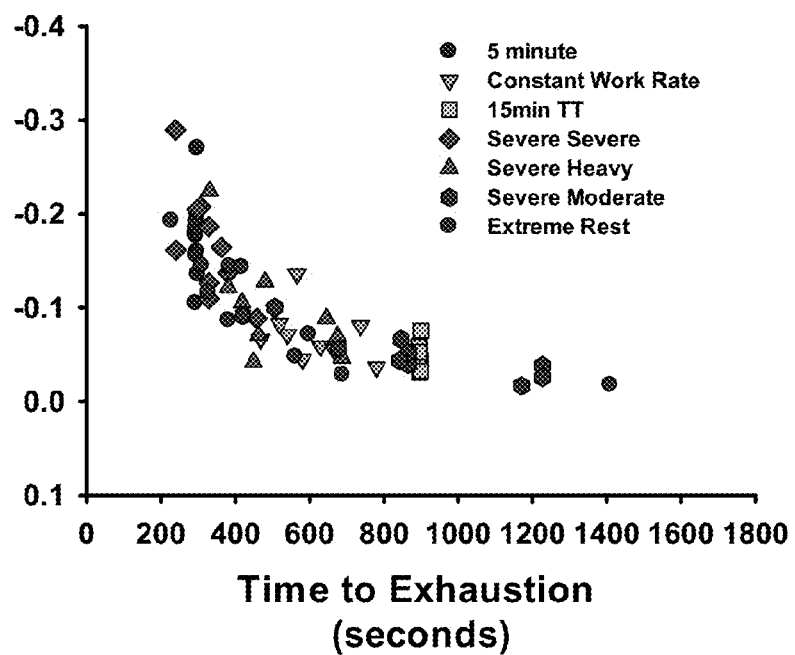
Figure 31C:
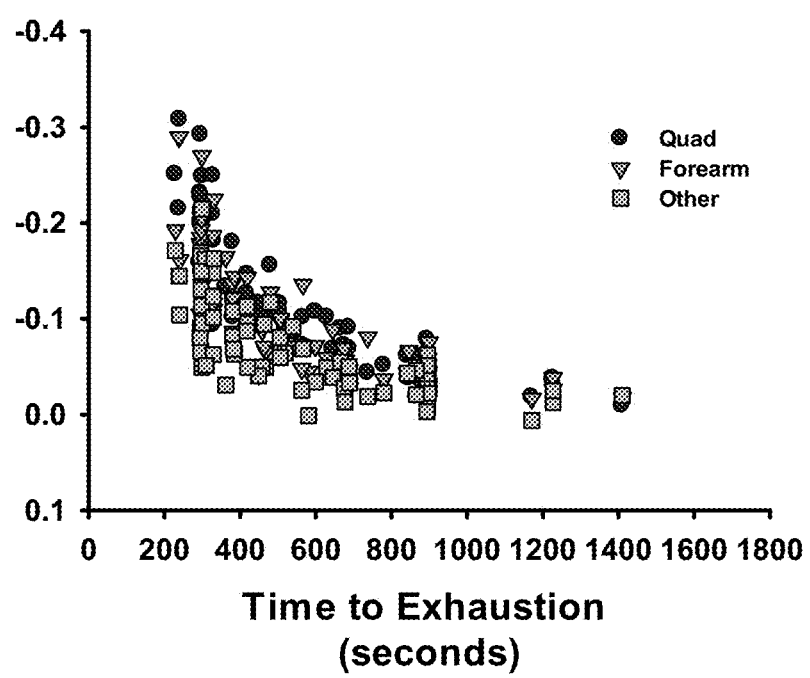

FIG. 31 shows the average slope of the muscle oxygenation (shown along the Y axis) for each of a plurality of exercise trials is compared to exhaustion time (shown along the X axis), in which the trials are diverse with respect to exercise intensities and time to exhaustion durations. Specifically, FIG. 31A shows an average Quad muscle oxygenation slope; FIG. 31B shows the an average forearm muscle oxygenation slope; and FIG. 31C shows average muscle oxygenation slopes from a plurality of different locations, including calf, trapezius, and latissimus dorsi, in addition to plotting both quad and forearm slops. As shown in FIG. 31C, slopes from the different locations are significantly related to time to exhaustion.

The inventors have validated example embodiments of the novel systems and methods. For example, its known that problems of robustness may arise once applied to a secondary dataset not included in original formula development (i.e., an equation validation dataset). The inventors have developed systems and methods that can predict the % muscle oxygenation slope and time to exhaustion (TTE), and therefore, applied thee novel approaches to secondary datasets to confirm validity of exemplary methods.

Figure 32:
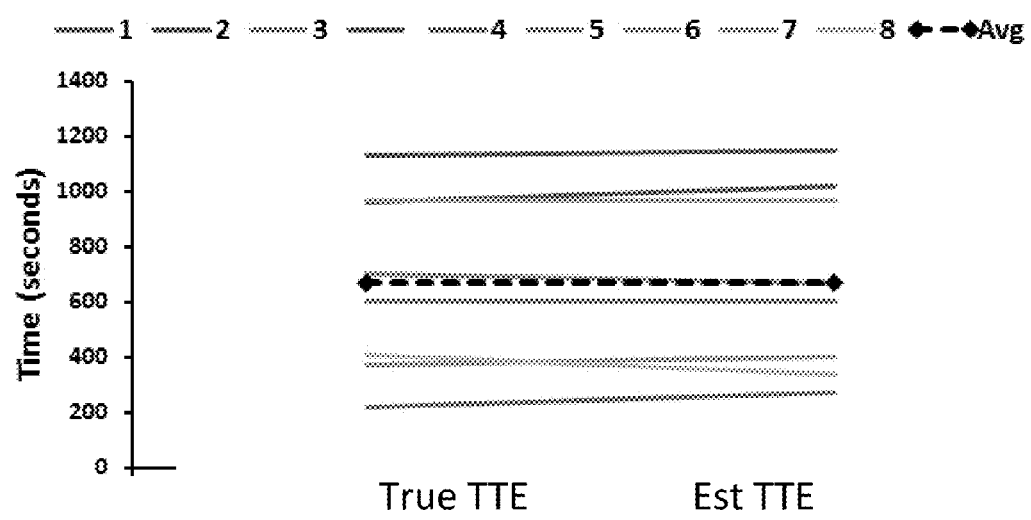
FIG. 32 is a graph demonstrating that, in accordance with one embodiment, a novel MO2-determined TTE was not significantly different than true TTE.

In one example validation, MO2 estimated TTE was compared to True TTE for 8 individuals who each performed intermittent running at variable exercise intensity. As shown in FIG. 32, on average, the novel MO2-determined TTE was not significantly different than true TTE (P<0.05; 671 vs 677 seconds, Δ 6±15 sec or Δ 2±4%). Specifically, when comparing 8 different the time in second (shown on the Y axis) was not significantly different for the True TTE (left hand side of the X axis) when compared with the MO2 estimated TTE.

As discussed above, certain systems and methods require a priori defined inputs, which may introduce the ignorance of the physiological changes concurrent with long duration exercise. For example, it is well understood that an athlete will fatigue over the course of, for example, 2 hours of heavy exercise, such that exercise capacity variables may no longer be equivalent to that at start of exercise. Novel systems and methods overcome this deficiency through the utility of the disclosed embodiments of MO2 TTE determinations. Table 1, shown below, shows two datasets in which true time to exhaustion was measured after 2 hours of exercise, and was also calculated via novel MO2 TTE methods. As shown in table 1, robustness is exhibited in the Mo2 TTE method despite various physiological alterations concurrent with prolonged duration exercise. For example, in dataset 1, the estimated TTE was off my 1.3% and in dataset #2 it was off by 0.5%. TTE may be voluntary exhaustion in which the athlete cannot continue, for example, well-motivated athlete's familiar with exercise type and intensities cannot continue and/or can be confirmed with one or more parameters, such as lactate, maximal heart rate, respiratory exchange rate, and/or other parameters.

TABLE 1

True time to exhaustion and calculated via MO2 TTE method measured after 2 hours of exercise

| Dataset | True TTE | Mo2 Est TTE | Δ seconds | Δ % |
|---------|----------|-------------|-----------|-----|
| #1 | 252 | 249 | 3 | 1.3 |
| #2 | 417 | 415 | 2 | 0.5 |

Figure 33:
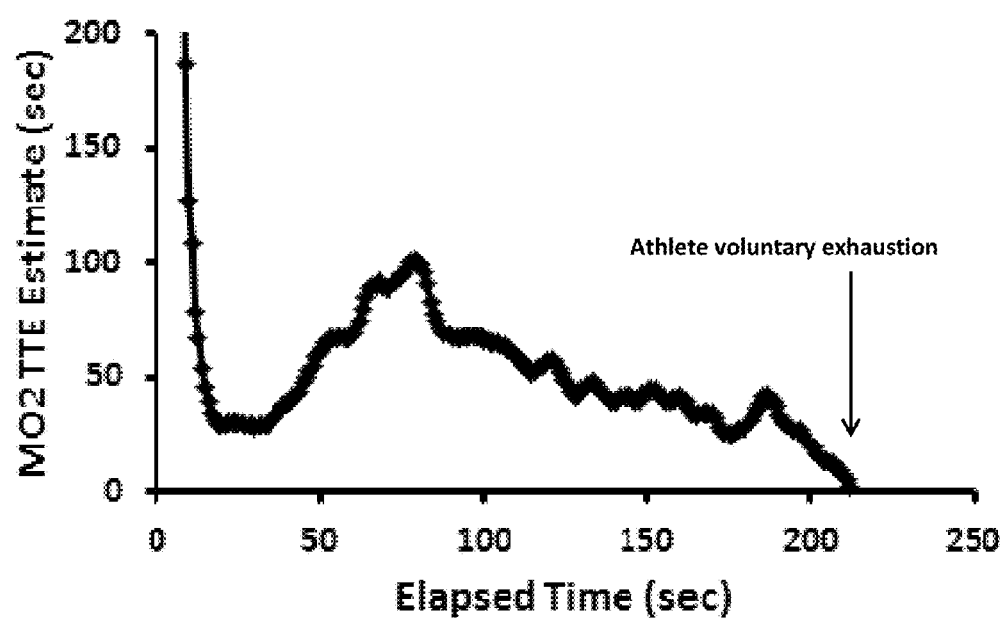
FIG. 33 is a graph depicting example data from exercise performed after 2 hours of fatiguing exercise in which the point of voluntary exhaustion coincides with near zero seconds indicated by the MO2 TTE estimation formulation further demonstrating the accuracy of certain embodiments disclosed herein.

Calculating TTE can be accurately performed in real-time in accordance with certain embodiments. FIG. 33 shows example data from exercise performed after 2 hours of fatiguing exercise. As one embodiment, a user may start a run at 7 MPH, however, later in the run be at 6 MPH. Prior art systems could not accurately predict TTE with such variable intensity. The MO2 TTE estimate is shown on the Y axis and the elapsed time is provided on the X axis. As shown in FIG. 33, the point of voluntary exhaustion coincides with near zero seconds indicated by the MO2 TTE estimation formulation.

Exercise Intensity

Further aspects of the innovation relate to systems and methods may be utilized to predict exercise intensity. In one embodiment, regression of an MO2 signal can be used to predict exercise intensity, and with respect to specific exercise capacities such as Critical Intensity threshold.

Figure 34:
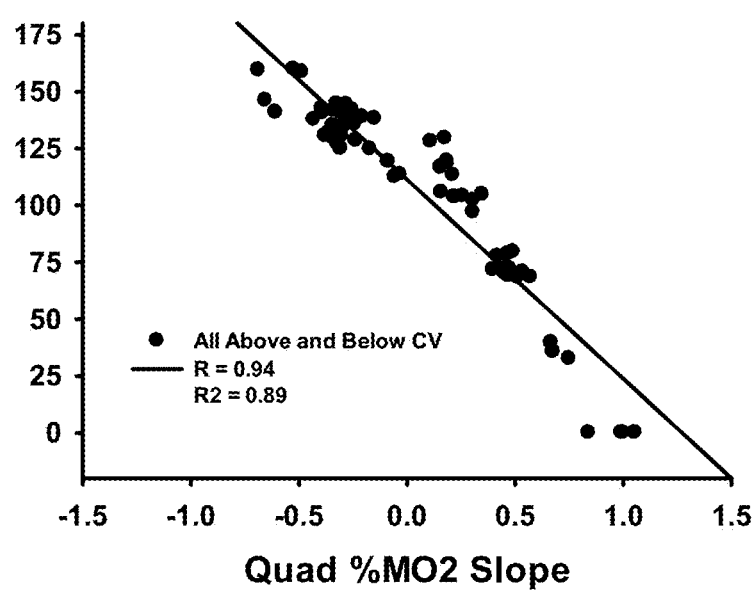
FIG. 34 is a chart showing a correspondence of positive % MO2 slope during work rates below Critical Intensity and negative % MO2 slope during work rates above Critical Intensity in accordance with certain implementations.

As shown in FIG. 34, systems and method may utilize the discovery that a very strong relation exists between the % MO2 slope and the Critical Velocity (e.g. in running) an; similar observations for Critical Power, for activities). As shown in FIG. 34, there is a correspondence of positive % MO2 slope during work rates below Critical Intensity, and negative % MO2 slope during work rates above Critical Intensity. Thus, not merely using MO2, but a specific rate of change of MO2 can be used to predict exercise intensity, and with respect to specific exercise capacities such as Critical Intensity threshold.

As used in certain publications, the term critical intensity may be, at times, synonymous with other language such as, but not limited to, the following: Critical Power, Critical Work Rate, Critical Velocity, Critical Heart Rate, Critical Vo2, Maximal Lactate Steady State, Lactate Threshold, Anaerobic Threshold, Aerobic Threshold, Functional Threshold Power, Ventilatory Threshold, and/or Respiratory Compensation point, however, fatigue can cause on or more of the above parameters deviate from each other, and as such differ which were not addressed by prior art systems in the effective manner provided herein. Aspects of the embodiments disclosed herein relate to, regardless of the 'threshold name,' is the predictive diagnosis of a sustainable vs unsustainable exercise intensity. Further, because MO2 can be used to quantify exercise intensity, as well as time to exhaustion, in accordance with one or more disclosed embodiments, surrogate indicators such as exercise efficiency, running economy, improved performance outcomes via intervention to footwear and/or apparel, can also be predicted. Any or all of the diagnostic parameters could be portrayed to an athlete for behavior modification, or any or all of the diagnostic parameters may act as an input to directly modify footwear and/or apparel in specific manner. For example, it can be used to specifically trigger modifications to footwear, apparel, and equipment.

Apparel Recommendations and Real-Time Adjustments

As noted above, MO2, such as from NIRS, may be utilized in calculations to provide an index for exercise intensity when obtained over either active and/or non-active muscle. To this end, higher intensity exercise is generally associated with greater muscle O2 consumption (i.e. greater change in MO2 value from rest to exercise). Nevertheless, any alteration in muscle O2 consumption for a given work rate can be interpreted in accordance with novel systems and methods, to provide knowledge regarding O2 cost of exercise (i.e. conservation or wastefulness of O2). Decreasing the O2 cost of running for instance is concomitant with delayed time to exhaustion and enhanced sport performance outcomes.

Footwear modifications (such as changing midsole compression stiffness, bending stiffness, midsole geometry, heel-toe offset, forefoot bending stiffness, adjustable air, mass distribution, or upper shape and stiffness/tightness) may be used, in a preventative, prescriptive and/or adaptive manner, to modify gait and muscle recruitment patterns, as well as modify energetic requirements during athletic activity, such as for example, running. The inventors have discovered systems and methods that muscle O2 and/or associated variables can be observably altered and adjusted based upon footwear modifications, thus MO2 may be utilized, in accordance with certain embodiments, as a trigger to provide or implement footwear recommendations and/or 'on-the-fly' footwear adaptations.

Figure 35A:
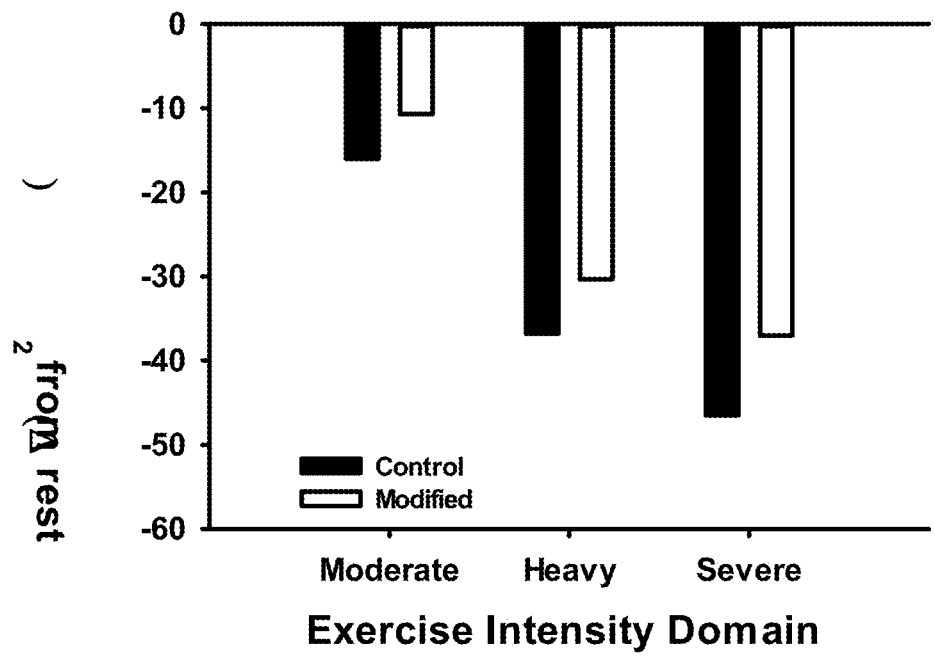
FIGS. 35A-35C are graphs demonstrating how equipment modifications in accordance with certain implementations may extend exhaustion estimates in accordance with one or more embodiments; specifically, FIG. 35A demonstrates greater active muscle O2 consumption across the exercise intensity domains during treadmill running.
Figure 35B:
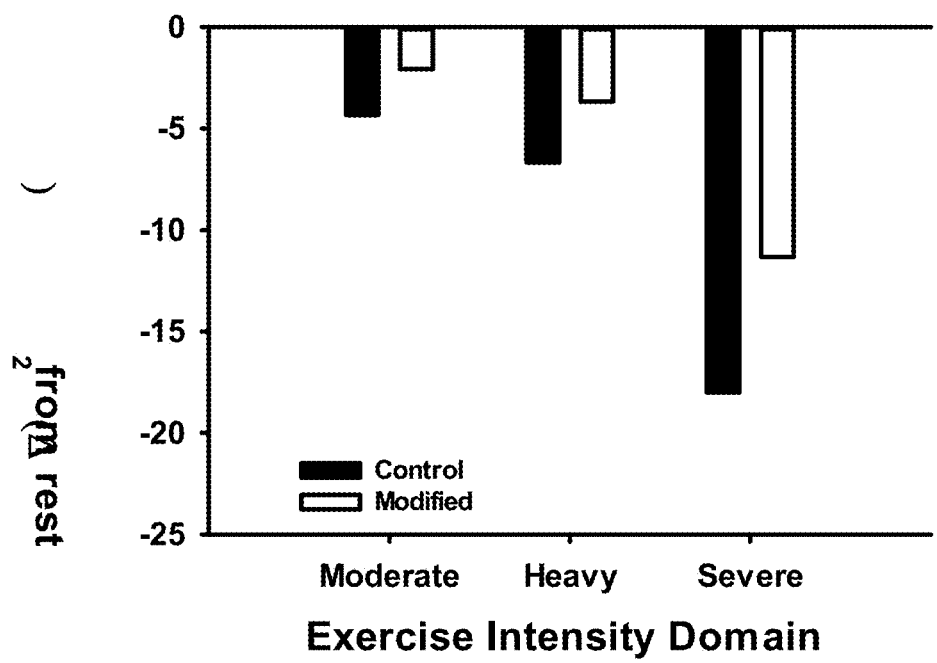
Figure 35C:
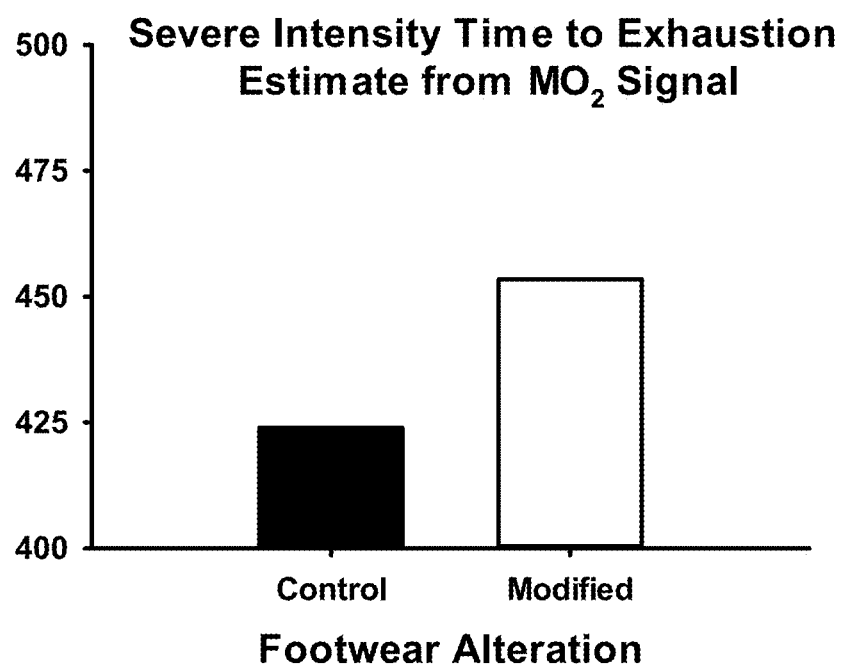

Collectively, FIG. 35 (comprising FIG. 35A-35C) shows how equipment modification may extend exhaustion estimates. Specifically, FIG. 35A provides data demonstrating greater active muscle O2 consumption (measured in the quadriceps) across the exercise intensity domains during treadmill running. When midsole compression stiffness, bending stiffness and midsole geometry is promptly modified within the same exercise session, active muscle O2 consumption is suppressed for a given running intensity, indicating an improved O2 cost of running. FIG. 35B provides similar data and interpretation to FIG. 35A, yet is specific to largely non-active muscle (measured in the forearm). FIG. 35C utilizes the aforementioned process to determine a time to exhaustion estimate from MO2 signals. Note the extended time to exhaustion estimate for the modified shoe condition. Thus, the implementation of novel systems and methods in which MO2 parameters can be used to provide footwear recommendations and act as instantaneous trigger to initiate real-time changes in footwear. Such shifts may enable continuous benefit to athlete performance both during and between training and racing.

Running Recharge Rates

If an athlete performs an athletic activity below their "critical" threshold of intensity, they may "recharge" their ability to perform additional athletic activities. For example, running intensity performed below the athlete's critical speed facilitates recharge of D', where D' is defined as the finite amount of extra distance that can be covered before fatigue occurs when running at speeds above the critical speed. A time constant (Tau) of the recharge rate for D' may be used and be directly related to the difference between the runner's current speed and the runner's critical speed (Dcs).

Aspects herein relate to calculating an exercise mode-specific recharge rate. Additionally, systems and methods may be implemented to utilize the exercise mode-specific recharge rate in a calculation of D' balance, including a real-time calculation if desired, where D' balance is essentially the amount of D' available to the athlete at any point in time. With D' balance information, systems and methods may be implemented to make real-time paces changes in order to optimize performance and prevent untimely fatigue.

Disclosed herein are systems and methods relating to the development of a Tau constant specific to the running exercise modality. To that end, a population based method is described below such method can be applied on an individual basis to specifically identify specific rates of D' recharge.

Example 1—Running

The D' expended at any point in time is calculated using the following equation:

$$dPrimeExpended = flipDcsArray * e^{(-timeIndexArray/Tau)};$$

$$Tau = 1431 * e^{(2.145 * Dcs)} + 420;$$

Figure 36:
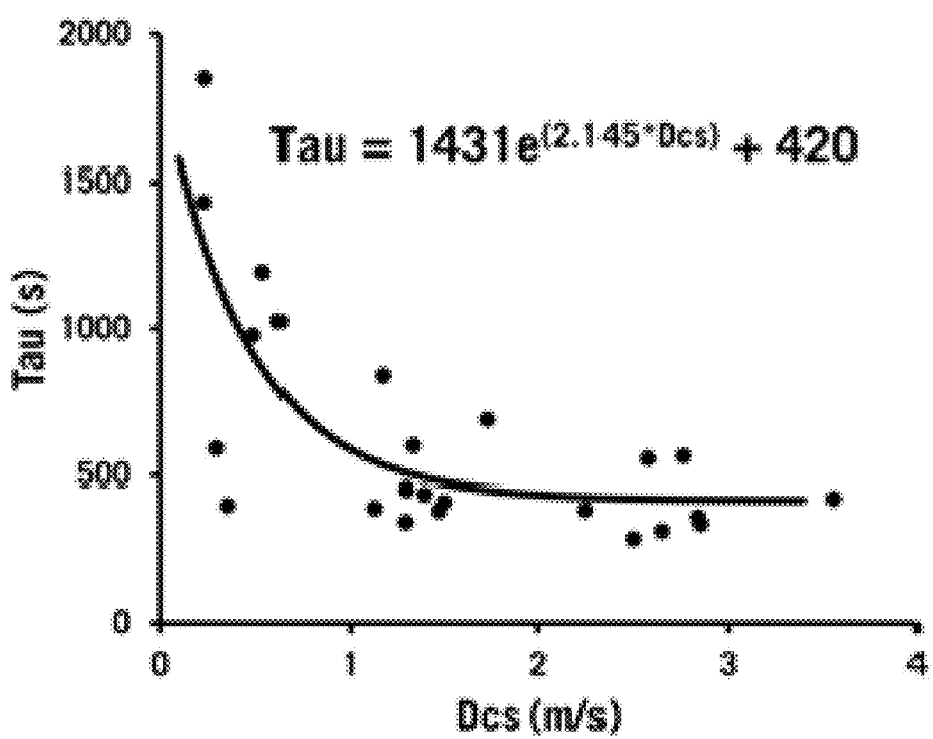
FIG. 36 is a chart depicting the time of D' recharge being exponentially related to the delta of critical speed from instantaneous speed in accordance with one embodiment.

As shown in the example chart of FIG. 36, the time of D' recharge in seconds is exponentially related to the delta of critical speed from instantaneous speed in accordance with one embodiment.

An alternative method to calculate the rate of D' recharge during running is as follows:

Example 2—Running

The D' expended at any point in time is calculated using the following equations:

If current speed>critical speed $$dPrimeExpended = currentDPrimeExpended + (Dcs * windowTime)$$

else if current speed<critical speed $$dPrimeExpended = currentDPrimeExpended * e^{(k * Tau)}$$

else current speed=critical speed $$dPrimeExpended = currentDPrimeExpended$$

$k$=model tuning constant $$Tau = dPrime/Dcs;$$

Figure 37:
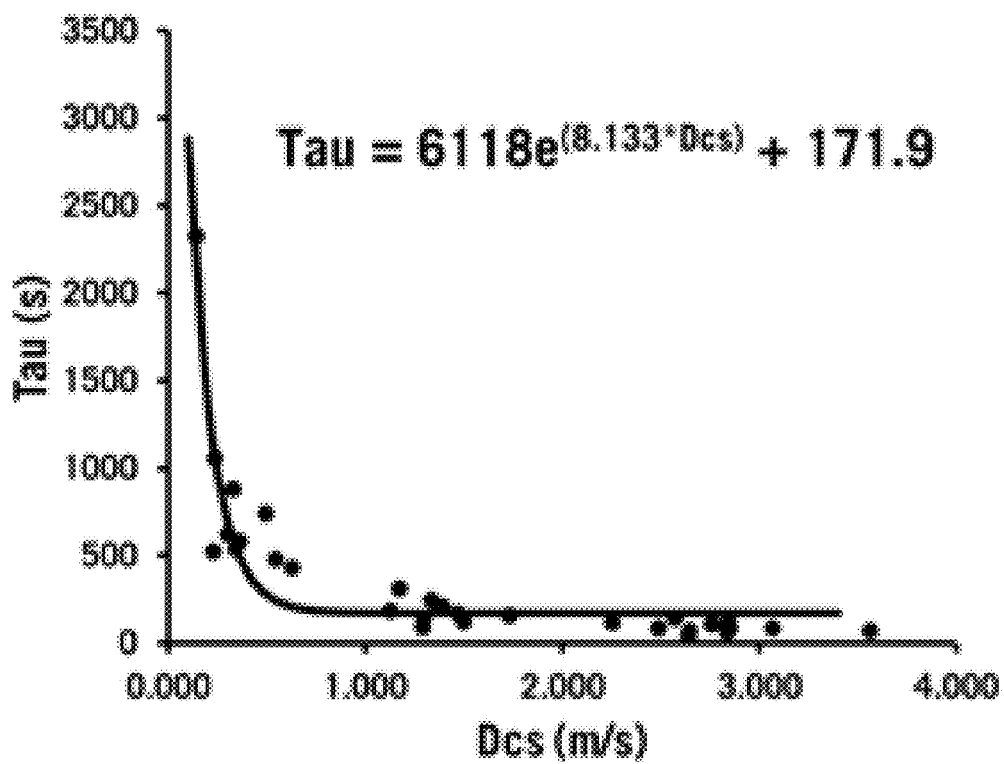
FIG. 37 shows a chart illustrating an alternative embodiment to FIG. 36, that may be used, for example, when dPrime is not known.

FIG. 37 shows a chart illustrating an alternative formulation, that may be used for example, when dPrime is not known.

$$Tau = 6118 * e^{(8.133 * Dcs)} + 171.9$$

A rate of D' recharge (i.e. as illustrated in either tau equation noted above—and shown in FIGS. 36 and 37 respectively) during running may be calculated and thus allows calculation of D' balance, which is considered the fluid amount of D' remaining, regardless of exercise intensity. As an illustrative example, in terms of percentage, once a D' balance of zero percent is reached, the athlete is either at the point of exhaustion or must significantly 'rest' below critical velocity in order to again recharge the D' according to the running tau.

Figure 38A:
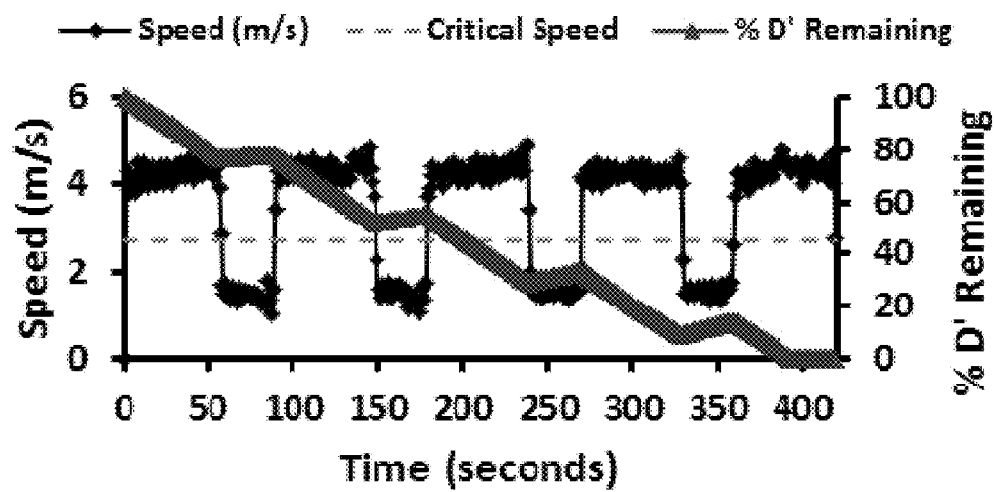
FIGS. 38A-38B show example charts providing data of an athlete running intermittently at instantaneous speeds in which the rate of D' recharge is directly related to the specific running tau formulation and numeric; Specifically, in the example of FIG. 38A, note the alignment of exhaustion at 420 seconds and a % D remaining of near zero.
Figure 38B:
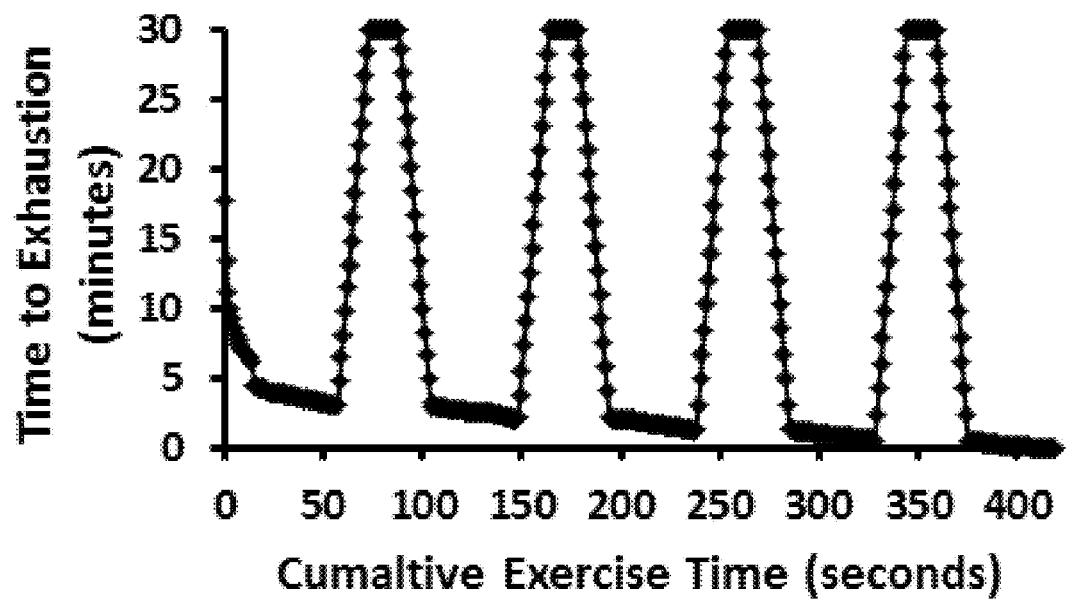
Figure 28:
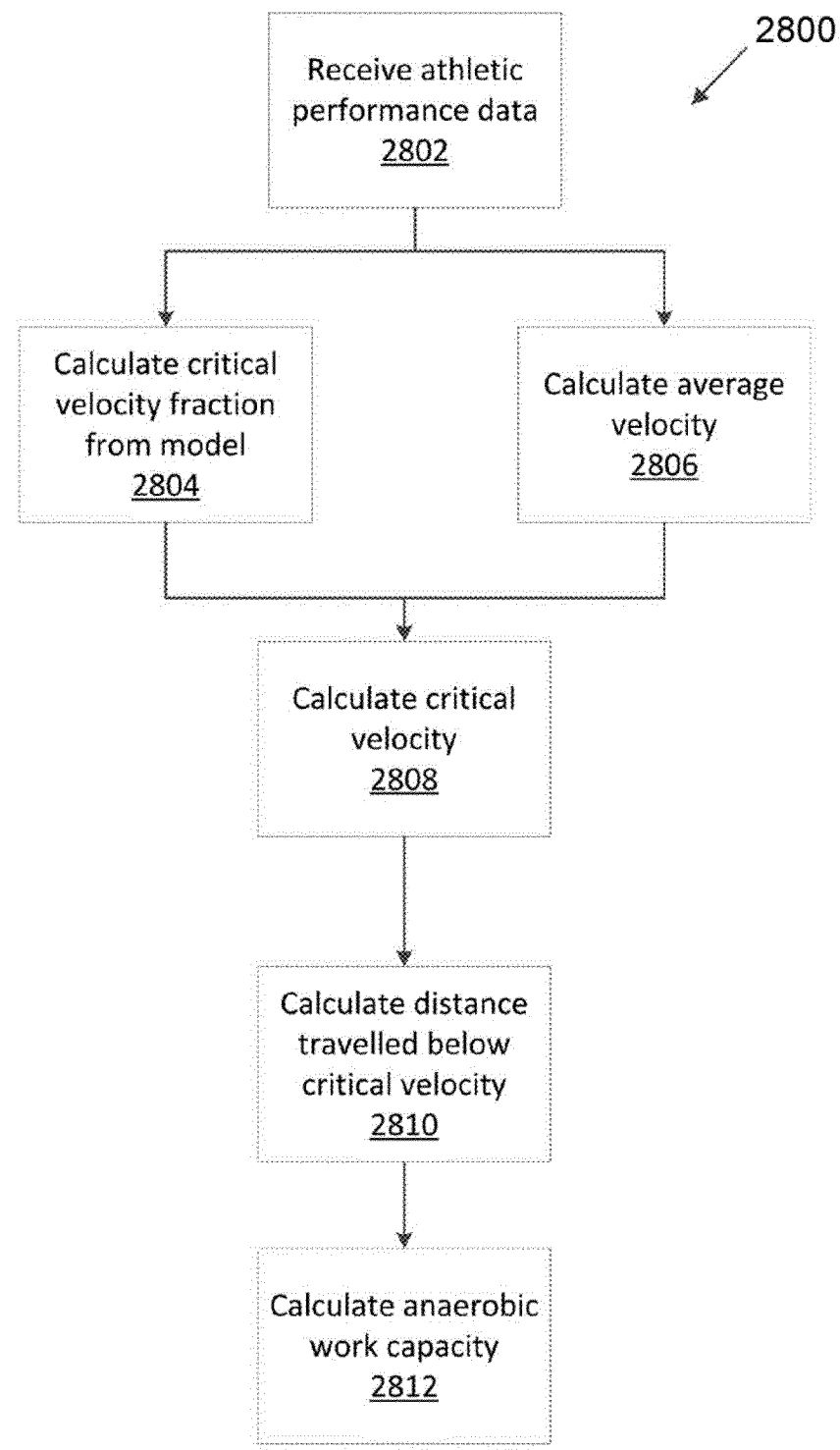
Figure 29:
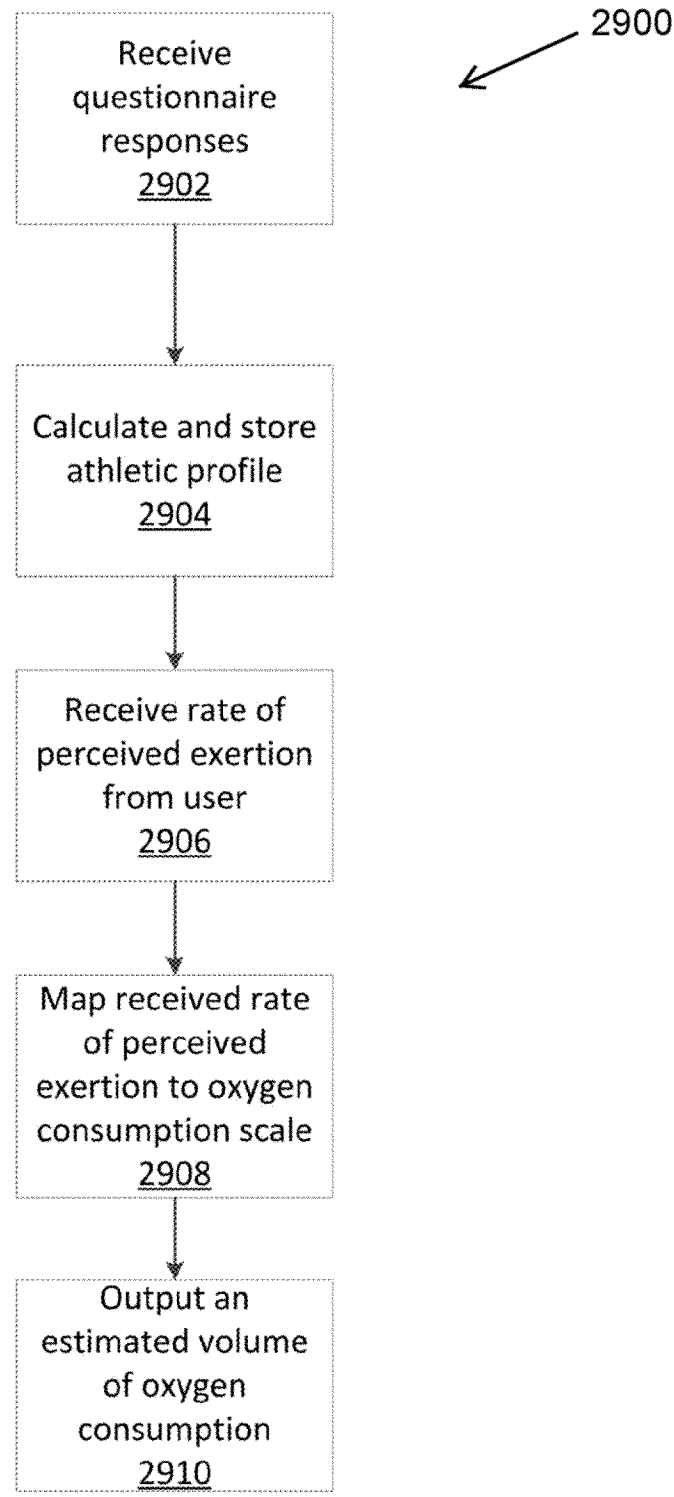

FIG. 38A shows a chart of an example athlete running intermittently at instantaneous speeds (shown by the solid line depicting speeds between just above 4 MPH and below 2 MPH). As further seen in FIG. 38A, such speeds are both above and below the critical speed (denoted with the dotted line) until exhaustion. As seen by the line extending from the upper left side of FIG. 38A to the lower right side, D' is rapidly depleted when running faster than critical speed, but slowly recharged when below critical speed. The rate of D' recharge is directly related to the specific running tau formulation and numeric. In the example of FIG. 38A, note the alignment of exhaustion at 420 seconds and a % D remaining of near zero. As shown in FIG. 38B, the instantaneous D' remaining is converted into units of time for easy display and athlete understanding.

For the avoidance of doubt, the present application extends to the subject-matter described in the following numbered paragraphs (referred to as "Para" or "Paras"). To avoid unnecessary duplication of effort and repetition of text, certain features are described in relation to only one or several aspects, embodiments or Paragraphs. However, it is to be understood that, where it is technically possible, features described in relation to any aspect, embodiment or Paragraph may also be used with any other aspect, embodiment or Paragraph, however, for simplicity purposes reference back to a particular paragraph or clause can be interpreted to the respective clause or paragraph within the same group.

Group 1:
1. An apparatus, comprising:
   a processor;
   a user interface;
   an oxygenation sensor, configured to be positioned proximate an area of skin of a user, the oxygenation sensor further configured to output data indicative of a tissue oxygenation of a body tissue of the user; and
   a non-transitory computer-readable medium comprising computer-executable instructions that when executed by the processor are configured to perform at least:
      receive tissue oxygenation data from the oxygenation sensor associated with at least two exercise periods, at least a portion of each of the at least two exercise periods associated with a severe exercise intensity domain, and the at least two exercise periods having differing durations;
      calculate a total number of tissue oxygenation points for each of the at least two exercise periods;
      calculate an exercise period summary data point for each of the at least two exercise periods as a total number of tissue oxygenation points versus a duration of exercise;
      calculate a regression through the exercise period summary data points for the at least two exercise periods;
      output a critical tissue oxygenation percentage for the user equal to a slope of at least a portion of the regression, and/or output an anaerobic work capacity equal to an intercept associated with at least a portion of the regression.
2. An apparatus according to Para 1, wherein the total number of tissue oxygenation points for each of the at least two exercise periods are calculated as an integration of tissue oxygenation percentages for each second of a duration of an exercise period, from the at least two exercise periods.
3. The apparatus of Para 1 or 2, wherein the computer-readable instructions, when executed by the processor, further cause the apparatus to:
      receive data, from the oxygenation sensor, indicating an additional tissue oxygenation percentage associated with an additional exercise period; and
      compare the additional tissue oxygenation percentage to the critical tissue oxygenation percentage,
      wherein:
      if the additional tissue oxygenation percentage is less than the critical tissue oxygenation, output, to the user interface, a signal indicating that the user is exercising at an unsustainable work rate, and/or
      if the additional tissue oxygenation percentage is greater than or equal to the critical tissue oxygenation, output, to the user interface, a signal indicating that the user is exercising at a sustainable work rate.
4. The apparatus of any of the preceding Paras, wherein the computer-readable instructions, when executed by the processor, further cause the apparatus to:
      receive data, from the oxygenation sensor, indicating an additional tissue oxygenation percentage associated with an additional exercise;
      receive an indication of a distance associated with the additional exercise; and
      calculate an expected time to completion of the additional exercise, based on the calculated critical tissue oxygenation.
5. The apparatus of any of the preceding Paras, wherein the oxygenation sensor utilizes near infra-red spectroscopy.
6. The apparatus of any of the preceding Paras, wherein the body tissue is a muscle.
7. The apparatus of Para 6, wherein the muscle is classified as an inactive muscle for the type of exercise undertaken by the user for the at least two exercise periods.
8. The apparatus of any of the preceding Paras, wherein the apparatus is configured to be worn on an appendage of a user.
9. The apparatus of any of the preceding Paras, wherein the regression is a linear regression.
10. The apparatus of any of the preceding Paras, wherein the regression is a curvilinear regression.
11. An apparatus, comprising:
    a processor;
    an oxygenation sensor, configured to be positioned proximate an area of skin of a user, the oxygenation sensor further configured to output data indicative of a tissue oxygenation of a body tissue of the user; and
    a non-transitory computer-readable medium comprising computer-executable instructions that when executed by the processor are configured to perform at least:
       receive periodic data from the oxygenation sensor indicative of a tissue oxygenation percentage of the body tissue of the user;
       calculate a tissue oxygenation trend using two or more received tissue oxygenation data points,
       wherein:
       if the tissue oxygenation trend is negative, output a signal indicating that the user is exercising at an unsustainable work rate,
       if the tissue oxygenation trend is positive, output a signal indicating that the user is exercising at a sustainable work rate, and/or
       if the tissue oxygenation trend is level, output a signal indicating that the user is exercising at a critical work rate.
12. The apparatus of Para 11, wherein if a negative tissue oxygenation trend has an absolute value above a threshold value, output a signal indicating that the user is exercising at a severe intensity above a critical power for the user.

13. The apparatus of Para 11 or 12, wherein if the tissue oxygenation trend is level, output a critical tissue oxygenation percentage equal to a tissue oxygenation percentage corresponding to the level tissue oxygenation trend.
14. The apparatus of any of Paras 11 to 13, wherein the tissue oxygenation trend is calculated as a change in tissue oxygenation percentage equal to a difference between a current rolling average tissue oxygenation and a previous rolling average tissue oxygenation.
15. The apparatus of any of Paras 11 to 14, wherein the tissue oxygenation trend is level when a change in tissue oxygenation percentage is less than a threshold change value for at least a threshold time.
16. The apparatus of Para 15, wherein the threshold change value is 0.1% and the threshold time is 3 seconds.
17. The apparatus of any of Paras 11 to 16, wherein the body tissue is a muscle.
18. The apparatus of any of Paras 11 to 17, wherein the oxygenation sensor utilizes near infra-red spectroscopy.
19. The apparatus of any of Paras 11 to 18, wherein the apparatus is configured to be worn on an appendage of a user.
20. A method, comprising:
  receiving, by a processor, sensor data from an oxygenation sensor indicative of a tissue oxygenation percentage of a body tissue of a user;
  calculating, by the processor, a tissue oxygenation trend using two or more received tissue oxygenation data points,
  wherein:
  if the tissue oxygenation trend is negative, outputting a signal indicating that the user is exercising at an unsustainable work rate,
  if the tissue oxygenation trend is positive, outputting a signal indicating that the user is exercising at a sustainable work rate, and/or
  if the tissue oxygenation trend is level, outputting a signal indicating that the user is exercising at a critical work rate.
21. The method of Para 20, wherein the tissue oxygenation trend is calculated as a change in tissue oxygenation percentage equal to a difference between a current rolling average tissue oxygenation and a previous rolling average tissue oxygenation.
22. The method of Para 20 or 21, wherein if a negative tissue oxygenation trend has an absolute value above a threshold value, output a signal indicating that the user is exercising at a severe intensity above a critical power for the user.

The present application also extends to the subject-matter described in the following numbered paragraphs (referred to as "Para" or "Paras"):

Group 2:
1. An apparatus, comprising:
  a processor;
  an interface;
  an oxygenation sensor, configured to be positioned proximate an area of skin of a user, the oxygenation sensor further configured to output data indicative of a tissue oxygenation of a body tissue of the user;
  a power sensor configured to output data indicative of a power consumption of the user; and
  a non-transitory computer-readable medium comprising computer-executable instructions that when executed by the processor are configured to perform at least:
  receive tissue oxygenation data from the oxygenation sensor during an exercise session comprising at least a portion of a total exercise time exercising within a severe exercise intensity domain;
  calculate a change in tissue oxygenation as a difference between a current tissue oxygenation value and a previous tissue oxygenation value; and
  compare the change in tissue oxygenation to a threshold change value and a threshold duration,
  wherein:
  if the change in tissue oxygenation is less than or equal to the threshold change value, and a change in tissue oxygenation persists for a first duration greater than or equal to the threshold duration, output a signal to the interface indicating a critical power value equal to a current power indicated by the power sensor, and/or
  if the change in tissue oxygenation is greater than the threshold change value or the change in tissue oxygenation persists for a second duration less than the threshold duration, output a signal to the interface indicating that the current power indicated by the power sensor is not equal to the critical power of the user.
2. The apparatus of Para 1, wherein the current tissue oxygenation value and the previous tissue oxygenation value are rolling averages of tissue oxygenation data points received from the oxygenation sensor during a rolling average duration.
3. The apparatus of Para 2, wherein the rolling average duration is at least two seconds.
4. The apparatus of any of the preceding Paras, wherein the body tissue is a muscle.
5. The apparatus of any of the preceding Paras, wherein the oxygenation sensor utilizes near infra-red spectroscopy.
6. The apparatus of any of the preceding Paras, wherein the apparatus is configured to be worn on an appendage of a user.
7. The apparatus of any of the preceding Paras, wherein the computer-readable instructions, when executed by the processor, further cause the apparatus to:
  calculate, an anaerobic work capacity for the user equal to a summation of a plurality of positive difference values for the total exercise time, wherein a difference value is equal to a difference between an output power value from the power sensor and the critical power value.
8. An apparatus, comprising:
  a processor;
  an interface;
  an oxygenation sensor, configured to be positioned proximate an area of skin of a user, the oxygenation sensor further configured to output data indicative of a tissue oxygenation of a body tissue of the user;
  a power sensor configured to output data indicative of a power consumption of the user; and
  a non-transitory computer-readable medium comprising computer-executable instructions that when executed by the processor are configured to perform at least:
  receive tissue oxygenation data from the oxygenation sensor during an exercise session comprising at least a portion of a total exercise time exercising within a severe exercise intensity domain;
  calculate a change in tissue oxygenation as a difference between a current tissue oxygenation value and a previous tissue oxygenation value; and
  compare the change in tissue oxygenation to a threshold change value, wherein:
if the change in tissue oxygenation is less than or equal to the threshold change value, output a signal to the interface indicating a critical power value equal to a current power indicated by the power sensor, and/or
if the change in tissue oxygenation is greater than the threshold change value, output a signal to the interface indicating that the current power indicated by the power sensor is not equal to the critical power of the user.

9. The apparatus of Para 8, wherein the power sensor comprises an accelerometer.

10. The apparatus of Para 8 or 9, wherein the power sensor comprises a dynamometer.

11. The apparatus of any of Paras 8 to 10, wherein the interface comprises a graphical user interface.

12. The apparatus of any of Paras 8 to 11, wherein the interface comprises a transceiver.

13. The apparatus of any of Paras 8 to 12, wherein the computer-readable instructions, when executed by the processor, further cause the apparatus to:
calculate, an anaerobic work capacity for the user equal to a summation of a plurality of positive difference values for the total exercise time, wherein a difference value is equal to a difference between an output power value from the power sensor and the critical power value.

14. The apparatus of any of Paras 8 to 13, wherein the body tissue is an active muscle for the exercise session.

15. The apparatus of any of Paras 8 to 13, wherein the body tissue is an inactive muscle for the exercise session.

16. A non-transitory computer-readable medium comprising computer-executable instructions that when executed by a processor are configured to perform at least:
receive, from an oxygenation sensor, tissue oxygenation data during an exercise session comprising at least a portion of a total exercise time exercising within a severe exercise intensity domain;
calculate a change in tissue oxygenation as a difference between a current tissue oxygenation value and a previous tissue oxygenation value; and
compare the change in tissue oxygenation to a threshold change value,
wherein:
if the change in tissue oxygenation is less than or equal to the threshold change value, output a signal to an interface indicating a critical power value equal to a current power indicated by the power sensor, and
if the change in tissue oxygenation is greater than the threshold change value, output a signal to the interface indicating that the current power indicated by the power sensor is not equal to the critical power of the user.

17. The non-transitory computer-readable medium of Para 16, wherein the current tissue oxygenation value and the previous tissue oxygenation value are rolling averages of tissue oxygenation data points received from the oxygenation sensor during a rolling average duration.

18. The non-transitory computer-readable medium of Para 17, wherein the rolling average duration is at least two seconds.

19. The non-transitory computer-readable medium of any of Paras 16 to 18, wherein the oxygenation sensor utilizes near infra-red spectroscopy.

20. The non-transitory computer-readable medium of any of Paras 16 to 19, wherein the rolling average duration is ranges between least 1 and 10 seconds.

The present application also extends to the subject-matter described in the following numbered paragraphs (referred to as "Para" or "Paras"):

Group 3:

1. An apparatus, comprising:
a processor;
a sensor; and
a non-transitory computer-readable medium comprising computer-executable instructions that when executed by the processor are configured to perform at least:
receive a plurality of sensor data points from the sensor, the plurality of sensor data points each indicating an instantaneous speed of a user during an exercise session, the exercise session having a prescribed duration between a start time and an end time;
calculate an end speed of the user at the end of the prescribed duration of the exercise session;
calculate a distance above end speed as a total distance traveled by the user at an instantaneous speed above the calculated end speed between the start time and end time of the prescribed duration of the exercise session;
output a critical speed of the user based on the calculated end speed, and/or output an anaerobic work capacity based on the calculated distance above end speed.

2. The apparatus of Para 1, wherein the end speed of the user is calculated as an average of a sub-set of the plurality of periodic sensor data points received during an end portion of the exercise session.

3. The apparatus of Para 2, wherein the end portion of the prescribed duration of the exercise session comprises a last 30 seconds of the prescribed duration.

4. The apparatus of any of the preceding Paras, wherein the critical speed is calculated, by the processor, as 90-95% of the calculated end speed.

5. The apparatus of any of the preceding Paras, wherein the anaerobic work capacity is calculated as 125-135% of the calculated distance above end speed.

6. The apparatus of any of the preceding Paras, wherein the plurality of sensor data points are periodic.

7. The apparatus of any of the preceding Paras, wherein the exercise session comprises a prescribed duration of 2-5 minutes.

8. The apparatus of any of the preceding Paras, wherein the exercise session comprises a prescribed duration of approximately 3 minutes.

9. The apparatus of any of the preceding Paras, wherein the exercise session further prescribes that the user exercises at a highest subjective intensity level for the prescribed duration.

10. The apparatus of any of the preceding Paras, wherein the sensor comprises an accelerometer.

11. The apparatus of any of the preceding Paras, wherein the sensor comprises a location-determining sensor.

12. An apparatus, comprising:
a processor;
a sensor; and
a non-transitory computer-readable medium comprising computer-executable instructions that when executed by the processor are configured to perform at least:
receive data from the sensor associated with at least two exercise periods, at least a portion of the at least two exercise periods associated with a severe exercise intensity domain, and having differing durations;

calculate an exercise period summary data point for each of the at least two exercise periods as a total distance traveled versus a duration of exercise;

calculate a regression through the exercise period summary data points for the at least two exercise periods;

output a critical speed for the user equal to a slope of at least a portion of the regression, and/or output an anaerobic work capacity equal to an intercept associated with at least a portion of the regression.

13. The apparatus of Para 12, wherein the computer-readable instructions, when executed by the processor, further cause the apparatus to:

receive data, from the sensor, indicating a speed associated with an additional exercise period; and compare the speed to the critical speed, wherein:

if the speed is greater than the critical speed output a signal indicating that the user is exercising at an unsustainable work rate, and/or if the speed is less than or equal to the critical speed, output a signal indicating that the user is exercising at a sustainable work rate.

14. The apparatus of Para 12 to 13, wherein the sensor is a location-determining sensor.

15. The apparatus of any of Paras 12 to 14, wherein the sensor is an accelerometer.

16. The apparatus of any of Paras 12 to 15, wherein the apparatus is configured to be worn on an appendage of a user.

17. The apparatus of any of Paras 12 to 16, wherein the regression is a linear regression.

18. The apparatus of any of Paras 12 to 17, wherein the regression is a curvilinear regression.

19. A method, comprising:

receiving, by a processor, a plurality of sensor data points from a sensor, the plurality of sensor data points indicating a speed of a user at a plurality of time periods during an exercise session, the exercise session having a prescribed duration between a start time and an end time;

calculating, by the processor, an end speed of the user at the end of the exercise session;

calculating, by the processor, a distance above end speed as a total distance traveled by the user at a speed above the calculated end speed between the start time and end time of the prescribed duration of the exercise session;

output a critical speed of the user based on the calculated end speed, and/or output an anaerobic work capacity based on the calculated distance above end speed.

20. The method of Para 19, wherein the end speed of the user is calculated as an average of a sub-set of the plurality of periodic sensor data points received during an end portion of the exercise session.

21. The method of Para 20, wherein the end portion of the prescribed duration of the exercise session comprises a last 30 seconds of the prescribed duration.

22. The method of any of Paras 19 to 21, wherein the critical speed is calculated, by the processor, as 90-95% of the calculated end speed.

23. The method of any of Paras 19 to 22, wherein the anaerobic work capacity is calculated as 125-135% of the calculated distance above end speed.

24. The method of any of Paras 19 to 23, wherein the plurality of sensor data points are periodic.

25. The method of any of Paras 19 to 24, wherein the exercise comprises a prescribed duration of 2-5 minutes.

26. The method of any of Paras 19 to 25, wherein the exercise session comprises a prescribed duration of approximately 3 minutes.

27. The method of any of Paras 19 to 26, wherein the exercise session further prescribes that the user exercises at a highest subjective intensity level for the prescribed duration.

The present application also extends to the subject-matter described in the following numbered paragraphs (referred to as "Para" or "Paras"):

Group 4:

1. A method, comprising:

receiving a data point from a user indicative of an athletic performance distance, d, and athletic performance time, t;

calculating a critical velocity fraction, $CV_{fraction}$, based on the athletic performance time and activity type;

calculating an average velocity for the user as the athletic performance distance divided by the time; and calculating a critical velocity for the user equal to the average velocity divided by the critical velocity fraction, wherein $CV_{fraction}$ is approximately equal to $2*t^{-0.1}$ for the activity type corresponding to running.

2. The method of Para 1, wherein the CVfraction is approximately equal to $1.9*t-0.08$.

3. The method of Para 1, wherein the CVfraction is approximately equal to $1.87*t-0.082$.

4. The method of Para 1, wherein the CVfraction is approximately equal to $1.868*t-0.082$.

5. The method of Para 1, wherein the CVfraction is approximately equal to $1.8677*t-0.082$.

6. The method of any of the preceding Paras, further comprising:

calculating a distance traveled below the critical velocity as the average velocity multiplied by the athletic performance time; and calculating an anaerobic work capacity equal to the athletic performance distance minus the distance traveled below the critical velocity.

7. A method, comprising:

receiving a data point from a user indicative of an athletic performance distance, d, and athletic performance time, t;

calculating a critical velocity fraction, $CV_{fraction}$, based on the athletic performance distance and activity type;

calculating an average velocity for the user as the athletic performance distance divided by the time; and calculating a critical velocity for the user equal to the average velocity divided by the critical velocity fraction, wherein $CV_{fraction}=2*d^{-0.1}$ for the activity type corresponding to running.

8. The method of Para 7, wherein the $CV_{fraction}$ is approximately equal to $2.2*d^{-0.09}$.

9. The method of Para 7, wherein the $CV_{fraction}$ is approximately equal to $2.24*d^{-0.09}$.

10. The method of Para 7, wherein the $CV_{fraction}$ is approximately equal to $2.240*d^{-0.09}$.

11. The method of Para 7, wherein the $CV_{fraction}$ is approximately equal to $2.2398*d^{-0.09}$.

12. A method, comprising:

receiving a data point from a user indicative of an athletic performance power, p, and athletic performance time, t;

calculating a critical power fraction, $CP_{fraction}$, based on the athletic performance time and activity type;

calculating an average power for the user as the athletic performance power divided by the time; and calculating a critical power for the user equal to the average power divided by the critical power fraction, wherein $CP_{fraction}=2*t^{-0.1}$ for the activity type corresponding to cycling.

13. The method of Para 12, wherein the $CP_{fraction}$ is approximately equal to $1.9*t^{-0.08}$.
14. The method of Para 12, wherein the $CP_{fraction}$ is approximately equal to $1.92*t^{-0.088}$.
15. The method of Para 12, wherein the $CP_{fraction}$ is approximately equal to $1.920*t^{-0.088}$.
16. The method of Para 12, wherein the $CP_{fraction}$ is approximately equal to $1.9199*t^{-0.088}$.
17. A method, comprising:
   receiving a data point from a user indicative of an athletic performance power, p, and athletic performance time, t;
   calculating a critical power fraction, $CP_{fraction}$, based on the athletic performance power and activity type;
   calculating an average power for the user as the athletic performance power divided by the time; and
   calculating a critical power for the user equal to the average power divided by the critical power fraction, wherein $CP_{fraction}=3*p^{-0.1}$ for the activity type corresponding to cycling.
18. The method of Para 17, wherein the $CP_{fraction}$ is approximately equal to $3.1*p^{-0.08}$.
19. The method of Para 17, wherein the $CP_{fraction}$ is approximately equal to $3.09*p^{-0.086}$.
20. The method of Para 17, wherein the $CP_{fraction}$ is approximately equal to $3.089*p^{-0.086}$.
21. The method of Para 17, wherein the $CP_{fraction}$ is approximately equal to $3.0889*p^{-0.086}$.

The present application also extends to the subject-matter described in the following numbered paragraphs (referred to as "Para" or "Paras"):

Group 5:
1. A method, comprising:
   receiving questionnaire responses from a user;
   calculating and storing a user athletic profile based on the questionnaire responses;
   receiving a rate of perceived exertion value from the user following an exercise session;
   mapping the rate of perceived exertion value to an oxygenation consumption scale, based upon the stored athletic profile; and
   outputting an estimated volume of oxygen consumption of the user, based upon the mapping.
2. A method of Para 1, wherein the questionnaire asks a user to estimate one or more attributes selected from questions consisting of: an estimation of bone size, an estimation of leanness of the user, an estimation of muscle size, an estimation of sleep quality, an estimation of relaxation habits, an estimation of nutrition quality, an estimation of smoking status, an estimation of drinking habits, and an estimation of an activeness of the user, the user's age, gender, height, waist circumference, weight, an indication as to whether the user is pregnant, an estimation of a 5 km running race pace, and an estimation of a number of days active during the week.

We claim:
1. An apparatus, comprising:
   a processor;
   an interface;
   an equipment device;
   an oxygenation sensor, configured to be positioned proximate an area of skin of a user, the oxygenation sensor further configured to output data indicative of a tissue oxygenation of a body tissue of the user;
   a non-transitory computer-readable medium comprising computer-executable instructions that when executed by the processor are configured to perform at least:
      receive tissue oxygenation data from the oxygenation sensor during an exercise session comprising at least a first portion comprising an intermittent activity;
      calculate a change in tissue oxygenation as a difference between a current tissue oxygenation value and a previous tissue oxygenation value obtained from the same tissue;
      calculate a rate of change for the change in tissue oxygenation;
      based on the rate of change, calculate an estimated time to exhaustion for the user; and
      based upon the estimated time to exhaustion for the user, transmitting an electronic signal with instructions to adjust, in real-time, the equipment device utilized by the user during the session to modify energy requirements to perform the session,
      wherein adjusting the equipment device increases the time to exhaustion of a user by at least 5%.
2. The apparatus of claim 1, wherein the equipment device comprises footwear worn by the user, and wherein the modification of energy requirements comprises modifying the footwear.
3. The apparatus of claim 2, wherein the modification is selected from the group consisting of: midsole compression stiffness, bending stiffness, midsole geometry, heel-toe offset, forefoot bending stiffness, adjustable air, mass distribution, upper stiffness/tightness, and combinations thereof.
4. The apparatus of claim 1, wherein the modification is configured to increase the energy requirements.
5. The apparatus of claim 1, wherein the tissue oxygenation data comprises data from an inactive muscle.
6. The apparatus of claim 1, wherein the previous tissue oxygenation value is a first oxygenation value and the current tissue oxygenation value is a second oxygenation value, and wherein the computer-readable medium comprises computer-executable instructions that when executed by the processor perform at least:
   calculate a change in tissue oxygenation as a difference between a third tissue oxygenation value and the second tissue oxygenation value obtained from the same tissue;
   calculate a second rate of change for the change in tissue oxygenation;
   based on the second rate of change, calculate an updated estimated time to exhaustion for the user; and
   based upon the updated estimated time to exhaustion for the user, transmitting an electronic signal configured to perform at least one of:
      adjust, in real-time, the equipment device utilized by the user during the session to modify the energy requirements to perform the session; and
      causing an output configured to notify the user to alter behavior to result in a different time to actual exhaustion.

* * * * *

UNITED STATES PATENT AND TRADEMARK OFFICE
CERTIFICATE OF CORRECTION

PATENT NO. : 10,524,728 B2  
APPLICATION NO. : 15/167241  
DATED : January 7, 2020  
INVENTOR(S) : Kirby et al.

Page 1 of 3

It is certified that error appears in the above-identified patent and that said Letters Patent is hereby corrected as shown below:

In the Drawings

Sheet 31 of 43 FIG. 28:  
Delete label "2200" and insert -- 2800 -- (as shown on the attached drawing sheet)

Sheet 32 of 43 FIG. 29:  
Insert label -- 2900 -- (as shown on the attached drawing sheet)

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*